(12) United States Patent
Girmonsky et al.

(10) Patent No.: US 7,134,341 B2
(45) Date of Patent: Nov. 14, 2006

(54) METHODS AND DEVICES FOR DETERMINING THE RESONANCE FREQUENCY OF PASSIVE MECHANICAL RESONATORS

(75) Inventors: Doron Girmonsky, Raanana (IL); Ran Eisenberg, Tel Aviv (IL); Nissim Avraham, Rishon LeZion (IL)

(73) Assignee: Zuli Holdings Ltd, Tel Aviv (IL)

( * ) Notice: Subject to any disclaimer, the term of this patent is extended or adjusted under 35 U.S.C. 154(b) by 123 days.

(21) Appl. No.: 10/828,218

(22) Filed: Apr. 21, 2004

(65) Prior Publication Data

US 2004/0211260 A1 Oct. 28, 2004

Related U.S. Application Data

(60) Provisional application No. 60/465,785, filed on Apr. 28, 2003.

(51) Int. Cl.
*G01N 29/04* (2006.01)
*A61B 8/00* (2006.01)

(52) U.S. Cl. .............. 73/579; 73/597; 73/602; 600/437

(58) Field of Classification Search ............ 73/579, 73/597, 602, 514.27, 514.29, 54.41, 657, 73/625, 626; 600/438, 437
See application file for complete search history.

(56) References Cited

U.S. PATENT DOCUMENTS

| | | | | |
|---|---|---|---|---|
| 4,237,454 A | * | 12/1980 | Meyer ................. | 340/682 |
| 4,733,561 A | * | 3/1988 | Gilby .................. | 73/579 |
| 4,884,450 A | * | 12/1989 | Greenwood et al. ...... | 73/702 |
| 5,260,762 A | * | 11/1993 | Telle .................. | 356/5.09 |
| 5,524,636 A | | 6/1996 | Sarvazyan et al. | |
| 5,619,997 A | | 4/1997 | Kaplan | |
| 5,749,364 A | | 5/1998 | Sliwa, Jr. et al. | |
| 5,786,735 A | * | 7/1998 | Su .................... | 331/158 |
| 5,989,190 A | | 11/1999 | Kaplan | |

(Continued)

OTHER PUBLICATIONS

U.S. Appl. No. 10/876,781, filed Jun. 28, 2004, Kaplan.

(Continued)

*Primary Examiner*—Hezron Williams
*Assistant Examiner*—Jacques Saint-Surin
(74) *Attorney, Agent, or Firm*—AlphaPatent Associates Ltd.; Daniel J. Swirsky

(57) ABSTRACT

Methods and systems for determining the resonance frequency of a resonator, using the Doppler effect. An interrogating sonic beam including a carrier frequency and one or more resonator exciting frequencies is directed at a resonator disposed in a measurement environment. Resonator vibrations are excited by the resonator exciting frequencies. The carrier frequency is modulated by the vibrating part(s) of the resonator. The returning signal is received and analyzed to determine the amplitude of the Doppler shifted sideband frequencies. The resulting data is processed to determine the resonator's resonance frequency. Using calibrated resonating sensors having a resonance frequency that varies as a function of a physical parameter in a measurement environment, the method and systems allow determining the value of the physical variable from the sensor's resonance frequency. The methods and systems may be used, inter alia, to determine intraluminal blood pressure in various parts of a cardiovascular system, the pressure of intra-cranial fluids, the pressure of fluids in various bodily cavities by using implantable calibratable resonating pressure sensors. The methods and systems may also be used for determining the pressure in various industrial measurement environments and enclosures. Methods and systems are provided for detecting the sensor and for centering the interrogating beam on the sensor.

112 Claims, 17 Drawing Sheets

U.S. PATENT DOCUMENTS

| | | |
|---|---|---|
| 5,997,477 A | 12/1999 | Sehgal |
| 6,083,165 A | 7/2000 | Kaplan |
| 6,301,968 B1 * | 10/2001 | Maruyama et al. ............ 73/657 |
| 6,305,226 B1 * | 10/2001 | Barber et al. ................. 73/606 |
| 6,312,380 B1 | 11/2001 | Hoek et al. |
| 6,331,163 B1 | 12/2001 | Kaplan |
| 6,461,301 B1 | 10/2002 | Smith |
| 6,470,753 B1 * | 10/2002 | Maruyama ................... 73/657 |
| 6,671,638 B1 * | 12/2003 | Kitazumi et al. ............. 702/75 |
| 6,770,032 B1 | 8/2004 | Kaplan |
| 6,787,051 B1 | 9/2004 | Silverbrook |
| 6,970,742 B1 | 11/2005 | Mann et al. |
| 2005/0148205 A1 | 7/2005 | Franosch et al. |
| 2005/0288590 A1 | 12/2005 | Kaplan |

OTHER PUBLICATIONS

U.S. Appl. No. 10/876,763, filed Jun. 28, 2004, Kaplan.
U.S. Appl. No. 09/004,420, filed Jan. 8, 1998, Richter et al.

* cited by examiner

METHODS AND DEVICES FOR DETERMINING THE RESONANCE FREQUENCY OF PASSIVE MECHANICAL RESONATORS

CROSS-REFERENCE TO RELATED APPLICATIONS

This application claims priority from U.S. provisional patent application Ser. No. 60/465,785 filed on Apr. 28, 2003.

FIELD OF THE INVENTION

The present invention relates to methods and systems for using the Doppler effect for determining the resonance frequency of resonators and of ultrasonic sensors in general and to the use of Doppler effect for sensor detection and beam centering and for resonance frequency determination in passive ultrasonic sensors in particular.

BACKGROUND OF THE INVENTION

Methods, devices and systems, using ultrasonically activated passive sensors usable for sensing and measuring the values of different physical parameters within a human body or in other environments and scientific and industrial applications, have been described. U.S. Pat. No. 5,619,997 to Kaplan, incorporated herein by reference in its entirety for all purposes, discloses a passive sensor system using ultrasonic energy. An ultrasonic activation and detection system ultrasonically activates passive sensors having vibratable parts (such as vibratable beams or vibratable membranes) by directing a beam of ultrasound at the passive sensor or sensors. The sensor(s) may be implanted in a body or disposed in other environments. The activated passive sensor(s), or vibratable parts thereof, vibrate or resonate at a frequency which is a function of the value of the physical variable to be measured. The passive sensors thus absorb ultrasonic energy from the exciting ultrasonic beam mostly at the frequency of vibration (resonance frequency) of the sensor. The frequency (or frequency range) at which the passive sensor absorbs energy may be detected by a suitable detector and used to determine the value of the physical parameter.

The physical parameters measurable with such passive ultrasonic sensors may include, but are not limited to, temperature, pressure, the concentration of a chemical species in the fluid in which the sensor is immersed, and the thickness of a layer of substance deposited on the vibratable part of the sensor.

If the exciting ultrasonic beam is pulsed (or is an abruptly terminated CW beam), the ultrasonic sensor may continue to vibrate after the pulse (or the CW beam) terminates. The ultrasonic radiation emitted by the activated passive sensor after turning the exciting ultrasonic beam off may be detected and used to determine the value of the physical parameter of interest.

Since more than one physical variable may influence the vibration frequency of passive sensors, a correction may be needed in order to compensate for the effects of other physical parameters unrelated to the physical parameter which needs to be determined on the measured sensor vibration frequency. For example, if pressure is the physical parameter to be determined, changes in temperature may affect the vibration frequency of the sensor. U.S. Pat. Nos. 5,989,190 and 6,083,165 to Kaplan, both of which are incorporated herein by reference in their entirety for all purposes, disclose compensated sensor pairs and methods for their use for compensating for the effects of unrelated different physical variables on the determined value of another physical variable which is being determined. For example, such compensated sensor pairs, may be used for compensating for inaccuracies in pressure measurements due to temperature changes.

Typically, the size of implantable passive ultrasonic sensors, such as but not limited to intraluminal passive ultrasonic pressure sensors represents a design compromise. Decreasing the sensor's size may allow implantation in smaller intraluminal spaces and other body spaces and may decrease interference with blood flow or flow of other bodily fluids in intraluminal and other intra-cavity spaces. Smaller sensor size may also be advantageous in cases in which a number of sensors need to be implanted at the same location.

However, decreasing the sensor dimensions may also decrease the dimensions of the vibratable membrane which may decrease the energy absorbable from the exciting ultrasonic beam and the total energy radiated by the sensor at or about the resonance frequency. This may decrease the returned signal's strength and (assuming a fixed noise level) decrease the signal to noise ratio (S/N).

Additional problems which may be encountered with passive ultrasonic sensors when a narrow interrogating ultrasound beam is used to excite the passive sensor relate to the need to center the interrogating beam on the sensor in order to increase the S/N and the need to distinguish between the signal emitted by the sensor at the resonance frequency and spurious echoes reflected from reflecting surfaces other than the vibratable membrane of the sensor (such as, for example, echoes reflected from non-vibratable sensor surfaces and echoes reflected from various reflecting interfaces).

SUMMARY OF THE INVENTION

The present invention is directed to methods devices and systems for determining the resonance of vibratable resonators. The vibratable resonator may be any type of resonator having one or more vibratable parts or vibratable structures. The resonators may include, but are not limited to, any suitable type of vibratable resonator or vibratable resonating sensor for sensing a physical variable in a measurement environment.

The present invention provides a method for determining the resonance frequency of a vibratable resonator. The method includes the step of subjecting the resonator to a sonic beam having one or more resonator exciting frequencies for exciting vibrations of the vibratable resonator, and a carrier frequency capable of being frequency modulated by vibrations of the vibratable resonator. The carrier frequency is higher than the resonator exciting frequencies. The method also includes the steps of receiving returning sonic signals from the vibratable resonator, and processing the returning signals to determine the resonance frequency of said vibratable resonator.

The present invention also provides a system for determining the resonance frequency of a vibratable resonator. The system may include a transmitter unit configured for directing at the vibratable resonator a sonic beam including one or more resonator exciting frequencies and a carrier frequency higher than the resonator exciting frequencies. The system may also include a receiver unit configured for receiving signals returning from said vibratable resonator, and a processing unit operatively coupled to the transmitter unit and to the receiver unit. The processing unit is configured for processing the returning signals to obtain data representing the amplitude of the signals at frequencies representing Doppler shifted frequency components of the carrier frequency and for determining the resonance frequency of the vibratable resonator from the data.

The present invention also provides a system for determining the resonance frequency of a vibratable resonator, the system may include transmitting means configured for directing at the vibratable resonator a sonic beam including one or more resonator exciting frequencies and a carrier frequency higher than the exciting frequencies. The system may further include receiving means configured for receiving signals returning from the vibratable resonator, and processing means operatively coupled to the transmitting means and to the receiving means. The processing means may be configured for processing the returning signals to obtain data representing the amplitude of the signals at frequencies representing Doppler shifted frequency components of the carrier frequency and for determining the resonance frequency of the vibratable resonator from the data.

In accordance with an embodiment of the invention the system may include a pressure measuring unit or a barometer suitably coupled to the system for determining the external pressure in the vicinity of the system. The system may use the value of the measured external pressure for selecting the appropriate resonator exciting frequencies to be used.

In accordance with one embodiment of the invention, the sensor or resonator may be a pressure sensitive passive vibratable ultrasonic sensor, but other sensor types may also be used. The vibratable resonators or sensors may be passive sensors or active sensors, or any other type of vibratable resonator or sensor known in the art.

In accordance with an aspect of the invention, the method may include directing a sonic beam including a carrier frequency and one or more resonator exciting frequencies at the vibratable resonator or sensor and receiving a returning signal. The returning signals may be analyzed to determine the resonance frequency of the vibratable part(s) of the resonator or sensor.

The carrier frequency may be higher than the resonator exciting frequencies and may be selected far enough from the resonator resonance frequency range such that the carrier does not induce substantial vibrations of the vibratable part(s) of the resonator. The resonator exciting frequencies may be selected to be within resonance frequency range of the resonator or sensor.

An aspect of the invention is that the vibrations of the vibratable part or parts of the resonator may be excited by the resonator exciting frequency or frequencies. The carrier frequency in the sonic beam may be reflected from the vibrating part(s) of the resonator or sensor.

The carrier frequency may be modulated by the vibrations of the vibratable part(s) according to the Doppler phenomenon. The signals returning from the vibratable part(s) of the resonator or sensor may include Doppler shifted frequencies different than the transmitted carrier frequency.

The signals returning from the resonator or sensor may be acquired and processed. In accordance with an aspect of the invention, the acquired returning signal may be digitized and processed using a digital Fourier transform method to obtain frequency domain data representing the acquired returning signal. The Doppler shifted frequencies may be represented by frequency sidebands flanking the carrier frequency. The amplitude of the sidebands may be determined.

For each resonator exciting frequency in the transmitted sonic beam, the relevant sideband amplitudes may be determined and a computed sideband amplitude value may be obtained. The sideband amplitude value (for any particular resonator exciting frequency) may be computed as the amplitude of one sideband selected from the two sidebands associated with each resonator exciting frequency, or may be computed as a mean sideband amplitude value computed from both sideband amplitudes (an arithmetic or geometrical mean of the two sideband amplitudes may be used, but other averaging methods may also be used).

The resonator or sensor exciting frequency that is closest to the resonance frequency of the resonator will have the highest sideband amplitude. Therefore, in accordance with an embodiment of the invention, the resonance frequency of the resonator or sensor may be determined as the resonator exciting frequency that resulted in the maximal sideband amplitude value. In accordance with another embodiment of the invention, the method may determine the sideband amplitude values for each resonator exciting frequency and may fit a curve to the data points (each point includes a sideband amplitude value and a frequency value representing the resonator exciting frequency associated with the sideband amplitude value). The maximum point of the fitted curve may be computed and the frequency at the maximum point may be taken as the resonance frequency of the resonator or sensor.

An aspect of the present invention is that by determining the signal amplitudes at the Doppler shifted frequencies it may be possible to avoid the main sources of noise which are due to reflections (echoes) at the carrier frequency returning from the non-vibratable resonator part(s) and/or from other reflecting parts or interfaces in the environment in which the resonator or sensor is disposed. This is based on the fact that the Doppler shifted frequency components are present in the signal parts which are reflected from the vibrating part(s) of the resonator or sensor, while their intensity may be orders of magnitude smaller in the signal parts which are reflected from non-vibratable parts of the resonator or in other echoes returning from other parts or interfaces of the measurement environment.

The sonic beam may be transmitted in various different configurations. In accordance with one embodiment of the invention, the carrier frequency and/or the resonator exciting frequencies may be transmitted as a continuous wave sonic beam.

In accordance with another embodiment of the invention, the carrier frequency and/or the resonator exciting frequencies may be transmitted as frequency bursts in a sonic beam. One possibility may be to transmit the carrier frequency as a continuous wave and the resonator exciting frequencies as frequency bursts. All of the resonator exciting frequencies may be transmitted within the same burst, or, alternatively, may be transmitted as a series of sequential bursts. Each burst in the series may include a different subgroup of the resonator exciting frequencies. A subgroup may include one or more resonator exciting frequencies.

In accordance with another embodiment of the invention, the sonic beam may include a series of bursts separated by time periods in which no signal is transmitted. In this case, each frequency burst may include the carrier frequency and one or more resonator exciting frequencies.

In accordance with another embodiment of the invention the sonic beam may include the carrier frequency and one or more chirps or frequency sweeps which may include sweeps in the frequency range covered by the resonator exciting frequencies.

The returning signals may be sampled and processed using various different methods. In accordance with an embodiment of the invention, the method and system may sample the entire returning signals but process only portions thereof. If frequency bursts are used, only part of the returning signals may be processed to ensure processing data from times at which the frequency content of the signal has stabilized (to avoid spurious frequencies present near the time of initiation and termination of frequency bursts).

In accordance with another embodiment of the invention the method and system may sample only usable parts of the returning signal by sampling selected portions of the returning signals. The sampled portions of the returning signal may be recorded. The recorded signals or portions of the recorded signals may be processed to determine the resonance frequency of the resonator.

When a vibratable sensor is used which has a resonance frequency depending on the value of a physical variable in the measurement environment, the determined resonance frequency of the sensor may be used to obtain a value for the physical variable in a measurement environment. The physical variable may be any physical variable that may be sensed by a resonating sensor. Examples are given using pressure sensors for measuring pressure values (in-vivo, or in any other measurement environment) but other physical variables such as temperature or osmotic pressure, or the like may also be measured. If the resonating sensor is a calibratable sensor, the sensor may be calibrated prior to use and calibration data may be obtained and used in measurements. Such calibration data may allow the correlating of measured values of the sensor's resonance frequency with the values of the physical variable used in the calibration of the sensor. Such calibration data may be in the form of a look-up table or in the form of an empirical or analytical calibration equation allowing the determining or computing the value of the physical variable from determined resonance frequency values, or the like. The pressure sensors may be calibrated in a suitable pressure chamber prior to implantation.

In accordance with one embodiment of the present invention, the sensors may be implantable passive ultrasonic sensors that may be implanted in various parts of a cardiovascular system to determine the blood pressure therein. In accordance with other embodiments of the invention the sensors may be implanted in other parts of an organism or mammal to measure the pressure therein For example, the method may be used to measure intra-cranial pressure values using intra-cranially implanted sensors. The method may also be used for pressure measurements in an annurismal sac after annurismal endovascular repair.

In accordance with an embodiment of the present invention, the method may be an open loop method. In the open loop measurement method, at each measurement time period, the system transmits the same plurality sensor exciting frequencies.

In accordance with another embodiment of the present invention, the method may be a closed loop measurement method. Such a method may be useful, inter alia, for measurements of a periodically varying parameter, such as, for example the periodically varying (pulsatile) intraluminal blood pressure within a blood vessel. In the closed loop method, the system may change or adapt the sensor exciting frequencies in accordance with an estimated sensor's resonance frequency predicted for the time at which the next measurement is performed.

The estimation of the predicted resonance frequency for the next measurement may be performed using different methods. In accordance with one such possible method, at the beginning of a measurement session, the system performs preliminary measurements within a selected test period using the open loop method. After sufficient data is collected the system may compute average cycle data that represents an averaged cycle of the periodically varying pressure. The average cycle data may be used to predict the estimated resonance frequency for the next measurement period and may be used to select a set of appropriately optimized resonator exciting frequencies based on the estimate to improve accuracy and sensitivity.

The averaged cycle data may be the range of the resonance frequency values (expressed as the maximal and minimal frequency values from all measurements performed at the same time relative to the beginning of the pulse cycle over a few measured cycles).

The averaged cycle data may also be a mean sensor resonance frequency value determined from all measurements performed at a similar time relative to the beginning of the pulse cycle over a few measured cycles. The data may also include for each mean value a statistical parameter such as, for example, the standard deviation of the mean or the variance of the mean, or other suitable parameters.

The method may compute from the estimated sensor resonance frequency a set of sensor exciting frequencies for use in the next measurement. The computed frequency set may be optimized for determining the sensor's resonance frequency more accurately.

The systems and methods of the invention may be used for measuring pressure or other physical variables of interest in many different medical applications, and various industrial applications which require measurement of pressure or other physical variables in enclosed measurement environments, such as, but not limited to, chemical reactors or other reactors, various types of tubes and pipes and other enclosed spaces, or any other type of measurement environments.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Notation Used Throughout

Figure 1A:
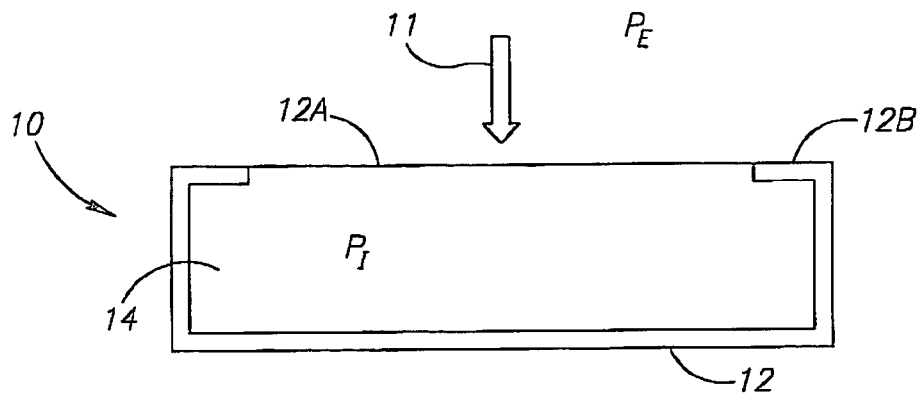
FIGS. 1A–1C are schematic cross-sectional views of a prior art passive ultrasonic pressure sensor at three different external pressure values.

The following notation is used throughout this document.

| Term | Definition |
| --- | --- |
| µm | micrometer |
| A/D | Analog to Digital |
| AC | Alternating Current |
| AFE | Analog Front End |
| BB | Base band |
| BPF | Band Pass Filter |
| BW | Bandwidth |
| CHF | Congestive Heart Failure |
| CW | Continuous wave |
| D/A | Digital to Analog |
| dB | Decibel |
| dBr | Decibel (relative) |
| DC | Direct Current |
| DFT | Digital Fourier Transform |
| ECG | Electrocardiogram |
| FDA | Food and Drug Administration |
| FFT | Fast Fourier Transform |
| FM | Frequency Modulation |
| HPF | High Pass Filter |
| Hz | Hertz |
| IF | Intermediate Frequency |
| IQ | In Phase and Quadrature |
| KHz | Kilohertz |
| LPF | Low Pass Filter |
| MHz | Megahertz |
| SNR | Signal to Noise Ratio |
| Torr | Torriceli (pressure unit) |
| US | Ultrasound |

For the purposes of this application the term "sonic beam" defines any beam of mechanical vibrational energy capable of propagating in a physical medium in which a resonating sensor may be disposed or implanted, including but not limited to beams of sound and beams of ultrasound. The frequency range of the vibrational energy of the sonic beam of the present invention is not limited to the audible and medical ultrasound frequency range but may include any vibration frequencies that may propagate in the medium in which the resonating sensor is disposed.

The term "medium" defines, for the purposes of this application, any type of substance or material or any combination of substances or materials through which a sonic beam may propagate. The medium may be homogenous or non-homogenous. The substances or materials in a medium may include, but are not limited to solids, liquids, fluids and gasses and any mixtures thereof and may include, but are not limited to solid and/or semi-solid objects or particles, gels, colloids, and the like. The medium may also be any type of composite structure, or any body of any organism, animal or human body or any parts or organs of such organisms, animals or humans in which a resonator or a resonating sensor may be disposed or implanted.

The term "vibratable resonator" defines, for the purposes of this application, any type of physical device having one or more vibratable parts that may be vibrated by a sonic beam propagating in a medium in which the physical device is disposed.

The term "resonator exciting frequency" defines, for the purposes of this application, a frequency included in a sonic beam that may excite a substantial vibration of one or more vibratable parts of a vibratable resonator.

The term "sensor exciting frequency" defines, for the purposes of this application, a frequency included in a sonic beam which may excite a substantial vibration of one or more vibratable parts of a sensor disposed in a measurement environment.

The term "carrier frequency" defines, for the purposes of this application, a frequency included in a sonic beam which may be reflected from a vibratable part of a vibratable resonator and which may be modulated by being Doppler shifted by a vibration of one or more vibratable parts of a vibratable resonator.

The term "burst" is defined, for the purposes of this application, as a finite duration of a sonic beam including a plurality of cycles of one or more sonic frequencies.

It is noted that, for the purposes of the present application, the word "sonic" in terms such as, "sonic burst", "sonic frequency burst" and the like, is used in a broad sense to define a broad vibrational frequency range which may include, but is not limited to, audible and non-audible vibrational frequencies and various ultrasound frequencies, such as, but not limited to, ultrasound frequencies used in medical ultrasonic devices.

It is noted that while the systems, devices and methods disclosed herein describe using a passive ultrasonic sensor for measuring blood pressure within a blood vessel using the Doppler effect, similar systems methods and devices may also be used for measuring a static or a dynamically changing pressure within other body fluids and/or body cavities or other organs. For example, the systems, devices and methods of the present invention may also be applied for measurement of intraocular pressures using intraocularly implanted passive ultrasonic sensors, for measuring blood pressure within any part of a blood vessel (such as, but not limited to, an artery or a vein), for measuring blood pressure within any part of a heart, including but not limited to a cardiac atrium, a cardiac ventricle, the aorta or any other lumen or cavity of the heart or of any blood vessels associated with the heart or with any other body organ. Thus, it will be appreciated by the person skilled in the art that the methods described herein are not limited to the measurement of blood pressure in a blood vessel and may be applied to performing many other measurements of a physical parameter using implanted passive ultrasonic sensors.

Moreover, the methods and devices described herein may be employed to determine the resonance frequency of ultrasonically vibratable resonators. Such resonators may include (but are not limited to) resonators included in or forming part of sensors that are designed to measure physical variables, such as, inter alia, the pressure, in a measurement environment.

Exemplary sensors that may be employed using the methods and devices of the present invention may include implantable sensors for medical or other uses, and non-implanted sensors for medical veterinary, or other industrial sensing applications. The physical parameters which may be measured by such sensors may include, but are not limited to, temperature, pressure, osmotic pressure, the concentration of a chemical species, or ion or molecule in a medium, the amount of tissue or other deposits overlying the sensor, and the like. The methods and devices disclosed herein may also be used for physical parameter sensing in various types of enclosed spaces, such as, but not limited to, food cans, industrial piping, process chambers, reactors, pressurized cylinders or containers, and the like.

Figure 1B:
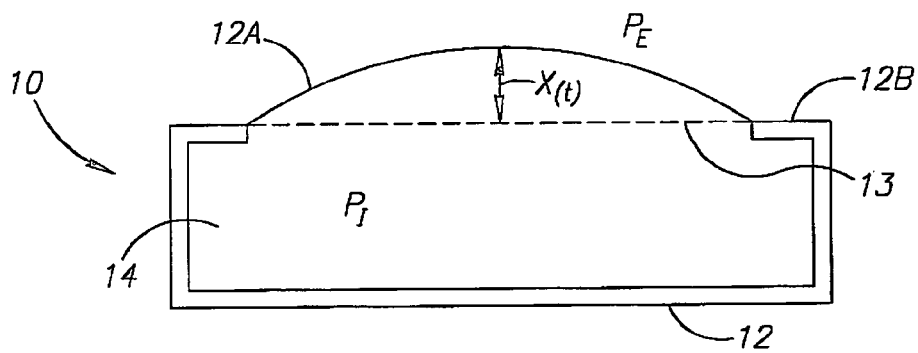
Figure 1C:
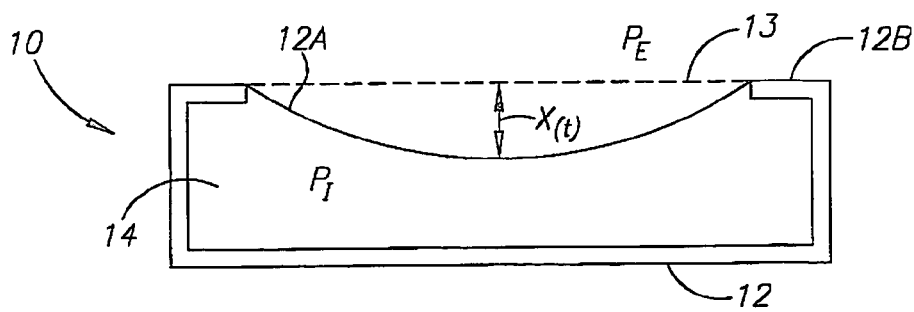

Reference is now made to FIGS. 1A–1C which are schematic cross-sectional views of a prior art passive ultrasonic pressure sensor at three different external pressure values.

The passive ultrasonic sensor 10 has a housing 12. A thin vibratable membrane 12A is sealingly attached to, or forms an integral part of the housing 12. The sensor 10 may also have a non-vibratable surface 12B located on the side of the housing 12 on which the vibratable membrane 12A is located.

The housing 12 and the vibratable membrane 12A form a sealed chamber 14. The sealed chamber 14 has a gas or a mixture of gases therein. The internal pressure inside the sealed chamber is $P_I$. The internal pressure $P_I$ may be set at a desired value at the time of manufacturing of the sensor 10 by sealing the housing 12 in the presence of a gas or a mixture of gasses having the desired pressure value. The external pressure of the medium outside the sensor 10 is $P_E$.

FIG. 1A schematically illustrates a condition in which the pressure within the sealed chamber 14 and the external pressure in the medium outside of the sensor 10 are equal ($P_I=P_E$) and the vibratable membrane 12A is planar.

The vibratable membrane 12A may be made to vibrate by directing a beam of ultrasound (not shown) onto the sensor 10. Such a beam of ultrasound may excite the vibratable membrane 12A and may cause the membrane 12A to vibrate. When the membrane 12A is vibrating it may radiate or emit an ultrasonic signal at its vibration frequency (or at its vibration frequencies if it vibrates at more than one vibration mode).

The vibratable membrane 12A may keep emitting a continuous ultrasonic signal as long as the membrane 12A is being excited by the incident ultrasonic beam directed onto the sensor 10. If the exciting ultrasonic beam is shut off, the membrane 12A may keep vibrating for some time after the exciting beam is switched off and may emit an ultrasonic signal having an amplitude which decays in time. Such continuous or decaying ultrasonic signals emitted by the passive sensor 10 may be detected and further processed to determine the external pressure $P_E$ as disclosed in detail hereinafter.

Typically, the membrane 12A has a resonance frequency that depends, inter alia, on the shape, mass, thickness of the membrane 12A. When the frequency of the exciting ultrasonic beam is at the natural resonance frequency of the membrane 12A, the amplitude of the vibration of the membrane 12A is maximal and the amplitude of the ultrasonic signal emitted by the resonating membrane 12A is maximal. If the frequency of the exciting ultrasonic beam is different than the resonance frequency of the membrane 12A (by being either higher or lower than the resonance frequency of the membrane 12A), the amplitude of the vibrations of the membrane 12A is reduced and the intensity of the ultrasonic signal emitted by the vibrating membrane 12A is reduced.

FIG. 1B schematically illustrates the sensor 10 when the internal pressure within the chamber 14 is larger than the external pressure outside the sensor 10 ($P_I>P_E$). Under such conditions the membrane 12A is pushed outward and may assume a convex shape. The double headed arrow labeled X(t) represents the displacement of the center of the membrane 12A from a plane representing the position of the membrane 12A under conditions in which $P_I$ is equal to $P_E$ (see FIG. 1A). The dashed line 13 schematically represents the position of the membrane 12A under the conditions in which $P_I$ is equal to $P_E$.

When $P_I>P_E$, the membrane 12A is stressed, and the resonance frequency of the membrane 12A is shifted to a higher frequency than its resonance frequency under non-stressed conditions.

FIG. 1C schematically illustrates the sensor 10 when the internal pressure within the chamber 14 is smaller than the external pressure outside the sensor 10 ($P_I<P_E$). Under such conditions the membrane 12A is pushed inward and may assume a concave shape. The double headed arrow labeled X(t) represents the displacement of the center of the membrane 12A from a plane representing the position of the membrane 12A under conditions in which $P_I$ is equal to $P_E$ (see FIG. 1A). The dashed line 13 schematically represents the position of the membrane 12A under the conditions in which $P_I$ is equal to $P_E$. It is noted that in FIG. 1C, X(t) assumes (arbitrarily) a negative value indicating that the displacement is in a direction opposite to the direction of the displacement of the membrane shown in FIG. 1B.

When $P_I<P_E$, the membrane 12A is stressed, and the resonance frequency of the membrane 12A is shifted to a higher frequency than its resonance frequency under non-stressed conditions.

Within a certain pressure range, the resonance frequency of the membrane 12A may be a function of the pressure difference $\Delta P=P_I-P_E$.

The pressure point within the working range of the sensor at which the resonance frequency of the membrane 12A of the sensor has the lowest value (a minimum point) is called the "flipping point" of the sensor. Within the working range of the sensor, as the pressure values increase to values higher than the flipping point pressure, the resonance frequency of the sensor increases since the vibratable membrane becomes increasingly stressed. Similarly, as the pressure values decrease to values lower than the flipping point pressure, the resonance frequency of the sensor increases since the vibratable membrane becomes increasingly stressed.

It is noted that the configuration and construction of ultrasonic sensors, is known in the art, is not the subject matter of the present invention, and is therefore nor described in detail hereinafter. Generally, many different types of ultrasonic sensors may be used in implementing the methods and systems of the present invention. For example, any of the passive ultrasonic sensors disclosed in U.S. Pat. Nos. 5,619,997, 5,989,190, and 6,083,165 may be used to implement the methods and systems of the present invention, but other suitable types of resonating ultrasonic sensors known in the art may also be used.

Figure 2:
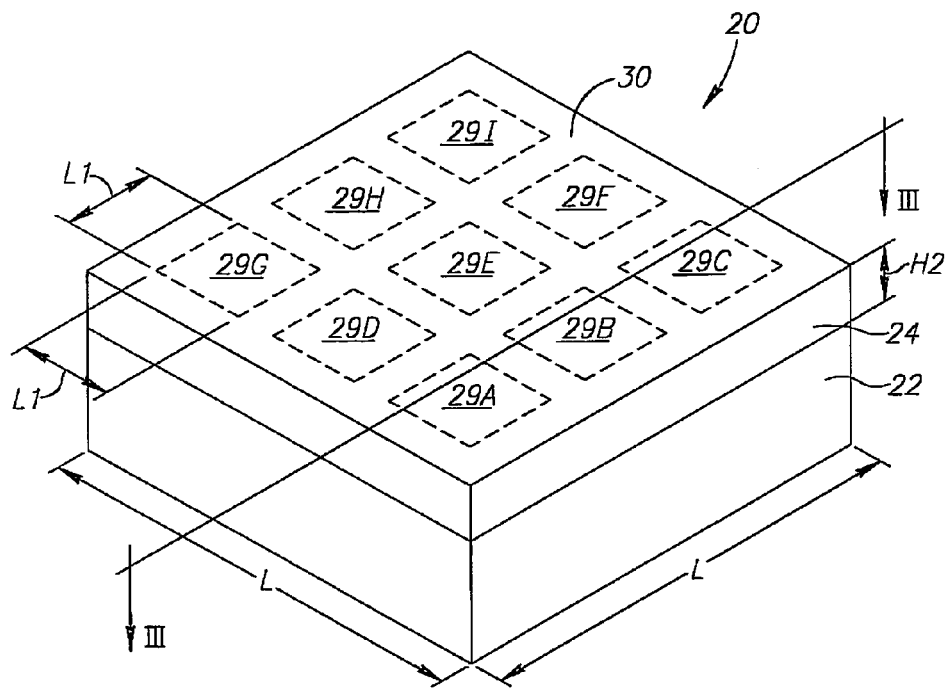
FIG. 2 is a schematic diagram illustrating an isometric view of an exemplary multi-membrane passive ultrasonic pressure sensor used in pressure determining experiments in accordance with the Doppler shift based method of the present invention.
Figure 3:
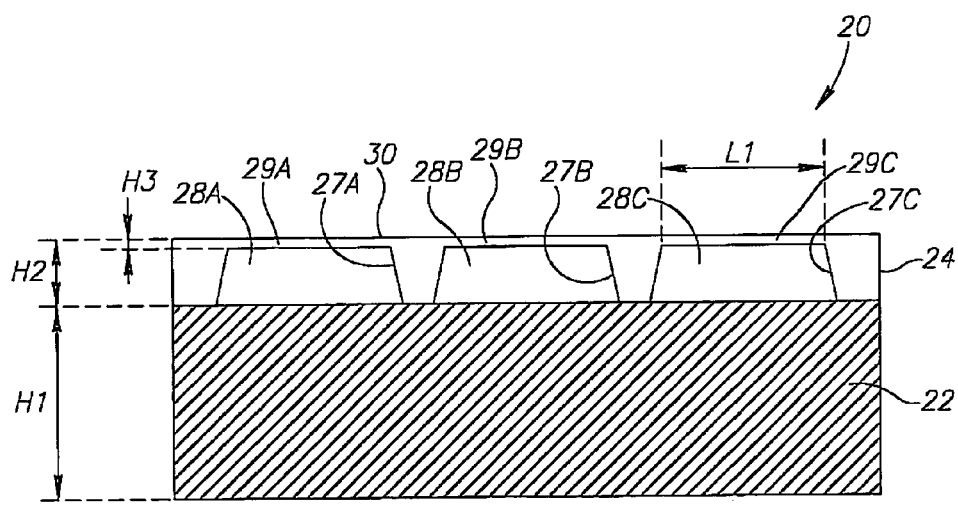
FIG. 3 is a schematic a cross sectional view of the sensor of FIG. 2 along the lines III—III.

Reference is now made to FIGS. 2 and 3. FIG. 2 is a schematic diagram illustrating an isometric view of an exemplary multi-membrane passive ultrasonic pressure sensor used in pressure determining experiments in accordance with the Doppler shift based method of the present invention, and FIG. 3 is a schematic a cross sectional view of the sensor of FIG. 2 along the line III—III.

The sensor 20 includes a flat substrate layer 22 made of PYREX® glass. The substrate layer 22 is shaped like a square slab having a side L of approximately 1 millimeter, and a thickness H1 of approximately 300 micrometers. A recessed layer 24 is sealingly bonded to the substrate 22. The recessed layer 24 is a single-crystal silicon layer having a square shape with a side L of approximately 1 millimeter and a thickness H2 of approximately 24 micrometers. The recessed layer 24 is processed using standard masking, photoresist, and etching methods, as is known in the art, for forming nine recesses in the layer 24. Three recesses 27A, 27B and 27C of the nine recesses of the sensor 20 are illustrated in the cross-sectional view of FIG. 3 (the remaining six recesses are not seen in FIG. 3) The recesses 27A, 27B and 27C have a blunt pyramidal shape. The recessed layer 24 is bonded to the flat substrate layer 22 as shown in FIGS. 2 and 3 in a controlled pressure chamber by using anodic bonding, as is known in the art. After bonding is completed, the sensor 20 has nine sealed chambers (not shown in FIG. 2) having substantially the same internal chamber pressure level $P_I$. The pressure $P_I$ may be set by suitably setting the pressure level in the pressure chamber (not shown) within which the layer 22 and the recessed layer 24 are bonded together to the desired pressure level. Three sealed chambers 28A, 28B and 28C of the nine chambers of the sensor 20 are illustrated in FIG. 3. The sealed chambers 28A, 28B and 28C have thin vibratable membranes 29A, 29B and 29C, respectively on their side opposite the substrate layer 22. The vibratable membranes 29A, 29B and 29C are substantially parallel to the flat substrate layer 22. The other remaining six sealed chambers (not shown in FIG. 3) have similar thin vibratable membranes (not shown in FIG. 3) forming part of the walls of the sealed chambers. Thus, the sensor 20 has nine thin vibratable membranes 29A, 29B, 29C, 29D, 29E, 29F, 29G, 29H, and 29I having a thickness H3 of approximately 0.8 micrometer.

Returning to FIG. 3, the vibratable membranes 29A, 29B and 29C forms part of the walls of the sealed chambers 28A, 28B and 28C, respectively. Each of the vibratable membranes 29A, 29B and 29C is shaped like a square membrane having a side L1 of approximately 220 micrometers. Turning briefly to FIG. 2, the dashed squares labeled 29A, 29B, 29C, 29D, 29E, 29F, 29G, 29H, and 29I schematically represent the positions, dimensions and arrangement of the nine vibratable membranes 29A, 29B, 29C, 29D, 29E, 29F, 29G, 29H, and 29I that are formed within the recessed layer 24.

It is noted that the configuration, material composition, and dimensions of the sensor 20 as disclosed hereinabove and used in the experiments described herein are given by way of example only. The present invention may be practiced with many other types of ultrasonic sensors, and many variations and permutations may be made to, inter alia, the sensor construction material composition, sensor dimensions, sensor shape, the number shape and/or dimensions and/or shapes and/or configuration of the vibratable membranes of the sensor. The parameters of the sensor such as, inter alia, the sensor's construction, materials, dimensions, internal pressure ($P_I$), and other sensor parameters may be modified in accordance with, inter alia, the specific application and the ultrasound frequencies used by the system.

When an incident ultrasound beam (not shown) containing the appropriate frequency or frequencies is directed incident to the sensor 20, each of the nine vibratable membranes 29A, 29B, 29C, 29D, 29E, 29F, 29G, 29H, and 29I, may vibrate as is known in the art, and may emit an ultrasonic signal at the resonance frequency of the membranes 29A, 29B, 29C, 29D, 29E, 29F, 29G, 29H, and 29I. Since the physical dimensions of the vibratable membranes 29A, 29B, 29C, 29D, 29E, 29F, 29G, 29H, and 29I are substantially similar (within manufacturing tolerances), the resonance frequencies of the vibratable membranes 29A, 29B, 29C, 29D, 29E, 29F, 29G, 29H, and 29I are substantially similar to each other. When the frequency of the ultrasonic beam is close to the resonance frequency (or frequencies) of the vibratable membranes 29A, 29B, 29C, 29D, 29E, 29F, 29G, 29H, and 29I, the amplitude of the returning ultrasonic signal generated by the vibratable membranes 29A, 29B, 29C, 29D, 29E, 29F, 29G, 29H, and 29I is maximal.

The degree of stress in each of the vibratable membranes 29A, 29B, 29C, 29D, 29E, 29F, 29G, 29H, and 29I of the sensor 20 depends, inter alia, on the difference in pressure between the external pressure $P_E$ outside the sensor 20 and the internal pressure $P_I$ inside the sealed chambers of the sensor 20. Therefore, the intensity of the ultrasonic signal returning from the sensor 20 may depend on the value of the pressure $P_E$ outside the sensor 20. This is similar to the behavior of the vibratable membrane 12A of the sensor 10 as disclosed in detail hereinabove.

Within a certain pressure range, the resonance frequency of the vibratable membranes 29A, 29B, 29C, 29D, 29E, 29F, 29G, 29H, and 29I may be a function of the pressure difference $\Delta P = P_I - P_E$.

When the sensor 20 is radiated with ultrasound waves, the vibratable membranes 29A, 29B, 29C, 29D, 29E, 29F, 29G, 29H, and 29I vibrate. The vibration frequency of the vibratable membranes 29A, 29B, 29C, 29D, 29E, 29F, 29G, 29H, and 29I is equal to the low frequency of the exciting ultrasound and the amplitude of the vibration of the vibratable membranes 29A, 29B, 29C, 29D, 29E, 29F, 29G, 29H, and 29I is a function of the energy of the exciting ultrasound beam and the sensor's resonance frequency.

Generally, single vibratable membrane passive ultrasonic sensors (such as, but not limited to, the sensor 10 of FIG. 1A–1C), multi-membrane passive ultrasonic sensors (such as, but not limited to, the sensor 20 of FIGS. 2–3) and other types of resonating sensors described herein or known in the art may be calibrated by experimentally determining the resonance frequency of the sensor at known pressure values in a pressure controlled environment. Such calibration may be used to obtain a look up table (LUT) that correlates resonance frequency and pressure values. When the sensor is positioned within a measurement environment, the LUT may be used to determine the pressure from the determined values of the resonance frequency of the sensor.

It may also be possible to use such an experimentally obtained LUT to find a function that defines the dependence of the resonance frequency of the sensor on the pressure outside the sensor, at least for a defined pressure range within the working range of the sensor. When the sensor is positioned within a measurement environment, such a function may be used for computing the pressure from the determined values of the resonance frequency of the sensor.

The resonance frequency of the sensor in a calibration environment or in a measurement environment may be determined by directing at the sensor a beam of acoustic energy (such as, but not limited to, a beam of sound or ultrasound) having a plurality of frequencies and measuring the amplitude of the signal returning from the sensor at each transmitted frequency. Theoretically, the amplitude of the reflected signal should be minimal at the resonance frequency of the sensor (due to high absorption at resonance). Practically, however, it may be difficult to accurately determine the resonance frequency of the sensor due to several reasons.

A problem often occurring with determining the resonance frequency of the membrane 12A (or of the resonance frequency of any other resonating structure included in such a sensor, such as, but not limited to the resonance frequency of the vibratable membranes 29A, 29B, 29C, 29D, 29E, 29F, 29G, 29H, and 29I of the sensor 20) may result from the fact that the transmitted and returned ultrasonic signals are basically at the same frequency, or at relatively close frequencies. Therefore, the returned signal is "contaminated" by noise and by echoes. Such echoes may be returned by various structures of the body within which the sensor is disposed, or by ultrasound reflecting interfaces between bodily structures having different acoustic impedance values, as well as by the non-vibratable parts or surfaces of the sensor itself. For example, when the passive sensor 10 is implanted in a blood vessel (not shown) and an exciting ultrasonic beam (not shown) is directed towards the sensor 10 in the direction generally represented by the arrow labeled 11, the returning signal may include, inter alia, the signal generated by the resonating membrane 12A, an echo reflected from the non-vibratable part 12B of the sensor 10, and other echoes (not shown) of the exciting beam which are reflected from reflecting body parts (not shown) or interfaces within the body (not shown) in which the sensor 10 is implanted.

Similarly, the non vibratable parts of the surface 30 of the recessed layer 24 of the sensor 20 may also reflect echoes at a frequency close to or at the resonance frequency of the vibratable membranes 29A, 29B, 29C, 29D, 29E, 29F, 29G, 29H, and 29I.

The higher the intensity of the echoes in the returning ultrasonic signal, the more difficult it may be to detect and isolate that portion of the returned signal emitted by the resonating membrane 12A where the required information resides.

The methods of the present invention may be adapted to measure the blood pressure within a blood vessel and to present the pulsatile blood pressure variations within such a blood vessel. In order to measure the pressure, a sensor having one or more passive resonators (such as, but not limited to, the passive sensors 10 or 20 disclosed hereinabove, or any other suitable ultrasonic resonating sensor known in the art) is implanted inside the blood vessel. The sensor may change its resonance frequency as a function of the blood pressure as disclosed hereinabove. In order to find the resonance frequency of the resonating part of the sensor used, an ultrasound beam is directed at the sensor. The ultrasound beam may include one or more resonator exciting frequency components for excitation of the resonating part or parts of the sensor (such as, for example, the vibratable membrane 12A of the sensor 10, or the vibratable membranes 29A, 29B, 29C, 29D, 29E, 29F, 29G, 29H, and 29I, of the sensor 20, or the like). The ultrasound beam also includes a carrier frequency component that is higher than the resonator exciting frequency (or frequencies).

The one or more resonator exciting frequency excites oscillations of the vibratable membrane 12A of the sensor 10 or of the vibratable membranes 29A, 29B, 29C, 29D, 29E, 29F, 29G, 29H, and 29I of the sensor 20, or of any other vibratable sensor part or resonator(s) included in the sensor. The carrier frequency component which is returned (reflected) from the oscillating vibratable membrane(s) or from any other oscillating resonator member or part of the sensor used, is modulated with a Doppler shift due to the oscillation of the vibrating resonator(s). The Doppler modulated carrier frequency component in the ultrasonic signal returning from the sensor may then be received and analyzed to detect and measure the amplitude of the side band frequency components (the Doppler shifted frequency components) of the modulated carrier frequency as is disclosed in detail hereinafter to identify and to spatially locate the sensor, to assist in centering the interrogating ultrasound beam on the sensor and to find the resonance frequency of the sensor's vibratable membrane(s) or of any other resonating part or member or of the sensor which is being used.

The Doppler effect may be used to differentiate the returned modulated carrier signal from other echoes (which are not modulated). For example, by measuring and displaying a frequency domain plot of the amplitude of one or more of the Doppler shifted side bands as the ultrasound probe or transducer scans the body, the user or operator may know that the beam is directed at the sensor when such side bands are observed or otherwise detected and may be able to determine when the ultrasonic beam is accurately directed towards the implanted sensor by monitoring the changes of the amplitude of the side band peak(s) as the direction of the ultrasonic probe or transducer is changed. Maximizing the Doppler side band(s) amplitude may indicate that the sensor is correctly positioned within the ultrasound beam and may ensure that the received signal is indeed a signal returned from the sensor. This is because in signals which are returned from structures or interfaces other than the vibratable membrane or resonator of the sensor, the carrier frequency will not be modulated at the Doppler frequency because the reflecting structures or interfaces are not vibrating at or near the resonance frequency of the vibratable resonator or membrane of the sensor and the echoes of the carrier frequency returning from such non-vibrating structures or interfaces will not be Doppler modulated and will not have significant side band frequency components.

If an interrogating beam having a frequency close to the sensor's resonance frequency is used for sensor excitation (without using the carrier frequency of the present invention), the signal returning from the sensor may be contaminated by noise coming from various sources. One possible source of such noise is the reflection of the incoming interrogating beam from various non-vibratable surfaces of the sensor (referred to as the sensor's reflection noise, hereinafter). For example, the non-vibratable surface 12B of the sensor 10 (FIGS. 1A–1C), and the non-vibratable parts of the surface 30 of the recessed layer 24 of the sensor 20 (FIG. 2) may reflect the interrogating ultrasound beam. Such reflections may contain a range of frequencies substantially similar to the range of frequencies emitted by the vibratable membrane 12A and the vibratable membranes 29A, 29B, 29C, 29D, 29E, 29F, 29G, 29H, and 29I of the sensors 10 and 20, respectively. Because of the similarity of the frequency range of the sensor's reflection noise and the signal of interest emitted by the vibratable membranes of the sensors, it may be difficult to extract the relevant signal from such noise.

While it may be possible to reduce the sensor's reflection noise by reducing the size of the non-vibratable surfaces of the sensor facing the interrogating beam, this may not always be desirable or possible due to practical design or manufacturing considerations such as, inter alia, affecting the sensor's mechanical durability, increasing sensor's fragility, and other considerations.

In addition to the reflection noise discussed above, there may be other types of noise which may contaminate the signal of interest emitted from the vibratable parts of the resonating sensor. Such noise may include echoes and reflections of the interrogating beam by various objects in the measurement environment. For example, in sensors implanted in a body or in a bodily cavity such echoes may be reflected by interfaces between various different tissues or interfaces between various tissues and bodily fluids or gasses, bubbles within a bodily fluid, or the like. In other applications such echoes may be reflected by interfaces between various different objects or interfaces in the measurement environment, including, inter alia, walls or other reflecting objects surrounding or disposed in the measurement environment, or reflecting interfaces or bubbles in the measurement medium, or the like.

While the problem of echoes may be reduced in certain specific applications, for example, by suitable positioning of the sensor within the measurement environment, and by adjusting the direction of the interrogating beam to reduce the received echoes, this may not always be possible, especially in implanted sensor applications in which the sensor's placement is dictated by the measurement needs and in which the sensor(s), or the various tissues and/or organs surrounding the sensors may move or change their relative positions.

The methods, devices and systems disclosed herein provide a solution to the above described problems of sensor's reflection noise and various other echoes, by using two different types of frequencies in the interrogating beam. The first type of frequencies are exciting frequencies that excite the vibratable membrane(s) or other resonating part(s) of the resonating sensor and induce vibrations of these vibratable membrane(s) or resonating part(s). Preferably, the exciting frequencies are within a frequency range that includes the possible values of the resonance frequencies of the sensor or sensors in the pressure working range of the sensor or sensors.

The second type of frequency included in the interrogating ultrasonic beam is a carrier frequency that is substantially higher than the resonator or sensor exciting frequencies. The carrier frequency is preferably selected such that it is higher than any of the sensor exciting frequency and is sufficiently far away from the resonance frequencies of the sensor(s) possible within the sensor's or sensors' working pressure range. Thus, the carrier frequency is selected such that it imparts very little energy to the vibratable membrane(s) of the sensor(s) since it is far away from the resonance frequencies range possible within the pressure working range of the sensor(s) used in the measurement.

When the interrogating beam including the carrier frequency and one or more exciting frequencies is directed at the sensor or sensors, the vibratable membrane(s) or other resonating part(s) of the sensor vibrate at the exciting frequencies. The carrier frequency is reflected from the vibratable membrane(s) of the sensor (such as, for example, from the vibratable membrane 12A of the sensor 10 or from the vibratable membranes 29A, 29B, 29C, 29D, 29E, 29F, 29G, 29H, and 29I of the sensor 20), as well as from the non-vibratable parts of the sensor(s) (such as, for example, the non-vibratable surface 12B of the sensor 10, and the non-vibratable parts of the surface 30 of the recessed layer 24 of the sensor 20).

The part of the carrier wave reflected from the vibrating membrane(s) is Doppler shifted due to the vibrating movement of the membrane(s), as is known in the art. For each vibration frequency present in the vibrating membrane due to an exciting frequency of the interrogating beam, two frequencies are added to the reflected signal (at the carrier frequency±exciting frequency). If the number of exciting frequencies is N, the reflected signal may include the carrier frequency and 2N Doppler shifted frequency components. The amplitude of the reflected signal at each Doppler shifted frequency is proportional to the amplitude of the vibration of the vibratable membrane at the corresponding exciting frequency. Therefore, if we can measure the amplitudes of the Doppler shifted frequencies we may use this amplitude data to determine the frequency at which the vibration amplitude is maximal. This frequency represents the resonance frequency of the sensor at the time at which the measurement was performed (assuming the measurement was performed fast enough to ensure that the pressure does not change substantially during the time period used for acquiring the data of the returning signal).

Since the Doppler shifted frequencies may be sufficiently offset from the carrier frequency (along the frequency axis of a frequency domain representation of the returning signal) it may be possible by suitable signal processing methods (as is disclosed in detail hereinafter) to determine the amplitude of the returning signal at these Doppler shifted frequencies even though the carrier frequency has an amplitude which may be many orders of magnitude larger than the amplitude of the returning signal at the Doppler shifted frequencies.

Thus, since the relevant information resides in the amplitude of the Doppler shifted sideband frequencies, and most of the irrelevant noise in the returning signal (such as, for example, the sensor's reflection noise and the other echoes described hereinabove) are at the carrier frequency and at the exciting frequencies, it is relatively easy to measure the relevant amplitudes by separating the frequencies. For example, the measurement may be carried out by performing digital Fourier transform (DFT) on the processed digitized returning signal to provide frequency domain representation data, as is disclosed in detail hereinafter, or by using other suitable methods or algorithms for determining amplitude data at different frequencies.

Figure 4:
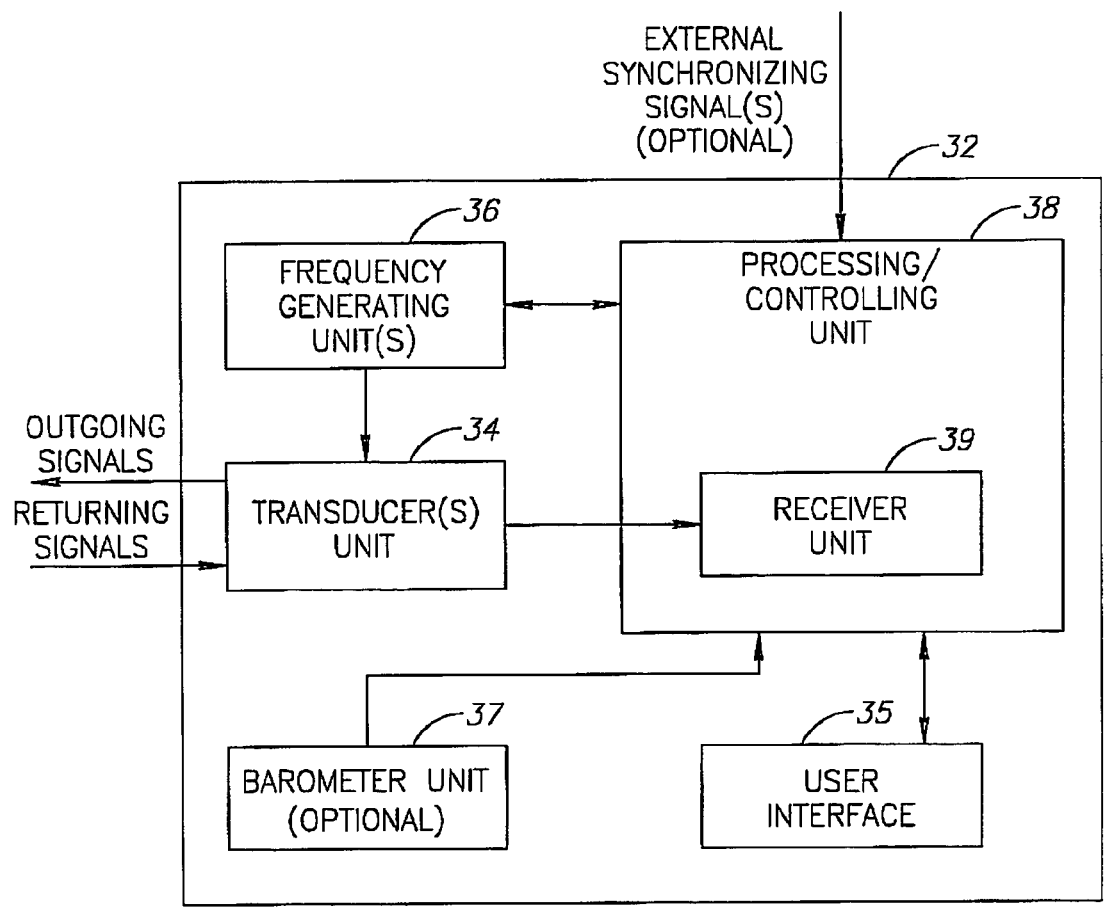
FIG. 4 is a schematic block diagram illustrating a system useful for determining the resonance frequency of a resonating sensor, in accordance with an embodiment of the Doppler measurement method of the present invention.

Reference is now made to FIG. 4 which is a schematic block diagram illustrating a system useful for determining the resonance frequency of a resonating sensor, in accordance with one embodiment of the Doppler measurement method of the present invention.

The system 32 includes a transducer(s) unit 34 for producing outgoing signals in the form of an interrogating acoustic beam that may be directed at the resonating sensor (not shown in FIG. 4). The transducer(s) unit 34 is also used for receiving the signals returning from the sensor when the sensor is interrogated with the interrogating beam. The transducer(s) unit 34 may include one or more transducers (not shown separately in FIG. 4, for the sake of clarity of illustration). The transducer(s) included in the transducer(s) unit 34 may be any transducer(s) suitable for controllably generating acoustic energy beams (such as, but not limited to sonic or ultrasonic beams) as is known in the art. For example, the transducer(s) unit 34 may be implemented using suitable piezoelectric transducers, but any other type of transducer(s) known in the art may be used to implement the transducer unit 34, such as, but not limited to, capacitive transducers, wideband capacitive transducers, composite piezoelectric transducers, electromagnetic transducers, various transducer array types and various suitable combinations of such transducers configured for obtaining different frequencies and/or beam shapes.

The system 32 also includes one or more frequency generating units 36 suitably coupled to one or more of the transducer units 34. The frequency generating unit(s) 36 are adapted for generating the carrier frequency and the resonator exciting frequencies of the interrogating acoustic beam, as disclosed hereinabove, the construction and operation of such frequency generating units is well known in the art, and is therefore not described in detail herein.

The system 32 may also include a processor/controller unit 38 suitably connected to the frequency generating unit(s) 36 for controlling the operation thereof. At least one transducer unit of the transducer unit(s) 34 is adapted for receiving the signals returning from the resonating sensor. The transducer or transducers used for receiving the returning signal may be coupled to a suitable receiver unit 39. The receiver unit 39 receives a signal representing the returning signal from the transducer unit and may process the signal to provide a conditioned processed signal to the processor/controller unit 38.

The system 32 may also (optionally) include a barometer unit 37 suitably connected to the processor controller unit 38. The barometer unit 37 may be any type of pressure measuring device known in the art. The barometer unit 37 may measure the external pressure in the environment in which the system 32 is disposed. The value of the external pressure may be suitably fed to the processing/controlling unit 38. For example, the barometer unit 37 may output digital data directly to the processing/controlling unit 38, or the barometer unit 37 may output an analog signal and a suitable A/D unit (not shown) may be used to digitize the analog signal and deliver the digitized signal to the processing/controlling unit. The determined external pressure value may be used by the system as disclosed in detail hereinafter.

The barometric pressure data may be used by the system for various purposes including, but not limited to, the selection of appropriate sets of sensor exciting frequencies as disclosed in detail hereinafter. The construction and operation of pressure measurement devices is well known in the art and is not the subject matter of the present invention and is therefore not described in detail hereinafter.

It is noted that while the receiver unit 39 of FIG. 4 is shown to be implemented as part of the processor/controller unit 38, this is not obligatory and the receiver unit 39 may also be implemented as a separate unit which may be suitably coupled to the transducer unit and to the processor/controller unit 38 for receiving signals from the transducer unit and for providing a conditioned signal to the processor/controller unit 38.

The processor/controller unit 38 may be connected to or may include therewithin a user interface 35. The user interface may include any suitable number of suitable input and output devices (not shown individually in FIG. 4, for the sake of clarity of illustration) suitable for receiving input or commands from a user of the system 32, and for providing output or data to the user or operator of the system 32. The input and/or output devices included in the user interface 35 may include, but are not limited to, any combination of control panels, keyboards, pointing devices (such as, but not limited to, a mouse, a light pen, a graphic tablet, or the like), touch sensitive display screens, monitors, data and/or image display devices, indicator lights, audio speakers or other audio output devices, printers, data storage devices of any type known in the art, and the like. Such display unit(s) or devices may be, but are not limited to, CRT display devices, LCD display devices, or any other suitable type of display device known in the art. The construction and operation of such input and output devices is well known in the art, and is therefore not described in detail hereinafter.

It is noted that any type of configuration known in the art may be used to implement one or more of the components of the system 32. For example, any electronic circuits used in any of the components of the system 32 may be implemented as analog circuits, digital circuits or hybrid analog/digital circuits. Moreover, any of the circuits or components of the system 32 may be implemented using discrete electronic or electrical components, Integrated circuits (IC), very large scale Integrated (VLSI) circuits, Digital signal processor (DSP) circuits, and any suitable combinations thereof, or the like. It is noted that some or all of the electronic components described may be integrated on a single chip (such as, for example an ASIC), or may be included in a single computer PC board.

In accordance with one embodiment of the invention, the processor/controller unit 38 may be implemented as, or may be formed as part of a computer (such as, but not limited to, a computer, a personal computer, a workstation, a minicomputer, a networked computer, a mainframe computer, a distributed processor configuration, a computer cluster configuration, microprocessor(s), microcontroller(s) or any other type of computer or processor configuration known in the art).

The processor/controller unit 38 may also include any type of suitable storage device or memory device (not shown in detail in FIG. 4) known in the art for temporary or permanent storage of data, before, during or after acquisition of the data and/or after processing the data by the processor/controller unit 38.

While the schematic configuration of the system 32 of FIG. 4 illustrates the general functional blocks of the system of the present invention, many different specific implementations of the system may be used for different applications. Some exemplary specific implementations of the system 32 are disclosed in detail hereinbelow for the specific application of performing pressure intraluminal blood pressure measurements by using a passive ultrasonic sensor implanted in the lumen of a blood vessel. However, many other permutation and combinations of the systems disclosed herein may be implemented for different applications or for the same specific application disclosed herein, as will be appreciated by the person skilled in the art.

Figure 5:
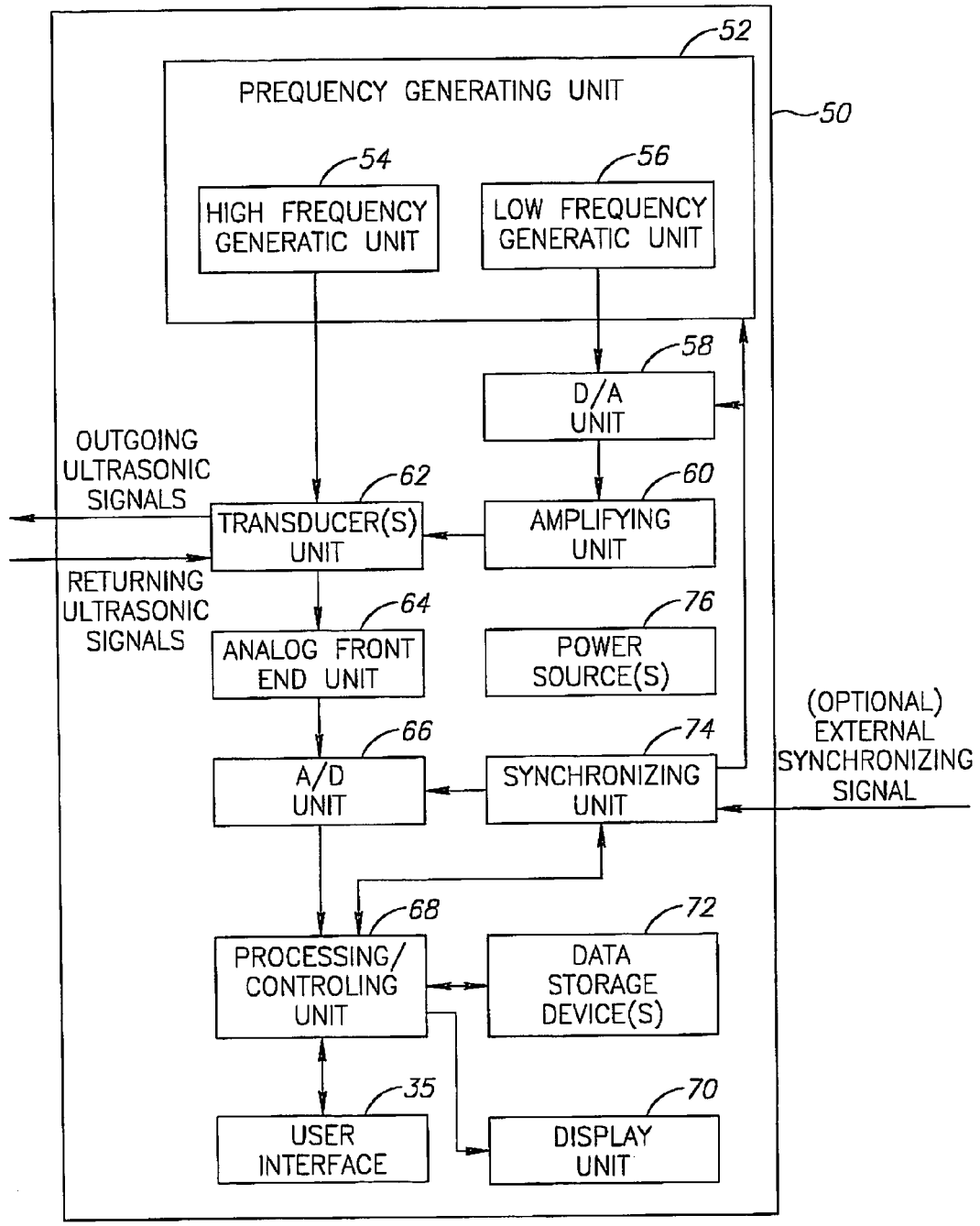
FIG. 5 is a schematic block diagram illustrating a system using the Doppler method for pressure measurements with passive ultrasonic sensors, in accordance with an embodiment of the present invention.

Reference is now made to FIG. 5 which is a schematic block diagram illustrating a system useful for determining the intraluminal blood pressure within a blood vessel by using an implanted resonating sensor, in accordance with one embodiment of the Doppler measurement method of the present invention.

The system 50 includes a transducer(s) unit 62 for producing outgoing signals in the form of an interrogating ultrasonic beam that may be directed at a passive resonating ultrasonic sensor (not shown in FIG. 5). The transducer(s) unit 62 is also used for receiving the signals returning from the sensor when the sensor is interrogated with the interrogating ultrasound beam. The transducer unit 62 may include one or more transducers (not shown separately in FIG. 5, for the sake of clarity of illustration). The transducer(s) included in the transducer unit 62 may be any transducer(s) suitable for controllably generating ultrasonic energy beams (such as, but not limited to sonic or ultrasonic beams) as is known in the art. For example, the transducer unit 34 may be implemented using suitable piezoelectric transducers, but any other type of transducer known in the art may be used as disclosed in detail hereinabove.

In accordance with one embodiment of the present invention, the transducer(s) unit 62 may include a single broadband ultrasonic transducer (not shown in detail in FIG. 5) capable of generating sufficient ultrasonic energy at the required sensor-excitation low frequency (or frequencies) and at the higher ultrasonic carrier frequency and of receiving returning ultrasonic signals to generate an electrical signal representing the received returning ultrasonic signal.

Alternatively, in accordance with another embodiment of the present invention, the transducer(s) unit 62 may include a plurality of ultrasonic transducers (not shown in detail in FIG. 5, but see FIG. 6 below) one or more of the plurality of transducers may be configured for generating sufficient ultrasonic energy at the required sensor-excitation low frequency (or frequencies) while other transducer(s) may be configured for generating the higher ultrasonic carrier frequency. The returning ultrasonic signal may be received by one or more of the transducer(s) included in the transducer(s) unit 62.

Generally, in accordance with one embodiment of the present invention, the transducer(s) used for generating ultrasonic frequencies may also be used for receiving or detecting the returning ultrasonic signal. Alternatively, in accordance with another embodiment of the present invention, it is also possible to use one or more dedicated ultrasonic transducers solely for receiving returned signals. All such permutations of transducer combinations may be used in the system of the present invention, as is known in the art, provided that they yield sufficient energy at the required frequencies and that they provide an acceptable signal to noise ratio for the received signals to allow performing the analysis of the signals as described in detail hereinafter.

The transducer(s) unit 62 may include any suitable ultrasonic transducer type or types. For Example, the ultrasonic transducer or transducers included in the transducer(s) unit 62, may be piezoelectric transducers, and/or capacitive ultrasonic transducers, and/or wideband capacitive transducers, and/or electromechanical transducers, and/or electromagneto-mechanical (coil and magnet based) transducers, or any other type of suitable ultrasonic transducer known in the art. Combinations of different types of ultrasonic transducers within the transducer(s) unit 62 may also be implemented. Composite transducers, and/or phased array transducers with steerable beams, and/or focusable beam composite transducers may also be used in implementing the present invention.

The system 50 may include a frequency generating unit 52 which is suitably coupled to the transducer(s) of the transducer(s) unit 62. The frequency generating unit 52 may include a high frequency signal generating unit 54 for generating a carrier frequency, and a low frequency generating unit 56 for generating low exciting frequencies for exciting the resonant sensor. The low frequency generating unit 56 may (optionally) be a digital frequency generator unit that may be suitably coupled to the transducer(s) unit 62 through a suitable digital to analog converter (D/A) unit 58 and an amplifying unit 60. Preferably (but not obligatorily), the low frequency generating unit 56 may be implemented as a digital signal processor (DSP) or any other suitable digital device or processor or microprocessor capable of providing a suitable digital frequency signal. However, any other suitable configuration for a low frequency generating unit known in the art (analog, digital or hybrid analog/digital) may also be used. The D/A unit 58 may be controlled by a suitable synchronizing unit 74 which may synchronize the operation of the D/A unit 58 with the sampling of the returning signals, as disclosed in detail hereinbelow.

The high frequency generating unit 54 may be a precision high frequency oscillator circuit suitably coupled to a transducer (not shown individually in FIG. 5) included in the transducer(s) unit 62. However, any other suitable type of frequency generator unit known in the art and capable of providing a suitable carrier frequency with a sufficient precision and sufficiently low spurious frequency content may be used.

The system 50 may also include an analog front end (AFE) unit 64 suitably coupled to the transducer (not shown individually within the transducer(s) unit 62) which transducer is used for receiving the ultrasonic signal returning from the interrogated resonating pressure sensor (not shown in FIG. 5) and for providing an electrical signal proportional to the returning ultrasonic wave signal.

The (optional) AFE unit may receive the analog signal from the transducer, and may process the signal in order to increase the signal to noise ratio and to selectively amplify the Doppler effect side bands frequencies as is disclosed in detail hereinafter to provide an analog conditioned signal. The AFE unit 64 may be suitably connected to an analog to digital converting (A/D) unit 66, and may feed the conditioned analog signal to the A/D unit 66 for digitizing. The A/D unit 66 may be suitably connected to a processing/controlling unit 68 and may feed the digitized signal to the processing/controlling unit 68 for further processing and analysis. The A/D unit 66 may be suitably connected to the synchronizing unit 74 and may receive synchronization signals from the synchronizing unit 74.

The processing/controlling unit 68 may be a processor unit, a microprocessor unit, a digital signal processor (DSP) unit, a controller unit, a computer including but not limited to any computer or interlined computers as disclosed hereinabove (with respect to FIG. 4) or any suitable combinations thereof. Any suitable controlling or processing unit(s) known in the art may be used.

The processing/controlling unit 68 may be suitably connected to (or may include) a user interface 35 for enabling input and/or output for user or operator interaction, as disclosed in detail with respect to FIG. 4 above.

The processing/controlling unit 68 may be suitably connected to one or more data storage device(s) 72 for storing data and recording and/or storing results. The data storage device(s) 72, may be any suitable type of storage device or combinations of storage devices known in the art, such as, but not limited to, solid state memory devices, including, but not limited to, random access memory (RAM), FLASH memory, DRAM, SRAM memory devices), magnetic storage device(s) (including, but not limited to fixed magnetic hard drives or removable magnetic media based drives, magneto-optical storage devices, or any other suitable type of storage device known in the art, and any combinations of fixed or removable storage devices.

The synchronizing unit 74 may be used to provide suitable triggering signals to the D/A unit 58 and to the A/D unit 66, in order to coordinate the operation of the D/A unit 58 and the A/D unit 66 in cases when the ultrasonic beam generated by the transducer(s) unit 62 is operated in a pulsed or burst mode or in a chirped mode. The synchronizing unit 74 may also be (optionally) suitably connected to the frequency generating unit 52, and may provide synchronizing or trigger signals for controlling the operation of the high frequency generating unit 54.

The system 50 may also (optionally) include a power source 76 for energizing the components of the system 50. The power source 76 may be any suitable power source (external or internal to the system 50) and may include one or more sources of DC and/or AC power sources as is known in the art, such as, but not limited to, mains power, DC power sources such as but not limited to primary batteries, rechargeable batteries, or the like, regulated or non regulated DC power sources, or the like).

The system 50 may also include a suitable display device 70 suitably connected to the processing/controlling unit 68 for displaying data or processed data or measurement results in numeric and/or alphanumeric and/or graphical or pictorial forms, or in any other presentation type or format known n in the art.

Figure 6:
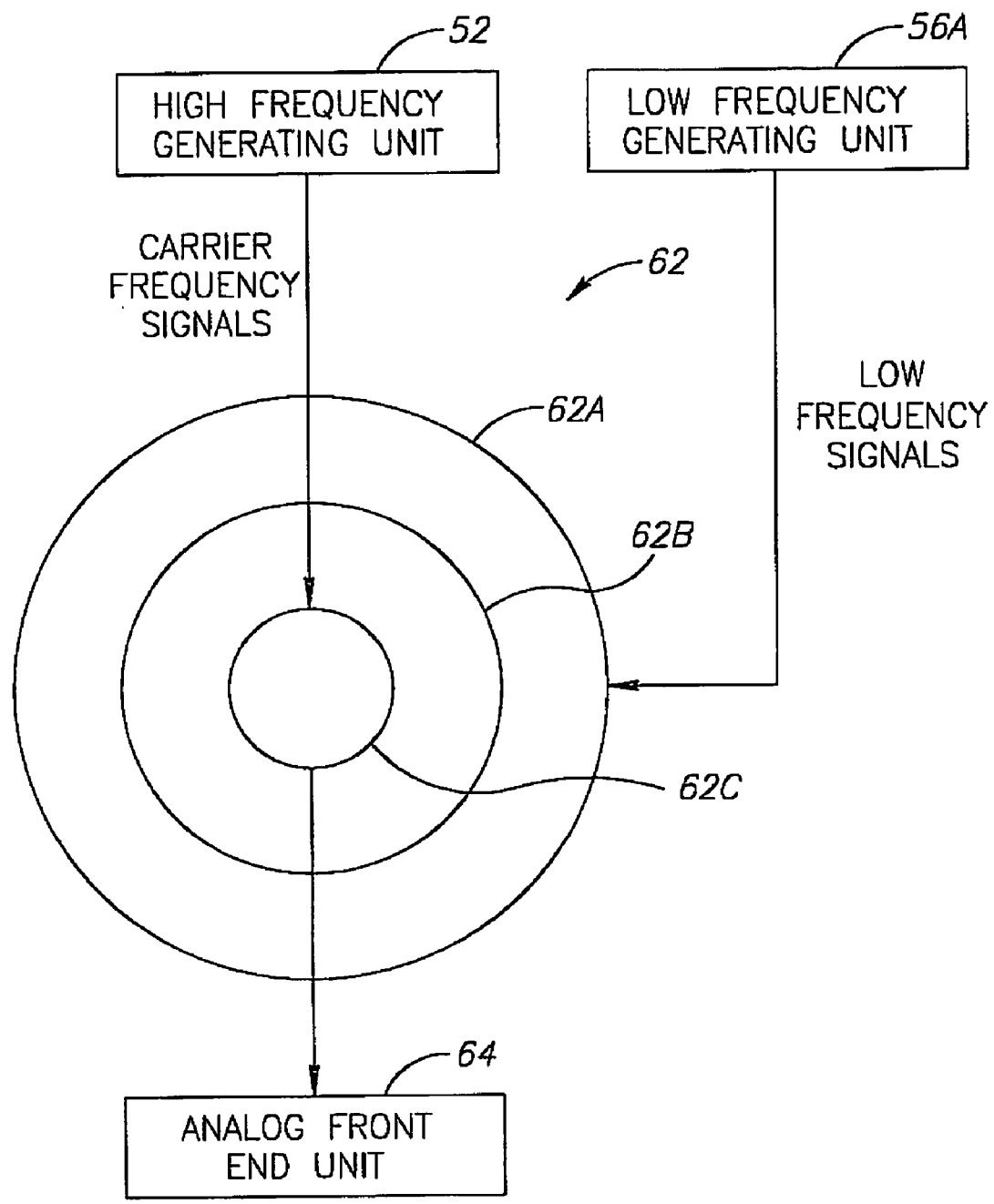
FIG. 6 is part block diagram and part schematic front view illustrating in detail a transducer(s) unit usable with the ultrasonic systems of FIGS. 4 and 5, in accordance with an embodiment of the present invention.

Reference is now made to FIG. 6 which is part block diagram and part schematic front view illustrating in detail a piezoelectric ultrasonic transducers unit usable with an ultrasonic system (such as, for example, the system 32 of FIG. 4, and the system 50 of FIG. 5), in accordance with an embodiment of the present invention.

The transducer(s) unit 62 is implemented as a multi-unit transducer including three concentric piezoelectric transducers. The transducer(s) unit 62 includes an annular low frequency transmitting transducer 62A that is suitably coupled to a low frequency generating unit 56A. The low frequency transmitting transducer 62A was an annular low frequency piezoelectric transducer having a working range of 50–100 KHz. The transducer was supplied with an impedance matching circuit. It is, however, noted that any other suitable low frequency transducer known in the art may be used for implementing the invention.

The transducer(s) unit 62 also includes an annular high frequency transmitting transducer 62B that is suitably coupled to the high frequency generating unit 52. The high frequency generating unit 52 generates the carrier frequency. In accordance with one embodiment of the present invention, the high frequency generating unit 52 is implemented as a low noise frequency generator unit designed to generate a carrier frequency at 2.5 MHz. The high frequency transmitting transducer 62B is adapted for emitting an ultrasonic beam at a frequency of 2.5 MHz.

It is, however, noted that other different values of the carrier frequency may also be used in implementing the present invention.

The transducer(s) unit 62 also includes a disc-like high frequency receiving piezoelectric transducer 62C that is suitably coupled to the analog front end unit 64.

The annular high frequency transmitting transducer 62B and the disc-like high frequency receiving piezoelectric transducer 62C were implemented as a 2.5 Mhz model CLI 7900 general-purpose ultrasonic probe, commercially available from Capistrano Labs, Inc., San Clemente, Calif., USA.

When the ultrasound beam including the resonator exciting low frequency (or frequencies) and the high carrier frequency is directed at the resonating sensor, the high frequency receiving piezoelectric transducer 62C receives the signal returning from the sensor as well as a other signal that returning from other objects and interfaces within the measurement environment, and generates an electrical signal representative of the returning signal. The electrical signal produced by the transducer 62C is fed into the AFE 64 for further processing.

In accordance with an embodiment of the present invention, the disc-like transducer 62C is coaxially nested within the annular transducer 62B and the annular transducer 62B is coaxially nested within the annular transducer 62A. It is however noted that this nested transducer arrangement is not obligatory and the invention may be implemented using any suitable transducer arrangement or type, as is known in the art.

It is noted that while in accordance with the system embodiment illustrated FIG. 5 the low frequency signals generating unit 56 was coupled to the low frequency transducer of the transducer(s) unit 62 through a D/A unit 58 and an amplifier unit 60 for providing the low frequency transducer with an amplified voltage signal other configurations may be used for generating the low frequency signals.

For example, in accordance with one embodiment of the present invention, the low frequency generating unit 56A was implemented by synthesizing low frequency signals on a model TE-5300 Arbitrary Waveform Generator PCI Card (not shown), commercially available from TABOR Electronics Ltd., Israel. The Arbitrary Waveform Generator PCI Card was installed on a personal computer (PC) (not shown). The synthesized low frequency signals were fed into a model L8666 low pass filter (not shown), commercially available from Anatech Electronics Inc., USA, for filtering out high frequencies. The filtered signal was then fed into an impedance matching circuit (not shown) suitably connected to the low frequency transmitting transducer 62A. The impedance-matching circuit was supplied by Ethalon with the low frequency piezoelectric transducer. It will be appreciated by those skilled in the art that the above disclosed implementation of the low frequency generating unit is given by way of example only, and the invention may easily be implemented using any other suitable circuit or device known in the art for generation of the low frequencies used by the system of the invention.

As described hereinabove, the returning signal received by the transducer(s) unit 62 may include the modulated signal reflected from the vibrating membranes of the sensor, and high frequency echoes reflected from various tissues and tissue interfaces and from the non vibrating parts of the sensor.

The modulated signal may be regarded as a frequency modulated (FM) signal. Since the modulation index $\beta$ is very low ($\beta$<0.1), the modulated signal may be treated as a narrow band FM signal. In narrow band FM there are only two significant sidebands containing most of the modulation energy. It may therefore be possible to use digital Fourier transform (DFT) analysis in order to estimate the energy at the specific frequencies without demodulating the received FM signal.

Two different methods may be used for receiving and processing the FM signal. The first method may use a base-band (BB) receiver that implements down-conversion of the center frequency to base-band (DC) as is known in the art. The second method may use an intermediate frequency (IF) receiver that implements down-conversion of the center frequency to a lower intermediate frequency (such as, for example, to a frequency of 500 KHz in the non-limiting exemplary implementation shown in FIG. 7A below), as is known in the art.

Thus, the AFE 64 of FIG. 5 may use a combination of a low noise amplifier and one or more suitable filter circuits to filter and amplify the low level signal received from the receiving transducer unit 62. The amplifier and other filters circuits used may set the noise figure of the receiving sub-system.

After the signal is filtered and amplified, a suitable mixer and a low pass filter may be used to perform down conversion of the signal, as is known in the art, to move the side frequencies which were around the high frequency (which may be 3.0 MHz in the specific, non-limiting, example of the high frequency generating unit 52 of FIG. 6) to lower intermediate frequencies. For example, the lower frequencies may be frequencies around 0.5 MHz if an IF receiver is used, or may be frequencies around the baseband (around DC level) if a base band (BB) receiver is used.

The down-conversion may be achieved by multiplying (mixing) the amplified and filtered received signal with a reference signal. For an IF receiver this reference signal is typically a pure sine wave Sin(wt), wherein w is equal to the transmitted carrier frequency. For example, this reference signal may be a pure CW signal with a frequency difference of +0.5 MHz or –0.5 MHz relative to the frequency of the carrier wave used in the transmitted ultrasonic beam.

The mixer output may be low pass filtered to attenuate any mixer generated spurious signals. For example, if the carrier frequency is 3.0 MHz and the reference signal fed to the mixer is at 2.5 MHz, the low pass filter cut-off frequency may be about 800 KHz. After such filtration, the signal mainly includes the new (down-converted) carrier frequency, the echoes of the high carrier frequency which were down-converted from high frequency (about 3.0 MHz) to about 0.5 MHz, and the side frequencies (the Doppler shifted frequencies) around the main down-converted carrier frequency.

Since the amplitude of the high frequency component at IF (composed mainly of down-converted echoes and the down converted carrier) may be significantly larger than the amplitude of the side band frequencies (typically, by more than 40–80 dB), and in order to improve the A/D dynamic range, a notch filter (around the frequency of 0.5 MHz) may be used. The notch filter (see for example, the notch filter 92 of FIG. 7A below) may be designed to attenuate the IF center frequency by 40–50 dB without substantially attenuating the side band frequencies. Such a notch filter may significantly increase the dynamic range of the system. A high gain amplifier may then be used after the notch filter to increase the level and the signal to noise (SNR) of the side bands without getting into saturation.

If a BB receiver implementation is being used instead of an IF receiver implementation, the reference signal is exp (-jwt), wherein w is equal to the transmitted carrier frequency (for example, if the transmitted carrier frequency is 3.0 MHz, then w is also selected at 3.0 MHz). The reference signal may then be viewed as a combination of a cosine (I phase) and sine (Quadrature). This is also known in the art as an IQ receiver implementation, and the output of the mixer is at DC. The implementation of a BB receiver is well known in the art and is therefore not disclosed in detail hereinafter.

Briefly, following the mixer, the IQ receiver (not shown) may implement two channels, an "I" channel and a "Q" channel (cosine and sine, respectively). Each channel may use a low pass filter (LPF) and a high pass filter (HPF). For example, the cut-off frequency of the LPF may be around 0.5 MHz. The HPF may replace the notch filter of the IF implementation since the carrier component is at DC. The cut-off frequency of the HPF may be about 20 KHz with an attenuation of 40–50 dB at DC, but other suitable cut-off frequencies and attenuation values may also be used, as is known in the art of IQ receiver design. The rest of the IQ receiver may be implemented similar to the IF receiver except that dual channel implementation is used (a separate amplifier and A/D unit may be used for each channel of the I and Q channels).

Figure 7A:
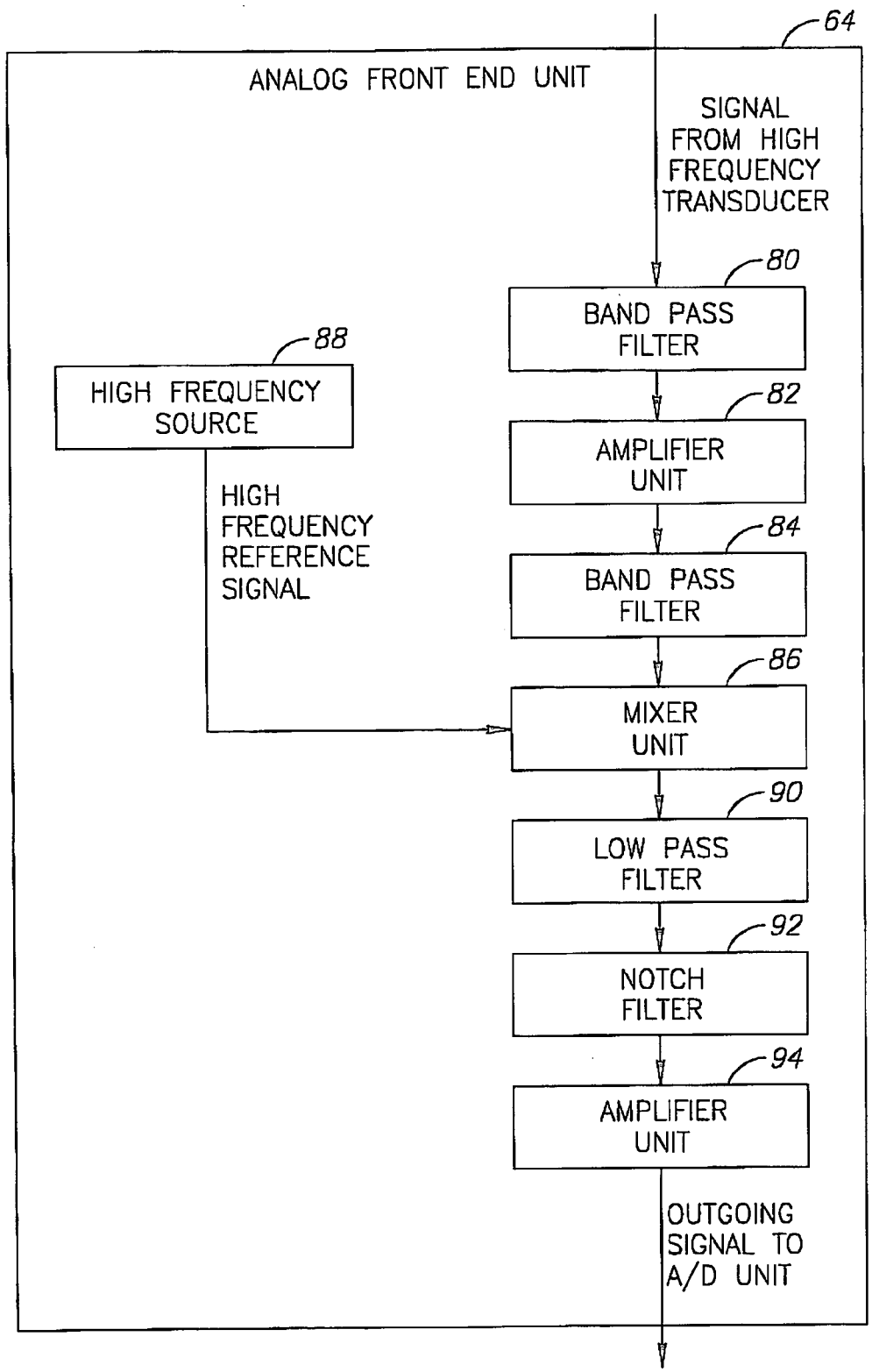
FIG. 7A is a schematic block diagram illustrating the components of an implementation of the analog front end unit illustrated in FIG. 5, in accordance with an embodiment of the present invention.
Figure 7B:
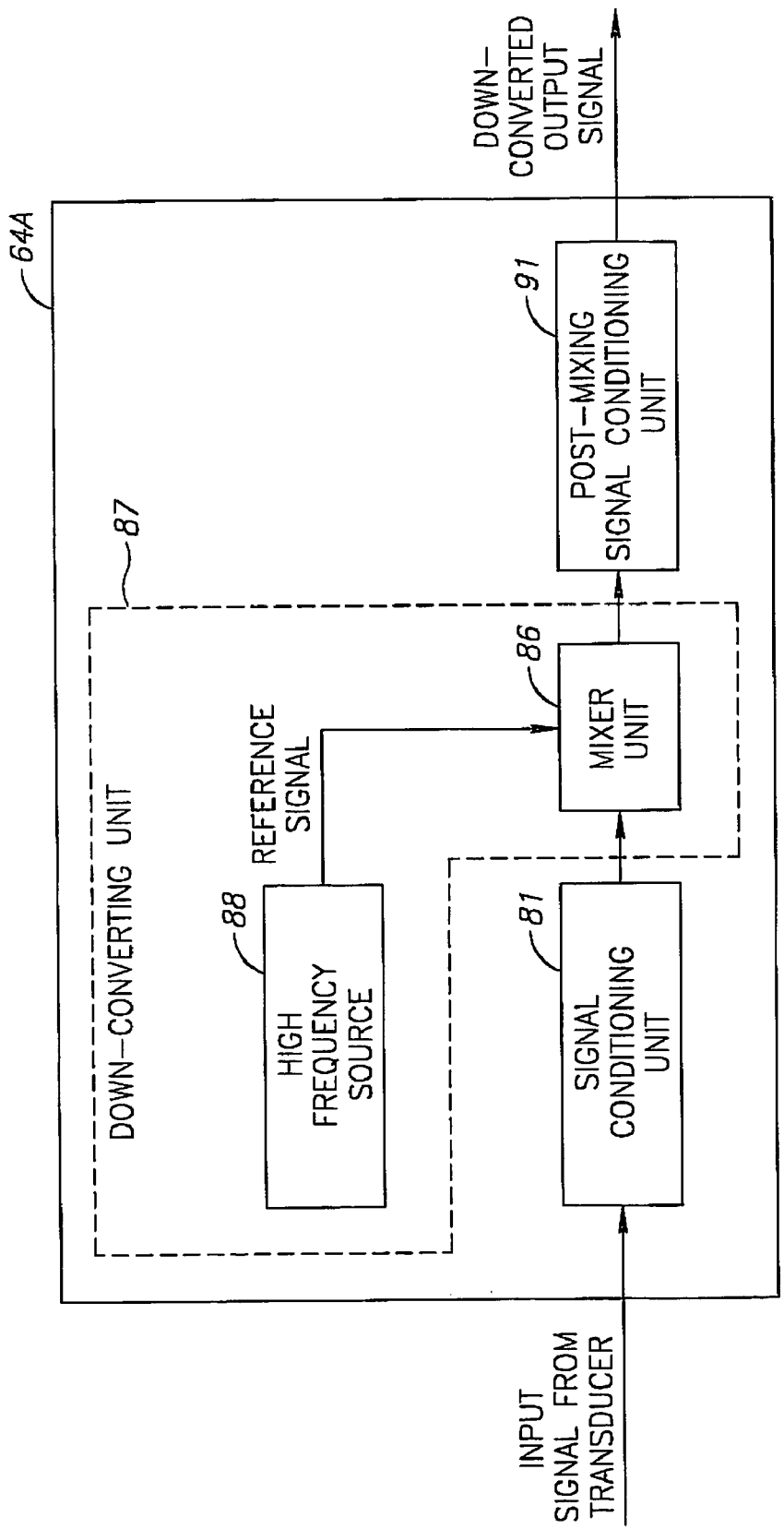
FIG. 7B is a schematic block diagram illustrating the components of a general implementation of an analog front end unit which may be used in the systems of the present invention.

Reference is now made to FIGS. 7A and 7B. FIG. 7A is a schematic block diagram illustrating of the components of an implementation of the analog front end unit illustrated in FIG. 5, in accordance with one possible embodiment of the present invention.

FIG. 7B is a schematic block diagram illustrating the components of a general implementation of an analog front end unit which may be used in the systems of the present invention.

The analog front end unit 64 used in the experiments disclosed hereinafter was based on an IF receiver implementation. The analog front end unit 64 includes a first bandpass filter (BPF) 80. The BPF 80 receives as input the electrical signal from the transducer included in the transducer(s) unit 62 (of FIG. 5) and filters the incoming signal passing signal frequencies in the range of 2.5–3.5 MHz while attenuating other frequencies for reducing low frequencies and noise. The BPF 80 was implemented by using the B6734 band pass filter commercially available from Anatech Electronics Inc., USA, but any other suitable BPF may be used.

The AFE unit 64 also includes a first amplifier 82 connected to the BPF 80 to amplify the filtered signal output of the BPF 80. The first amplifier 82 was implemented by using a model MCL ZFL-500LN amplifier or MCL ZFL-1000 amplifier commercially available from Mini Circuits® Laboratory, Brooklyn, USA. However, any other type of suitable low noise amplifier may be used.

The amplified signal from the amplifier 82 is fed to a second band pass filter 84 suitably connected to the amplifier 82. The second band pass filter 84 lowers the noise at 2.0 MHz which folds back after the mixer unit 86 included in the AFE unit 64. The second BPF 84 was implemented by using the model B6734 band pass filter described above, but any other suitable BPF may be used.

The output of the second BPF 84 is fed into a mixer unit 86. The mixer unit 86 was implemented as a model MCL ZP-3 MH mixer commercially available from Mini Circuits® Laboratory, USA. However, any other suitable mixer unit known in the art may be also used. The Mixer unit 86 is also connected to a high frequency source 88. The high frequency source was implemented as a low noise high frequency source generating a frequency of 2.5 MHz. The mixer unit 86 multiplies the 2.5 MHz signal provided by the high frequency source 88 by the signal received from the band pass filter 84. The mixer unit 86 is connected to a low pass filter 90 which filters the output signal of the mixer unit 86 to remove the high signal frequencies around 5.5 MHz while passing the down converted frequencies around 0.5 MHz. The LPF 90 was implemented as a model L8666 low pass filter commercially available from Anatech Electronics Inc., USA., but any other suitable LPF may be used.

The output of the low pass filter 90 is connected to a notch filter 92. The notch filter 92 is configured for attenuating the amplitude of the down converted carrier signal at about 0.5 MHz without substantially attenuating the down converted side band frequencies. The notch filter was implemented as a model S2034 notch filter commercially available from Anatech Electronics Inc., USA., but any other suitable notch filter may be used.

An amplifier unit 94 is connected to the notch filter 92 for amplifying the output of the notch filter 92. The second amplifier unit 94 was implemented as a model MCL ZFL-500LN amplifier, commercially available from Mini Circuits® Laboratory, USA. Since the notch filter 92 decreases the amplitude of the down converted carrier frequency component at 0.5 MHz without substantially affecting the amplitude of the down converted side band frequencies, the side bands may be suitably amplified without undue saturation of the amplifier unit 94, improving the dynamic range of the system.

The output signal of the amplifier unit 94 may be digitized by a suitable digitizing unit, such as, for example by the A/D unit 66 (of FIG. 5), or by any other suitable digitizing unit known in the art.

Turning to FIG. 7B, in a more general implementation of the analog front end of the present invention, the AFE 64A may include a signal conditioning unit 81. The signal conditioning unit 81 may receive the analog signal from the receiver unit 39 (of FIG. 4), or the analog signal from the transducer(s) unit 62 (of FIG. 5) and may condition the signal by performing suitable filtration and/or amplification of the analog signal in order to remove undesired frequency components from the analog signal and to suitably amplify the signal if necessary. The conditioned signal from the signal conditioning unit 81 may be fed to a down converting unit 87 connected to the signal conditioning unit 81. The down converting unit 87 may include a high frequency source 88, suitably connected to a mixer unit 86 (as disclosed hereinabove for the AFE unit 64 of FIG. 7A).

The mixer unit is fed a high frequency reference signal from the high frequency source 88, as disclosed hereinabove. The mixer unit 86 may mix the conditioned signal provided by the signal conditioning unit 81 with the reference signal to provide a mixed signal. The frequency of the reference signal may depend on the carrier frequency used in interrogating the sensor and on the method of implementing the down converting (such as, for example, BB or IF down conversion methods). The AFE 64A may also include a post-mixing signal conditioning unit 91. The post-mixing signal conditioning unit 91 may be implemented using any method known in the art to remove undesired frequency components of the down converted signal, as is known in the art. Typically, various combinations of filter circuits (including, but not limited to, band pass filters, and/or Notch filters, and/or low pass filters, and or/high pass filters with or without amplifier circuits) may be used to implement the signal conditioning unit 81 and the post mixing signal conditioning unit 91 of FIG. 7A.

It is noted that, in the specific implementation of the AFE 64 illustrated in FIG. 7A and disclosed in detail hereinabove, the post-mixing signal conditioning unit is implemented by the low pass filter 90, the notch filter 92 and the amplifier unit 94. Similarly, the signal conditioning unit 81 was implemented by using the band pass filter 80, the amplifier unit 82 and the band pass filter 84. However, many other different implementations and circuit designs may be used in implementing the signal conditioning unit 81 and the post-mixing signal conditioning unit 91 depending, inter alia, on the specific values of the carrier frequency and the sensor exciting frequencies used, the down-conversion method used (BB or IF methods), and the specific noise levels and the typical returning signal intensity and/or other signal parameters of the particular application.

It is noted that the use of the AFE unit 64 (implemented either with an Intermediate Frequency receiver as shown in FIG. 7A or with an IQ baseband receiver) is not mandatory for implementing the system of the present invention. The exemplary embodiments disclosed and illustrated hereinabove were found practical for measuring the amplitude of the Doppler shifted sidebands in experimental situations in which the amplitude of the central carrier frequency is about five orders of magnitude larger than the amplitude of the side bands.

It is, however, noticed that if the A/D unit 66 is implemented as a low noise digitizer having a sufficiently high dynamic range (for example, by using a suitable low noise 32 bit A/D unit), the AFE unit 64 may become redundant and the output signal of the receiving transducer 62C may be directly fed to the Processing/controlling unit 68 (of FIG. 5) for further processing as disclosed in detail hereinafter. While such low noise high dynamic range A/D units may be rather expensive to implement, they are well known in the art, and may therefore be (optionally) used in implementing the present invention, to obviate the need for an analog front end unit.

If one uses such a low noise high dynamic range A/D unit to implement the A/D unit 66, the AFE unit 64 may be eliminated and the returning voltage signal output by the transducer(s) unit 62 may be directly fed to the A/D unit, and the resulting digitized signal may then be processed by the processing/controlling unit 68. Any necessary filtering or other processing steps (such as, but not limited to, normalization or multiplication by a suitable window) may then be performed by suitable software implemented on the processing/controlling unit 68, as is known in the art.

In such a case (using the low noise high dynamic range A/D converter), it may be possible to determine the amplitude of the Doppler shifted sideband frequencies directly from the digital signal without having to perform a down converting procedure, provided that the amplitude(s) of the sideband frequencies are above the noise level of the digitized signal. The digitized signal may be subjected to various digital filtration and/or other digital signal conditioning and/or digital signal amplification methods, if necessary, as is known in the art of digital signal processing.

In accordance with a preferred embodiment of the present invention, the processing/controlling unit 68 analyzes the digitized signal received from the A/D unit 66 by performing a digital Fourier transform (DFT) on the signal to provide a frequency domain data representation of the digitized signal. Prior to performing the DFT, the digitized data may be multiplied by a suitable window function (such as, for example, a Hamming window or a Hanning window, but any other types of suitable window functions such as, but not limited to, suitable Harris-Blackman window functions may be also used, as is known in the art) for reducing "bin leakage" due to the finite length of the sampling duration, as is known in the art. The type of window function used may depend, inter alia, on the sampling duration used by the system, and the window function procedure is optional. The frequency domain data may then be further analyzed to determine the amplitude of the side band frequency or frequencies as disclosed in detail hereinafter.

Figure 8:
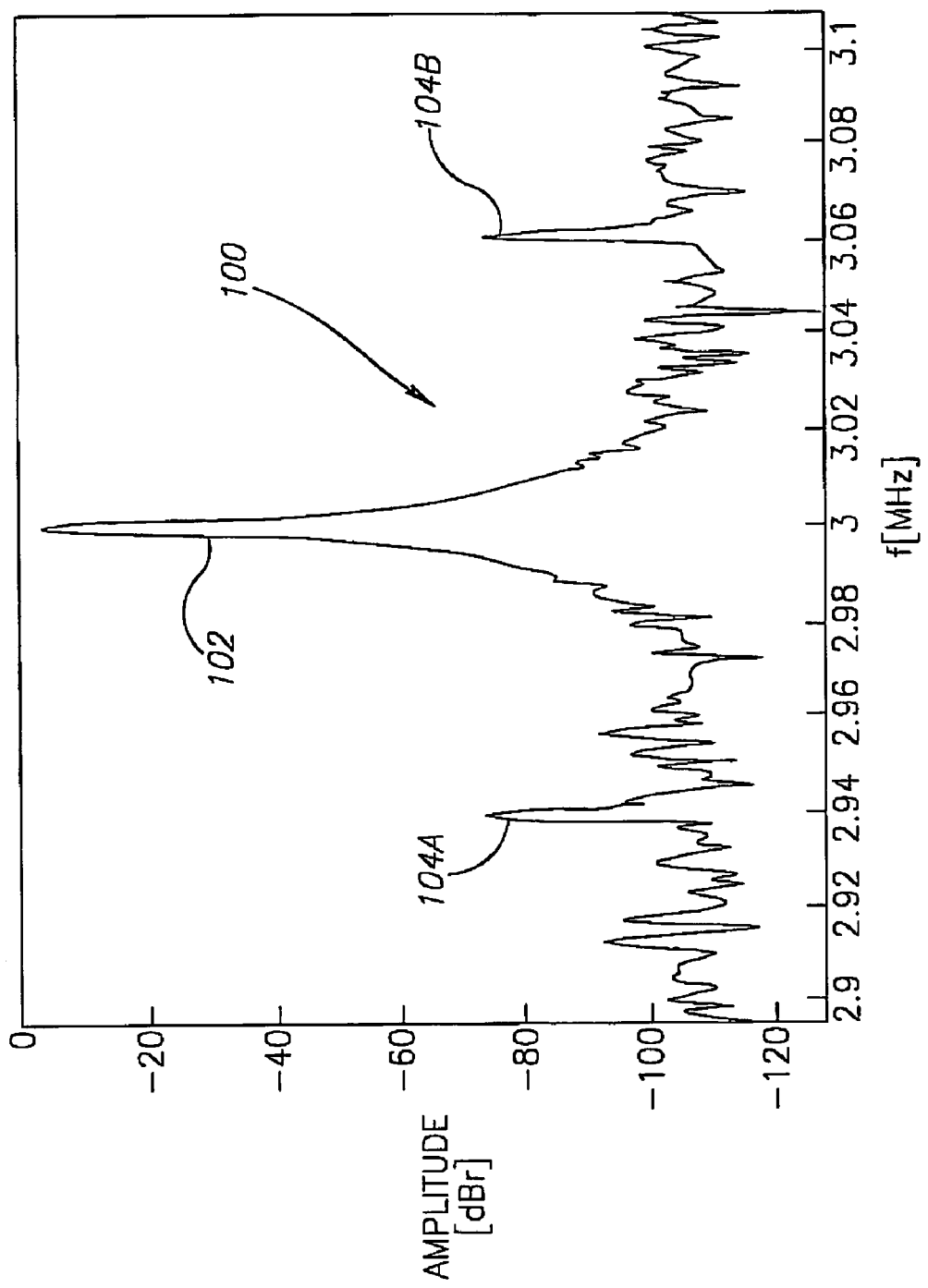
FIG. 8 is a schematic graph illustrating an example of frequency domain data obtained from experiments using the sensor 20 of FIG. 2 by using the Doppler measurement method of the present invention.

Reference is now made to FIG. 8 which is a graph illustrating an example of frequency domain data obtained from experiments using the sensor 20 of FIG. 2 by using the Doppler measurement method of the present invention.

The frequency domain data of FIG. 8 was obtained using an ultrasonic system similar to the system 50 of FIG. 5, and the sensor 20 of FIGS. 2–3. The system used a carrier frequency of 3 MHz and a sensor exciting frequency between of 61 KHz. The experiment was performed by placing the sensor 20 in a controlled pressure vessel filled with water (not shown) and directing an ultrasonic beam containing a carrier frequency of 3.0 MHz and a single sensor exciting frequency of 61 KHz at the sensor 20. The low frequency 61 KHz signal was produced by MATLAB® software and output as an analog output by a CG1100 D/A unit, commercially available from Gage Technologies Inc., USA. The analog signal was amplified by a model 75A250 amplifier, commercially available from Amplifier Research Inc., USA. A model AFG320 function generator, commercially available from Tektronics Inc., USA, was used to produce the high frequency signal at 3 MHz, which was used to drive the CLI Ultra Sound board from Capistrano Labs Inc., USA. The CLI Ultrasound board sent the signal to the high frequency transducer.

The returning signals were sampled at a sampling rate of 50 MHz by a model PDA12 board from Signatech Inc., USA and were processed and analyzed using MATLAB® software. The curve 100 of the graph of FIG. 8 represents the frequency domain data obtained after performing DFT on a time domain data sequence.

The vertical axis of the graph illustrated in FIG. 8 represents the signal amplitude (in dBr) and the horizontal axis represents the frequency (in MHz). The central peak 102 represents the carrier signal (centered at about 3.0 MH) and the two peaks 104A and 104B are the two sidebands representing the Doppler shifted frequencies at 3.0 MHz±61 KHz due to the modulation of the 3.0 Mhz carrier frequency by the vibratable membranes vibratable membranes 29A, 29B, 29C, 29D, 29E, 29F, 29G, 29H, and 29I of the sensor 20 which were vibrating at the sensor exciting frequency of 61 KHz. It is noted that the carrier frequency peak 102 and the sideband frequencies 104A and 104B are well above the noise level. It may be clearly seen that the amplitude of the carrier frequency echo peak 102 is much higher than the amplitude of sideband frequencies, (the amplitude differ by about 60 dB). Still, the side frequencies may be accurately measured since they are significantly higher (by approximately 25 dB), than the average noise level. Thus, the amplitude of the sideband peaks may be determined from the frequency domain data by finding the maximum value in the data around the (known) Doppler shift frequencies.

Since the transmitted sensor exciting frequency value(s) are known, the amplitude of the Doppler shifted sidebands may be automatically determined from the acquired frequency domain data. Practically, the amplitude of the data point at the computed sideband frequency may be taken. For example, if the system transmitted a carrier frequency at 3.0 MHz and a sensor exciting frequency at 61 KHz, and the AFE 64 performed a down-conversion of the frequencies by 2.5 MHz (as disclosed in detail hereinabove), the system may simply record the amplitude at the frequencies of 0.5 MHz±61 KHz and use these amplitudes values as the approximate sideband amplitudes for further computations.

Similarly, in cases where a few sensor exciting frequencies are transmitted simultaneously with the carrier frequency, the system may determine the amplitudes of the sideband frequencies for each sensor exciting frequency by determining the amplitudes at all the computed frequencies for all the relevant sidebands.

Alternatively, for each specific sensor exciting frequency transmitted, the system 32 or 50 may search for a maximum amplitude value within one or two defined frequency windows of the frequency domain data. Any suitable method may be used for finding the amplitude of a sideband peak. For example, in accordance with one embodiment of the present invention, the system may perform a "bubble sort" operation on a subset of the frequency domain data points which falls within a frequency window defined around the expected sideband frequency (based on knowledge of the sensor exciting frequency, as disclosed hereinabove) and take the maximum amplitude value of the data point subset within the selected frequency range.

For example, in the non-limiting exemplary frequency domain data illustrated in FIG. 8, the system may search for the highest amplitude value of all the data points within a frequency window around the peak 104A (for example, in the frequency window of 2.93 MHz–2.95 MHz, but other different frequency windows may also be used), or around the peak 104B (for example, in the frequency window of 3.05 MHz–3.07 MHz, but other different frequency windows may also be used). Alternatively, the system may determine the values of the maximal amplitude for both sideband peaks 104A and 104B using appropriate frequency windows and may store the values of the amplitudes of both sideband peaks for further processing as disclosed in detail hereinafter.

It is noted that other different suitable algorithms or methods may be used to determine the sideband peak amplitude as is known in the art.

If more than one sensor exciting frequency is simultaneously transmitted together with the carrier frequency (as is disclosed in detail hereinafter with respect to FIGS. 10 and 11), the system may similarly determine the sideband(s) amplitude associated with each specific sensor exciting frequency used, and may use one or more of the determined sideband peak amplitudes for further processing, as disclosed in detail hereinbelow.

When the frequency window method disclosed above is used for determining the amplitude of multiple sideband peaks resulting from simultaneous transmission of several sensor exciting frequencies together with the carrier frequency, the windows used should be narrow enough to ensure that any window will not include more than one sideband peak but is still wide enough to include the point with the maximal amplitude for the selected sideband peak.

In accordance with one embodiment of the present invention, for each specific sensor exciting frequency, the system may use the amplitude value of a single selected sideband peak. For example, in the specific exemplary frequency domain data illustrated in FIG. 8, the system may use either the value of the sideband peak 104A, or the value of the of the sideband peak 104B for further processing.

In accordance with another embodiment of the present invention, for each specific sensor exciting frequency, the system may use an averaging procedure to compute a mean amplitude value from the values of the amplitudes of both sidebands of each specific sensor exciting frequency. Two exemplary averaging methods are described below, but any other averaging methods known in the art may also be used in implementing the present invention.

In accordance with one possible embodiment of the present invention the system may simply use the arithmetic mean value of the two determined sideband peak amplitudes. For example, the system may compute the mean sideband amplitude for each specific transmitted sensor exciting frequency by using the following equation:

$$A_M = (A_L + A_H)/2$$

Wherein, $A_M$ is the mean sideband amplitude for a specific transmitted sensor exciting frequency;

$A_L$ is the amplitude of the sideband peak resulting from the specific sensor exciting frequency and having a frequency lower than the carrier frequency;

and $A_H$ is the amplitude of the sideband peak resulting from the specific sensor exciting frequency and having a frequency higher than the carrier frequency.

In the exemplary frequency domain data illustrated in FIG. 8, $A_M$ is the mean amplitude of the sideband peaks for the sensor excitation frequency of 61 KHz, $A_L$ is the amplitude of the sideband peak 104A and $A_H$ is the amplitude of the sideband peak 104B.

In accordance with another possible embodiment of the present invention the system may use the geometrical mean of the two determined sideband peak amplitudes. For example, the system may compute the geometrical mean ACM of the sideband amplitudes for each specific transmitted sensor exciting frequency by using the following equation:

$$A_{GM} = (A_L^2 + A_H^2)^{0.5}$$

Wherein, $A_{GM}$ is the geometrical mean of the sideband amplitudes for a specific transmitted sensor exciting frequency;

And $A_L$ and $A_H$ are as defined hereinabove.

It is noted that if the geometrical mean of the sideband amplitudes is used, the resulting mean amplitude value is biased towards the value of the sideband with the higher amplitude of the two sidebands.

It is noted that if there is some asymmetry in the construction of the sensor used (such as, for example, if the vibratable membranes 29A, 29B, 29C, 29D, 29E, 29F, 29G, 29H, and 29I of the sensor 20 differ in physical dimensions), the response of the sensor may be sensitive to the direction of the interrogating ultrasonic beam. In such a case of a sensor having a directionally asymmetrical response, the returning signal may exhibit a certain degree of amplitude modulation (AM) in addition to the frequency modulation (FM) disclosed hereinabove.

It was found empirically (as may also be predicted from theoretical considerations) that the use of the geometrical mean method may be preferred for reducing errors due to such asymmetry in the directional response of the sensor 20 (in comparison with the other methods for determining the sideband amplitude value disclosed hereinabove). However, the other methods disclosed hereinabove may also be used by working with sensors with minimal directional response asymmetry, or in cases were the error due to the asymmetry is acceptable.

Figure 9:
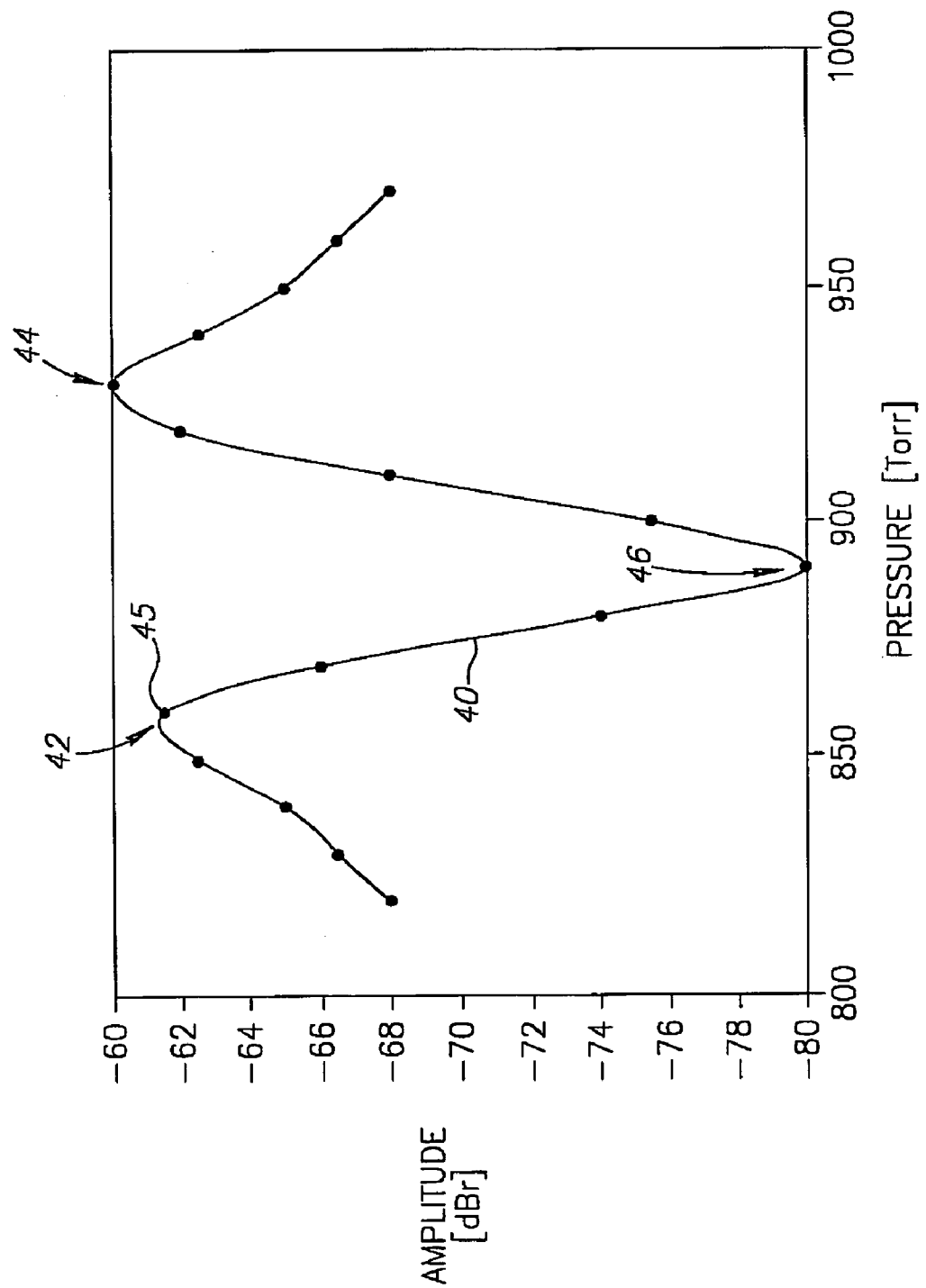
FIG. 9 is a schematic graph illustrating the dependence of the Doppler shifted sideband amplitude of the returning signal on the external pressure acting on a passive ultrasonic sensor excited by an interrogating ultrasound beam containing an exciting frequency of 61 KHz.

Reference is now made to FIG. 9 which is a schematic graph illustrating the dependence of the Doppler shifted sideband amplitude of the returning signal on the external pressure acting on a passive ultrasonic sensor excited by an interrogating ultrasound beam containing an exciting frequency of 61 KHz.

The experimental data illustrated in FIG. 9 was obtained by placing the sensor 20 illustrated in FIGS. 2 and 3 and disclosed in detail hereinabove in a pressure chamber filled with water, directing a beam of ultrasound including a carrier frequency of 3.0 MHz and a sensor exciting frequency of 61 KHz at the sensor, receiving an ultrasonic signal returning from the sensor 20 and processing the returning signal using DFT method to obtain frequency domain data (not shown) and determine the sideband amplitudes corresponding with each of the sensor exciting frequencies from the data The pressure inside the pressure chamber was changed and the same measurements were performed at different pressure values using the same group of sensor exciting ultrasound frequencies.

In the graph of FIG. 9, the horizontal axis represents the pressure acting on the sensor 20 (in Torricelli) and the vertical axis represents the mean amplitude of the two returning ultrasound signal sidebands (in dBr) of the frequency domain data.

The full circle symbols are the experimental data points representing the mean amplitude of the sideband corresponding to the exciting frequency of 61 KHZ. The data for the other frequencies used in the experiment is not shown (for the sake of clarity of illustration).

The curve 40 is obtained by polynomial curve fitting of the experimental data points taken at various pressure values. The curve 40 has two amplitude peaks 42 and 44 and an amplitude minimum point 46. The amplitude minimum point 46 represents the flipping point of the vibratable membranes 29A, 29B, 29C, 29D, 29E, 29F, 29G, 29H, and 29I of the sensor 20.

The amplitude peaks 42 and 44 occur at pressure values for which the sensor exciting frequency of 61 KHZ is equal to the resonance frequency of the vibratable membranes 29A, 29B, 29C, 29D, 29E, 29F, 29G, 29H, and 29I of the sensor 20. The amplitude peak 42 occurs at a pressure of approximately 858 Torriceli and the amplitude peak 44 occurs at a pressure of approximately 930 Torriceli. At these two pressure values the resonance frequency of the vibratable membranes 29A, 29B, 29C, 29D, 29E, 29F, 29G, 29H, and 29I of the sensor 20 is at or close to approximately 61 KHz.

It is noted that the experimental data point 45 does not lie exactly at the peak 42 of the fitted curve 40. This is because of the pressure values at which the experimental measurements were taken were arbitrarily chosen. However, the lowest pressure value (within the sensors' working pressure range) at which the vibratable membranes 29A, 29B, 29C, 29D, 29E, 29F, 29G, 29H, and 29I are at resonance for the frequency of 61 KHz may be determined by finding the pressure value at which the fitted curve 40 has the first peak 42.

It is noted that while the use of an interrogating beam including a carrier frequency and a single sensor exciting frequency is possible, it may also be possible, in accordance with another embodiment of the present invention, to use an ultrasound beam simultaneously including a plurality of different sensor exciting frequencies and the carrier frequency for measurement or calibration.

Figure 10:
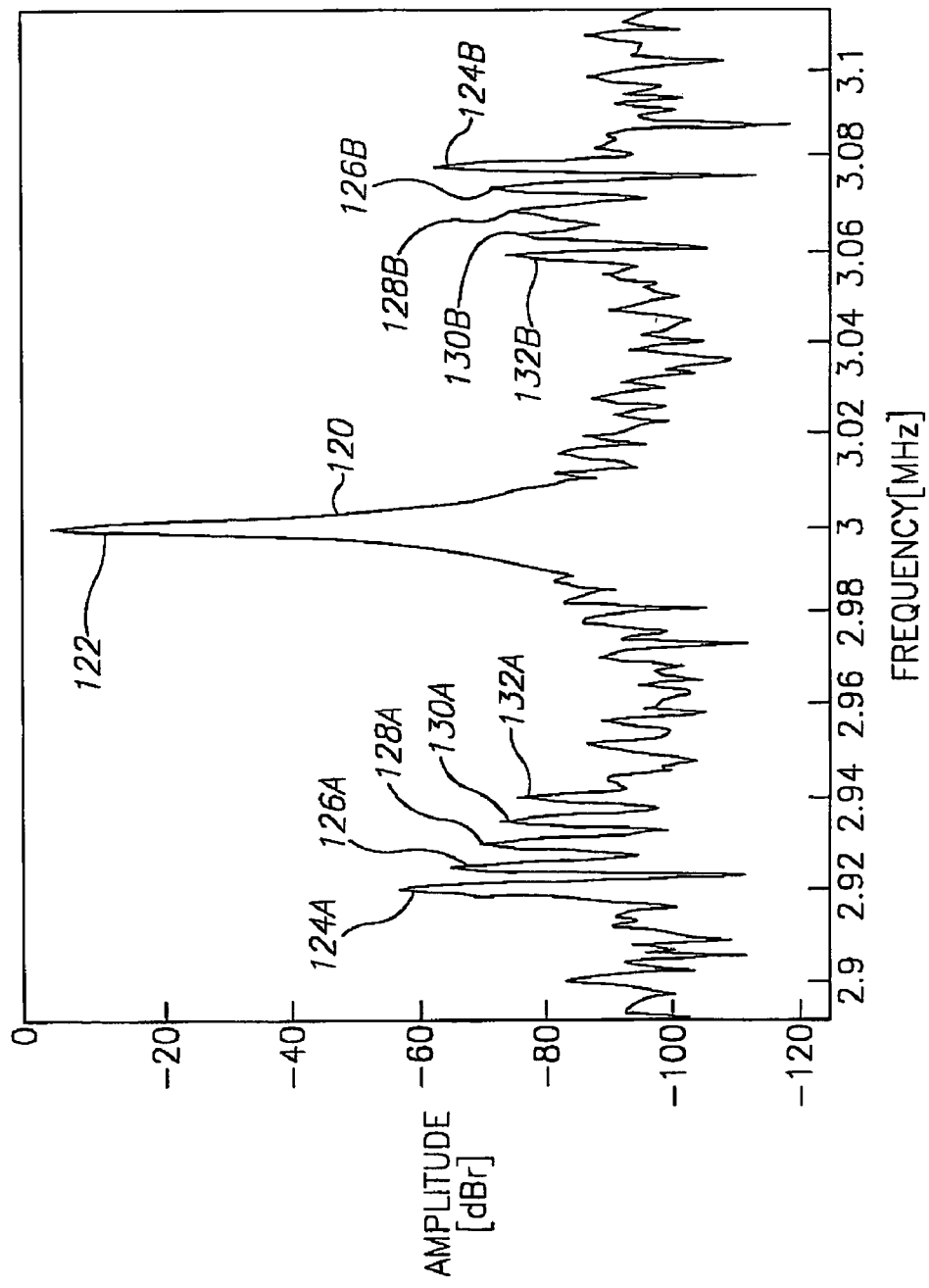
FIG. 10 is a graph illustrating an example of frequency domain data obtained from experiments using the sensor 20 of FIG. 2 by using the Doppler measurement method of the present invention and an ultrasound beam simultaneously including a carrier frequency and five different sensor exciting frequencies.
Figure 11:
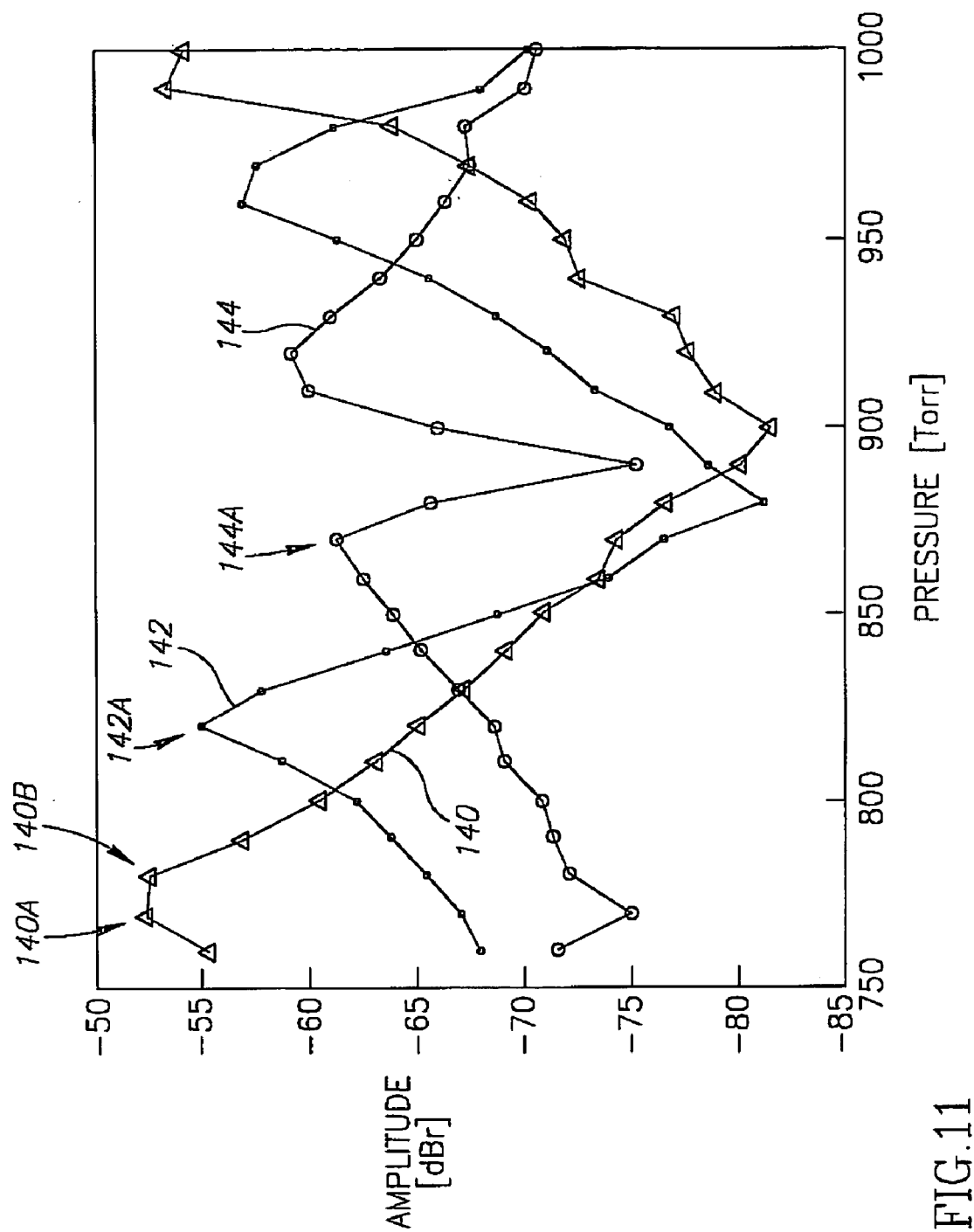
FIG. 11 is a schematic graph illustrating the dependence of the Doppler shifted sideband amplitude on the external pressure acting on a passive ultrasonic sensor for three different sensor exciting frequencies simultaneously transmitted in an ultrasound beam interrogating the sensor.

Reference is now made to FIGS. 10 and 11. FIG. 10 is a graph illustrating an example of frequency domain data obtained from experiments using the sensor 20 of FIG. 2 by using the Doppler measurement method of the present invention and an interrogating ultrasound beam simultaneously including a carrier frequency of 3.0 MHz and five different sensor exciting frequencies at 60 KHz, 65 KHz, 70 KHz, 75 KHz, and 80 KHz.

FIG. 11 is a schematic graph illustrating the dependence of the Doppler shifted sideband amplitude on the external pressure acting on a passive ultrasonic sensor for three different (exemplary) sensor exciting frequencies simultaneously transmitted in an ultrasound beam interrogating the sensor.

The vertical axis of the graph illustrated in FIG. 10 represents the signal amplitude (in dBr) and the horizontal axis represents the frequency (in MHz). The curve 120 represents the amplitude versus frequency data of the returning signal. The central peak 122 represents the carrier signal (centered at about 3.0 MHz). The pair of peaks 124A and 124B are the two sidebands representing the Doppler shifted frequencies at 3.0 MHz±80 KHz due to the modulation of the 3.0 Mhz carrier frequency by the vibratable membranes vibratable membranes 29A, 29B, 29C, 29D, 29E, 29F, 29G, 29H, and 29I of the sensor 20 which were vibrating at the sensor exciting frequency of 80 KHz.

Similarly, the pair of peaks 126A and 126B are the two sidebands representing the Doppler shifted frequencies at 3.0 MHz±75 KHz due to the modulation of the 3.0 Mhz carrier frequency by the vibratable membranes vibrating at the sensor exciting frequency of 75 KHz, the pair of peaks 128A and 128B are the two sidebands representing the Doppler shifted frequencies at 3.0 MHz±70 KHz due to the modulation of the 3.0 Mhz carrier frequency by the vibratable membranes vibrating at the sensor exciting frequency of 70 KHz, the pair of peaks 130A and 130B are the two sidebands representing the Doppler shifted frequencies at 3.0 MHz±65 KHz due to the modulation of the 3.0 Mhz carrier frequency by the vibratable membranes vibrating at the sensor exciting frequency of 65 KHz and the pair of peaks 132A and 132B are the two sidebands representing the Doppler shifted frequencies at 3.0 MHz±60 KHz due to the modulation of the 3.0 Mhz carrier frequency by the vibratable membranes vibrating at the sensor exciting frequency of 60 KHz.

It is noted that the carrier frequency peak 122 and the sideband frequency peaks 124A, 124B, 126A, 126B, 128A, 128B, 130A, 130B, 132A and 132B are all above the noise level and the amplitude of the sidebands may therefore be measured.

Turning to FIG. 11, the graph illustrates sideband amplitude versus external pressure determined for three sensor exciting frequencies of 60 KHz, 70 KHz and 80 KHz, simultaneously transmitted with a carrier frequency of 3.0 MHz in an interrogating beam directed at the sensor 20 of FIGS. 2–3, immersed in water in a controlled pressure chamber. The pressure values in the chamber were varied as disclosed in detail hereinabove. The vertical axis represents the sideband amplitude (in dBr) and the horizontal axis represents the pressure in the pressure chamber (in Torr).

The triangular symbols of the curve 140 represent the measured values of the sideband amplitude for the exciting frequency of 80 KHz at different experimental pressure values. The amplitudes were measured from frequency domain data as disclosed in detail hereinabove. The filled circular symbols of the curve 142 represent the measured values of the sideband amplitude for the exciting frequency of 70 KHz at different experimental pressure values, and the open circular symbols of the curve 144 represent the measured values of the sideband amplitude for the exciting frequency of 60 KHz at different experimental pressure values. In contrast to the curve 40 of FIG. 8 which represent a computed curve fitted to the experimental data points, the curves 140, 142 and 144 were formed by simply connecting the respective data points by straight lines. The curves 140, 142 and 144 are therefore raw data curves.

The experimental results illustrated in FIGS. 10 and 11 demonstrate that it is possible to use many sensor exciting frequencies simultaneously transmitted with the carrier frequency in the interrogating beam and to obtain the amplitudes of the resulting sidebands from the frequency domain data of the signal returning from the sensor, as long as the signal amplitude is not too high and the sensor's response is linear.

The simultaneous use of a few sensor exciting frequencies thus yields more information than the use of a single sensor exciting frequency. It is noted, however, that when several sensor exciting frequencies are simultaneously generated by the transducer, the amplitude of the transmitted signal at each of the transmitted exciting frequencies may be smaller than when the same transducer transmits a single exciting frequency. Thus, if the total beam energy is limited (as may be the case if the interrogating beam is operated near the maximal clinically allowed beam intensity at the specific frequencies used, when used in humans) the sideband amplitude of the received returning signal may also be smaller. It is further noted that when using simultaneous transmission of multiple sensor exciting frequencies one needs to verify that the sensor's response is still linear for the range of frequencies and pressures used.

The data of FIG. 11 clearly demonstrates that the sensor's resonance frequency changes with the external pressure. For example, the point 144A of the curve 144 indicates that the resonance frequency of the sensor is at approximately 60 KHz at an external pressure value of approximately 872 Torr. The point 142A of the curve 142 indicates that the resonance frequency of the sensor is approximately 70 KHz at an external pressure value of approximately 820 Torr. Similarly, the points 140A and 140B of the curve 140 indicate that the resonance frequency of the sensor is approximately 80 KHz at an external pressure value of between 770 Torr and 780 Torr (the value for the peak point may be determined by using a curve fitting method as is disclosed in detail with respect to FIG. 9 above).

The sensor 20 (or any other type of suitable ultrasonic pressure sensor) may thus be calibrated by repeating the measurements as disclosed hereinabove at different sensor exciting ultrasound frequencies. In accordance with one possible embodiment of the present invention, this calibration may be performed by using an ultrasound beam including a single sensor exciting frequency and the carrier frequency and repeating the measurement of the sideband amplitude at different known pressure values to obtain sideband amplitude data and sensor resonance frequency for the exciting frequency (for example, as is illustrated in FIG. 9 for an exciting frequency of 61 KHz) and then changing the sensor exciting frequency and repeating the measurements at different pressure values within the working range of the sensor 20, until data is acquired for all the useful sensor exciting frequencies at all the desired pressure values. By finding the maximum sideband amplitude it is then possible to construct an LUT or a formula correlating the sensor's resonance frequency with the external pressure.

Alternatively, in accordance with another possible embodiment of the present invention, the sensor's calibration may be performed by using an ultrasound beam that simultaneously includes all the sensor exciting frequencies and the carrier frequency, and repeating the measurement at different known pressure values covering the working range of the sensor 20. The frequency domain representation of the processed returning signal in this method includes multiple pairs of sidebands. Each pair of sidebands corresponds with a particular exciting frequency (see, for example, the graph of FIG. 10). Since it is possible to accurately measure multiple sidebands in the same frequency domain data, by finding the maximum sideband amplitudes for the different sidebands it is possible to construct an LUT or formula correlating the sensor's resonance frequency with the external pressure.

Figure 12:
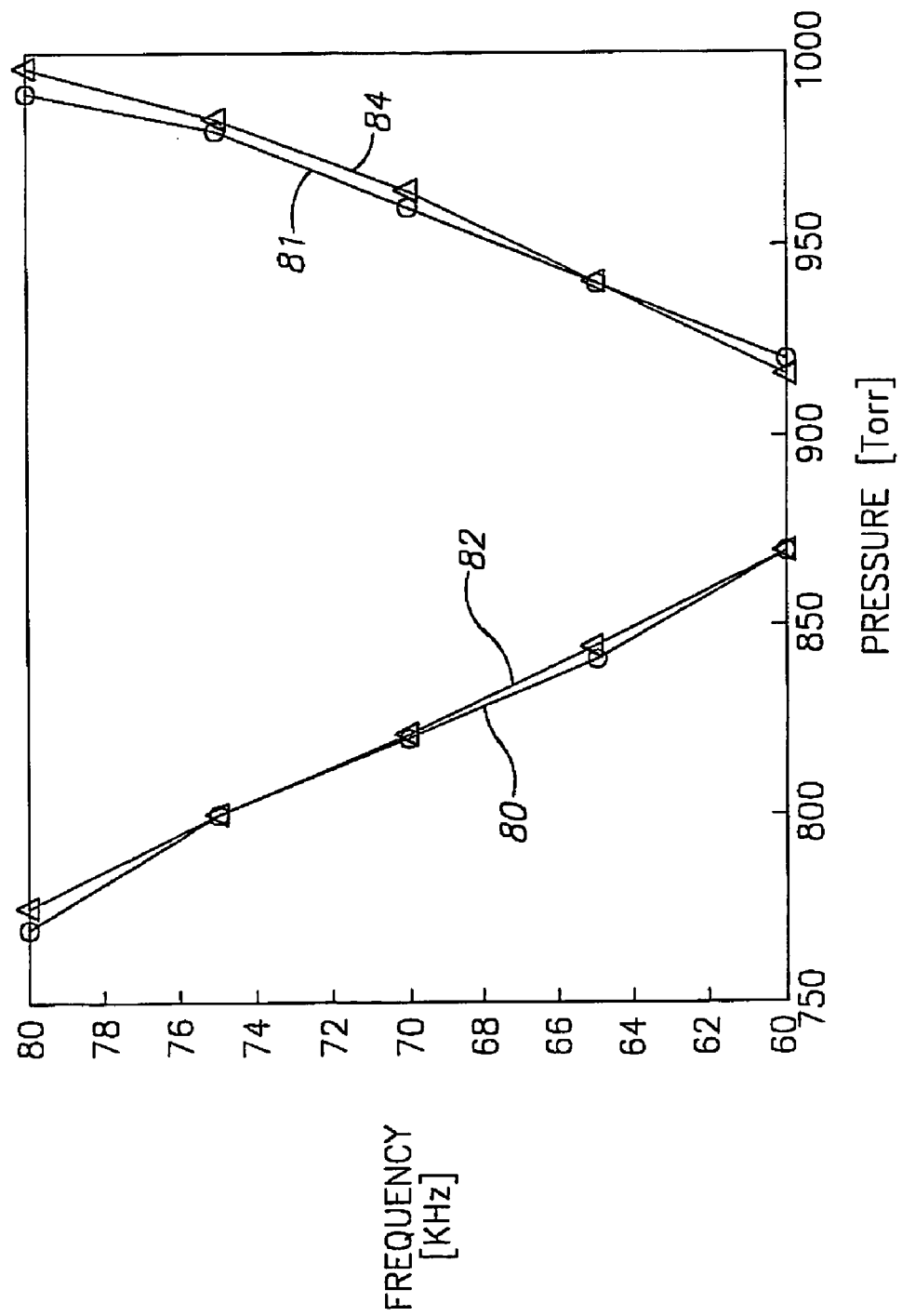
FIG. 12 which is a schematic graph illustrating the experimentally determined dependence of the resonance frequency of the sensor 20 of FIGS. 2–3 on the pressure in a controlled pressure chamber using an interrogating ultrasonic beam simultaneously including a carrier frequency and five different sensor exciting frequencies.

Reference is now made to FIG. 12 which is a schematic graph illustrating the experimentally determined dependence of the resonance frequency of a specific example of the sensor 20 of FIGS. 2–3 on the pressure in a controlled pressure chamber using an interrogating ultrasonic beam simultaneously including a carrier frequency and five different sensor exciting frequencies.

The vertical axis of the graph of FIG. 12 represents the resonance frequency of the sensor, and the horizontal axis represents the pressure within the pressure chamber. The sensor 20 was immersed in water and the experiments were conducted as disclosed in detail hereinabove. The carrier frequency of the interrogating beam was 3.0 MHz and the sensor exciting frequencies (which were simultaneously transmitted with the carrier frequency) were 60 KHz, 65 KHz, 70 KHz, 75 KHz, and 80 KHz. The returning signal for each of the experimentally used pressure values was received, digitized and processed as disclosed hereinabove, the time domain digitized data was multiplied by a Hamming window function and a DFT was performed on the resulting data to obtain frequency domain data for each experimental pressure value as disclosed hereinabove (see, for example, the frequency domain representation of FIG. 10).

The mean sideband amplitudes corresponding to each of the sensor exciting frequencies included in the transmitted signal were determined by averaging the amplitudes of the two sidebands for each of the sensor exciting frequencies for all the experimental pressure values by using the sideband amplitude at the calculated sideband frequency (as disclosed hereinabove). At each specific experimental pressure value, the amplitude of the sidebands corresponding to each sensor exciting frequency at that pressure was determined and the sensor exciting frequency having the maximal sideband amplitude was found. At this point the sensor's resonance frequency for the experimental pressure value was determined by using two different methods, the raw data method and the curve fitting method, as described in detail hereinabove. In the first method, the exciting frequency that had the maximal sideband amplitude was used as the value of the sensor's resonance frequency for that experimental pressure value. In the second method, a curve was fitted to the data points of sideband amplitude and corresponding exciting frequency, and the maximum point of the fitted curve was used as the sensor's resonance frequency for that experimental pressure value.

The curves 80 and 81 (of FIG. 12) connecting the data points represented by the hollow circle symbols represent the resonance frequency vs. pressure curves using the actual pressure points at which the amplitude peaks were found at each frequency used (raw data). For example, the point 142A of FIG. 11 represents an example of raw data sideband amplitude for a transmitted exciting frequency of 70 KHz. (It is noted that the point 142A is given as an explanatory example only and was not included in the data set shown in FIG. 12 since it belongs to a different experiment).

The curves 82 and 84 (of FIG. 12) connecting the data points represented by the hollow triangular symbols represent the resonance frequency vs. pressure curves using the pressure points at which the maximum amplitude peaks were determined by using a third order polynomial curve fitting estimation method as disclosed hereinabove (with respect to FIG. 9). For example, the point 44 of the fitted curve 40 represents an exemplary pressure point at which the computed sideband amplitude is maximal (It is noted that the point 44 is given as an explanatory example only and was not included to the data set shown in FIG. 12 since it belongs to a different experiment).

The curves 80 and 81 were formed by connecting by straight lines the raw experimental data points. Similarly, the curves 82 and 84 were formed by connecting by straight lines the data points obtained from the fitted curves. It is noted that there is only a small difference in the curves obtained using raw data points and points computed using the fitted curve method.

It is also be noted that the particular sensor used for obtaining the results of FIG. 12 was found to behave linearly over most of the pressure and frequency range as can be seen in FIG. 12. However, in other sensors having an extended pressure working range, it may be possible to use non-linear calibration curves.

The data points relating the resonance frequency to pressure may be used for constructing the sensor's LUT or formula of calibration data for the relevant pressure working range.

It may also be possible, in accordance with yet another possible embodiment of the present invention, to use a plurality of groups of sensor exciting frequencies at the known pressure values, and to repeat the measurements at all desired pressure values while changing the sensor exciting frequencies in each frequency group included in the interrogating ultrasound beam until a full data set is acquired covering all the desired exciting frequencies at all the desired pressure values. It may then be possible to construct an LUT correlating the sensor's resonance frequency with the external pressure, by finding the amplitude maxima of the sidebands as disclosed hereinabove.

By determining the amplitude peak of the appropriate sidebands at different exciting ultrasonic frequencies for a selected pressure range (in a non-limiting example, for the particular frequency of 611 Hz shown in FIG. 9, such a pressure range may be between 820–880 Torr within which the point 42 of the fitted curve 40 is located), a suitable look up table (LUT) may be constructed for each individual sensor in which discrete resonance frequency values are associated with discrete pressure values.

It is noted that in generating the LUT for a sensor the curve fitting methods used for generating the amplitude vs. pressure curves (such as the curve 40 of FIG. 9, or the like) may be varied and many other suitable types of curve fitting methods, known in the art, may be used to generate the fitted curves and determine the amplitude peak values for the LUT. Additionally, if it is possible to quantitatively express the dependence of the resonance frequency of a sensor on the external pressure within a suitably defined pressure value range by an analytical function, such a function may be used instead of an LUT to compute the pressure from experimentally obtained sensor resonance frequencies within the defined pressure range.

Measuring Intraluminal Pressure with a Passive Ultrasonic Sensor

Measuring blood pressure (or other blood pressure related parameters or characteristics) within a blood vessel or in an artificial graft or other parts of the cardiovascular system may be performed by implanting one or more sensors (such as, but not limited to, the sensor 20 of FIGS. 2 and 3) in the lumen of a blood vessel (not shown) or in a desired position within the artificial graft or the cardiovascular system. The resonance frequency of the resonating parts of the sensor (such as, for example, the vibratable membranes 29A, 29B, 29C, 29D, 29E, 29F, 29G, 29H, and 29I of the sensor 20) changes according to the pressure exerted on it by the blood.

By measuring the resonance frequency of the resonating parts of the sensor (such as, for example, the vibratable membranes 29A, 29B, 29C, 29D, 29E, 29F, 29G, 29H, and 29I of the sensor 20), it is possible to determine the blood pressure in the vessel using a sensor-specific look up table (LUT) or a calibration function, which provides the relationship between pressure exerted on the resonating parts of the sensor and the resulting resonance frequency. The LUT may be obtained by suitable calibration of the sensor prior to implantation, as disclosed hereinabove.

The resonance frequency of the sensor(s) may be measured by transmitting an ultrasound (US) beam from an external ultrasonic transducer or suitable ultrasonic probe suitably coupled to the body of the patient (such as, for example, the transducer(s) unit 62 of FIG. 5) directing the beam at the sensor(s), receiving signals returned from the sensor(s), and analyzing the waveform of the returned signals as disclosed hereinabove. The low frequency echoes may be filtered out as disclosed hereinabove for the system 50, and the Doppler effect may be measured in the frequency modulated returning signals as disclosed.

When measuring blood pressure (or any other pulsatile or cyclically varying pressure in a measurement environment), if a fixed group of exciting frequencies is used, the group or groups of sensor exciting frequencies which are used for exciting the sensor(s) may not always be optimally arranged such that they are near or around the resonance frequency of the sensor, due to the dynamic pressure changes which change the resonance frequency with time.

In accordance with one embodiment of the invention, the measurements may be performed using a closed loop measurement method that is useful in solving the above problem. In accordance with another embodiment of the invention, the measurements may be performed using an open loop measurement method. The two methods (open loop method and closed loop method) are disclosed in detail hereinafter.

When the system (such as, for example, the system 32 or 50) operates to determine the blood pressure changes with time, the system may perform a series of sequential measurements. When measuring a single point of blood pressure during the blood pressure pulsatile cycle it may be possible to use a closed loop method. In accordance with the closed loop method of the present invention, the pressure may be determined using a continuous transmitted wave (CW) or a sonic frequency burst simultaneously including a carrier frequency and a first group of sensor exciting frequencies (typically about 5–10 different sensor exciting frequencies, but other different numbers of sensor exciting frequencies may also be used) having frequency values optimal for the specific pressure range. The exciting frequencies may be close enough (on the frequency axis) in order to get a desired measurement accuracy.

The amplitudes of the sidebands corresponding to the different selected exciting frequencies in the returning signal are determined as disclosed hereinabove and used in order to determine the sensor's resonance frequency (which may be used to determine the blood pressure using a look-up table or a calibration function as disclosed hereinabove).

In the next pressure measurement of the sequence of measurements, the system may generate a transmitted CW or another frequency burst including the carrier frequency and a second group of frequencies (typically about 5–10 different sensor exciting frequencies, but other different numbers of sensor exciting frequencies may also be used). The second group of sensor exciting frequencies may be different than the first group of sensor exciting frequencies, and may contain different values of sensor exciting frequencies which may also (optionally) be differently spaced apart from each other such that they are better positioned and better spaced apart (on the frequency axis) in order to enable a better determination of the next estimated resonance frequency.

The closed loop method may be achieved by analyzing the measured signal in real time and changing the transmitted sensor exciting frequencies according to the analysis results in order to trace (follow) the resonance frequency as it changes. Thus, by continuously estimating or predicting the approximate frequency range within which the resonance frequency in the next measurement may fall, the system may effectively determine an optimized set of sensor exciting frequencies that are suitably distributed within the estimated frequency range for performing the next measurement.

In accordance with one possible embodiment of the invention, if the closed loop method is used by the system, an external signal may be (optionally) used to enable the system to determine where the current measurement is located within the pulsatile blood pressure cycle (see, for example, the arrows marked "optional external synchronizing signal" entering the synchronizing unit 74 of the system 50 of FIG. 5, or the processor controller unit 38 of the system 32 of FIG. 4). For example, in accordance with one embodiment of the present invention, the system may use a known identifiable point on a physiological signal recorded from the same patient and correlated or synchronized with the blood pressure. In accordance with one possible embodiment of the closed loop method, the physiological signal may be the ECG signal recorded from the patient. The peak of the QRS complex of the recorded ECG signal (not shown) may be used as such an identifiable point for system synchronization, since it is normally synchronized with a particular point in the blood pressure cycle. It is noted that other identifiable points of the ECG signal other than the peak of the QRS complex or combinations of such points, may also be used for synchronization purposes.

It is further noted that it may be possible to use other types of physiological signals for synchronization purposes in the closed loop measurement method. For example one may use a microphone suitably placed on the chest to record heartbeat sound, and it may be possible to use one or more known points in the simultaneously recorded sound signal for synchronization purposes.

An advantage of the closed loop measurement method may be that by suitably selecting the sensor exciting frequencies to be in the vicinity of the expected (estimated) resonance frequency of the sensor it allows the use of a smaller group of sensor exciting frequencies in each single measurement without degrading the measurement accuracy and therefore allows to increases the energy transmitted at each frequency, improving the measurements signal to noise ratio (SNR), or to increase the accuracy while using the same energy.

In accordance with yet another embodiment of the closed loop of the present invention, the system may initially start by using the open loop method of the invention in a test period. During the test period, the system may sample (and may store) test data including a desired number of cycles of the resonance frequency changes of the sensor corresponding to a few cycles of the blood pressure. The system may then use this test data to obtain an estimated frequency range within which the mean resonance frequency of the sensor may fall at each specific sampled time point within the cycle (for example, by taking the lowest and the highest values of the determined sensor resonance frequency for each specific sampled time point within all the sampled cycles in the test data).

In accordance with one possible embodiment of the present invention, the system may sample a fixed number of data points within each cycle of the blood pressure cycles included in the sampled test data. In a non-limiting example, the system may sample fifty blood pressure cycles, at a sampling rate of 50 Hz, (for a pulse beat rate of about 1 pulse per second, this will result in approximately 50 samples per blood pressure cycle). The determined sensor's resonance frequency data for the fifty pulse cycles may then be processed to obtain an average cycle data. In accordance with one possible embodiment, the average cycle data may include for each of the fifty sampled points within the average cycle the maximal and minimal sensor resonance frequency determined from all 50 measurements. Thus, for each of the fifty points in the averaged cycle, the system may sore the range (stored as the minimum and maximum values) of the sensor's resonance frequency values of the point, and the time or serial number of the point within the average cycle. Alternatively, the system may store for each of the fifty points in the averaged cycle, the mean sensor's resonance frequency value for all fifty measured cycles and the standard deviation of the mean, or the variance of the mean, or any other suitable statistical parameter, which may be later used for predicting or estimating the resonance frequency of the sensor for that time point within the cycle. The values of the averaged cycle data may be stored as an LUT or in any other suitable form known in the art.

After the test data has been collected and stored using the open loop method, the system may, if desired, switch to using the closed loop method. The system may determine the sensor's resonance frequency for the current measurement point (using the open loop method. The system may then estimate or predict the expected value of the sensor's resonance frequency based on the averaged cycle data stored or recorded as disclosed hereinabove. The system may determine the position of the current measurement time point within the pulse cycle. The determination may be based on synchronization with an independently recorded biological signal such as the QRS complex peak of an ECG signal recorded simultaneously in the same patient or on any other suitable timing reference point in another recorded signal which is synchronized with or associated with the cardiac cycle, such as, but not limited to, a recorded signal of the heart sounds, or the lice.

After the system determines the position of the current measurement point within the cycle, the system may obtain the estimated range of frequencies which the sensor's resonance frequency may be in the next measurement point from the predicted frequency range or the mean frequency and the standard deviation (or the variance, or any other suitable statistical parameter) stored in the LUT of the Average cycle data.

The system may then select an optimized group of sensor exciting frequencies to be transmitted in the next measurement. The chosen group of sensor exciting frequencies may be suitably optimized or fitted and may be distributed over the expected frequency range predicted for the next measurement to improve the accuracy of the measurement. This procedure may be repeated for the next measurement cycles to increase the overall measurement accuracy.

In accordance with the open loop method of the present invention, all the sequential measurements may be performed by transmitting the full set of selected sensor exciting frequencies simultaneously with the carrier frequency in each pressure measurement using a transmitted CW or a frequency burst. In accordance with one non-limiting example, in the pressure range for blood pressure measurements performed at sea level using the sensor 20, it may be practical to use between 10–40 different sensor exciting frequencies within the frequency range of 50–70 KHz. It is, however, noted that this frequency range and the number of discrete sensor exciting frequencies used is not obligatory to practicing the invention and other different values of the frequency range and of the number of discrete sensor exciting frequencies may also be used depending, inter alia, on the range of pressure variations in the measurement environment, the altitude at which the measurement is performed, the characteristics of the sensor(s) used for performing the measurement, the measurement environment and noise characteristics, the Q of the sensor, the SNR, the rate of pressure change as a function of time (dP/dt), the rate of change of the resonance frequency with pressure (df/dP) and the like.

Preferably (but not obligatorily), the sensor exciting frequencies used in the open loop measurement embodiment are equally spaced apart from each other across the working frequency range. For example, if twenty one different sensor exciting frequencies are used in the range of 50–70 KHz, the lowest sensor exciting frequency may be 50 KHz and the rest of the sensor exciting frequencies may be at 1 KHz increments from the lowest frequency (at 51, 52, 53 . . . 68, 69, and 70 KHz).

The group of frequencies used in blood pressure measurements (or in the measurement of other pressure variations in other measurement environments) may be assembled in various different ways. Thus, assuming N sensor exciting frequencies need to be transmitted (together with the carrier frequency) for a measurement, the following options may be used:

In accordance with one embodiment of the invention, a single exciting frequency group may be used. All N resonator exciting frequencies may be transmitted at the same time for the same period of time T (together with the carrier frequency). In this option, the duration of a single measurement period is T since all the needed frequencies are simultaneously transmitted within a single transmitted frequency burst. A burst or a CW may be used simultaneously containing all the sensor exciting frequencies and the carrier frequency (if a short burst is used the data should be sampled or processed after a suitable frequency stabilization period).

In accordance with another embodiment of the invention, N exciting frequency groups may be used. The different resonator exciting frequencies are transmitted one after the other in a sequential manner. Each exciting frequency is transmitted (together with the carrier frequency) for the same period of time T1. In this option, the duration of a single measurement period using all the needed exciting frequencies is N·T1 since the frequencies needed for a measurement are sequentially transmitted in N different transmitted bursts. If the different frequency bursts are separated by silent time intervals, the single measurement period may be N·(T1+$T_S$), wherein $T_S$ is the total duration of the silent intervals between the different frequency bursts.

In accordance with yet another embodiment of the invention, M groups of exciting frequencies may be used. In this intermediate option, M frequency groups may be sequentially transmitted. Each frequency group may include L different simultaneously transmitted exciting frequencies (in this non-limiting case, M=N/L). Each group of exciting frequencies may be transmitted (together with the carrier frequency) for a time $T_{GROUP}$. In this option, the duration of a single measurement period using all the needed exciting frequencies may be M·$T_{GROUP}$ (assuming there is no "silent" interval between the different transmitted groups). If the different frequency groups are separated by silent time intervals, the single measurement period may be M·($T_{GROUP}$+$T_S$) wherein $T_S$ is the duration of the silent interval between the different frequency group bursts.

It is noted that while for certain applications it may be preferred to transmit M groups each including an equal number of (different) exciting frequencies, this is not obligatory and other different exciting frequency grouping arrangements may be used in which some of the groups or each group may include a different number of frequencies. Additionally, it may be possible to use different transmitting times for different frequency groups.

Preferably, the sensor is operated within its linear range (in this range the movements of the vibratable membrane(s) or of other resonating members of the sensor depends linearly on the amplitude of the sensor or resonator exciting frequency). In order to remain within the linear range of the sensor, it may be needed to limit the transmitted signal amplitude such that the combined amplitudes of the sensor exciting frequencies do not exceed the sensor's linear range. The number of sensor exciting frequencies that may be used per frequency group may therefore also be limited.

Thus, in some cases it may be difficult to use all N required exciting frequencies simultaneously, because the amplitude at each of the transmitted exciting frequencies or at some of the transmitted exciting frequencies is too low for obtaining a good SNR because the energy of the entire transmitted beam is limited to avoid exceeding the sensor's linear range, or the FDA limitations for humans. For such cases it may be preferred to use the last alternative indicated and use M groups of sensor exciting frequencies, wherein each frequency group is separately transmitted. By lowering the number of sensor exciting frequencies which are simultaneously transmitted in a group of frequencies it may be possible to increase the amplitude at each frequency (in the group) to an acceptable level enabling a good SNR without increasing the overall energy in the beam to a value which causes a non-linear sensor response, or which may exceed the energy level permitted for use in human patients.

It is noted that, the system should use a number of different sensor exciting frequencies that is sufficient for getting a good measurement accuracy.

It will be appreciated that the parameters of transmitted interrogating beam may be adapted to the measurement needs and limitations. For example, in the open loop method if the total transmitted energy per unit time does not exceed the allowed limit in human patients, the pressure measurements may be performed by continuously transmitting all the N selected sensor exciting frequencies and the carrier frequency as long as the real time a measurement is needed. The returning signal may be continuously sampled and suitable selected portions of the digitized signal data may be processed as needed. The duration of the selected data portions should be sufficiently long to enable the desired frequency resolution in the frequency domain measurements.

It may also be possible to continuously transmit all the N selected sensor exciting frequencies and the carrier frequency but to sample and process only portions of the data at preset time intervals.

Alternatively, if the total transmitted energy for a continuous beam may exceed the allowed limit in human patients or if for any reason it is not desired to continuously transmit the carrier frequency and/or the sensor exciting frequencies, the pressure measurements may be performed by transmitting frequency bursts, each burst may include all the N selected sensor exciting frequencies and the carrier frequency. Each transmitted burst may have a finite (and, preferably, short) burst duration. The bursts may be transmitted as long as real time a measurement is needed. The returning signals may be sampled either continuously or intermittently (for example, by synchronizing the sampling with the periods of transmitting of the bursts) and the sampled data may be processed and analyzed as disclosed.

When analyzing the digitized data of the returning signals when such bursts are transmitted, it may be desired to use only part of the digitized returning signals for performing the DFT procedure. This may be done in order to ensure use of data from the period of time at which the frequency content of the signal returning from the sensor has sufficiently stabilized. For example, if the frequency bursts have a duration of eight milliseconds and the burst frequency is 100 Hz (one burst is transmitted every ten milliseconds), it may be advantageous to perform the FFT on the last four milliseconds of the acquired digitized returning signal to ensure that the processed data was not acquired immediately after burst initiation and that the frequency content of the signal returning from the sensor has stabilized at the time the data was sampled. The values indicated above are given by way of example only and other different values may also be used for data analysis.

For the methods using multiple frequency bursts, each burst having the carrier frequency and a single sensor exciting frequency or a discrete subgroup of exciting frequencies, similar considerations may dictate the timing and duration of sampling and of processing of the sampled data.

It is noted that if, for example, a single measurement period includes three frequency bursts each containing the carrier frequency and five different sensor exciting frequencies (this arrangement is given by way of example only and other different frequency subgroup arrangements may be used), the system may preferably transmit three contiguous bursts each containing the desired frequencies by starting the second burst immediately at the time of termination of the first burst and starting the third burst immediately at the time of termination of the second burst. In such a case the time duration in which data is sampled and/or processed may be shorter than the individual burst durations to ensure that the processed data is obtained in a time at which the frequency content of the signal returning from the sensor has sufficiently stabilized to avoid errors. Thus, the burst duration should be long enough to allow for the sensor frequencies to stabilize and for a sufficient data to be collected for performing the DFT, but should be short enough to ensure that there is no significant pressure change over the time necessary to obtain data for the desired set of sensor exciting frequencies.

Alternatively, if several multiple frequency burst are used in each measurement period, the bursts having different frequency subgroups may also be non-contiguous and may be separated from each other by time intervals in which no signal is transmitted ("silent" inter-burst intervals).

When several frequency subgroup bursts are used (either in a contiguous mode or in the non-contiguous mode, as disclosed hereinabove), care should be taken to ensure that the burst duration of each burst and the total duration of all the bursts within a single measurement period (the measurement period duration) is short enough such that the errors introduced by the pressure change within the duration of each burst or within the total measurement period are within acceptable error limits.

The low frequency echoes may be filtered out by analog filters prior to the digital analysis performed by the system.

The main undesirable influence of the short burst duration is due to the discontinuities at the beginning and the end of the signal transmission time. Because of these discontinuities, the transitions' frequency content is distributed across the spectrum of the DFT processed data resulting in higher noise levels. At steady state (at a time sufficiently removed from the transmitted signal's initiation point and/or termination point) this effect is reduced. Therefore, to avoid high noise levels, the system may either use a continuous wave transmitted signal (CW), or may use frequency burst durations and data sampling periods that reduce the noise levels.

It is further noted that other transmission arrangements are also possible. For example, it may be possible to continuously transmit the carrier frequency for the entire duration of a measurement session and to transmit the frequency bursts intermittently at times for which measurement data is needed. This method of continuous transmission of the carrier frequency may be used for all different alternative sensor exciting frequency group arrangements, including, but not limited to the use of one or more frequency burst groups. Such frequency subgroups may include either contiguous sensor exciting frequency subgroups or sensor exciting frequency subgroups separated from each other in time. Such frequency subgroups may include one or more sensor exciting frequencies in accordance with all the possible combinations and subgroup arrangements disclosed hereinabove).

Figure 13:
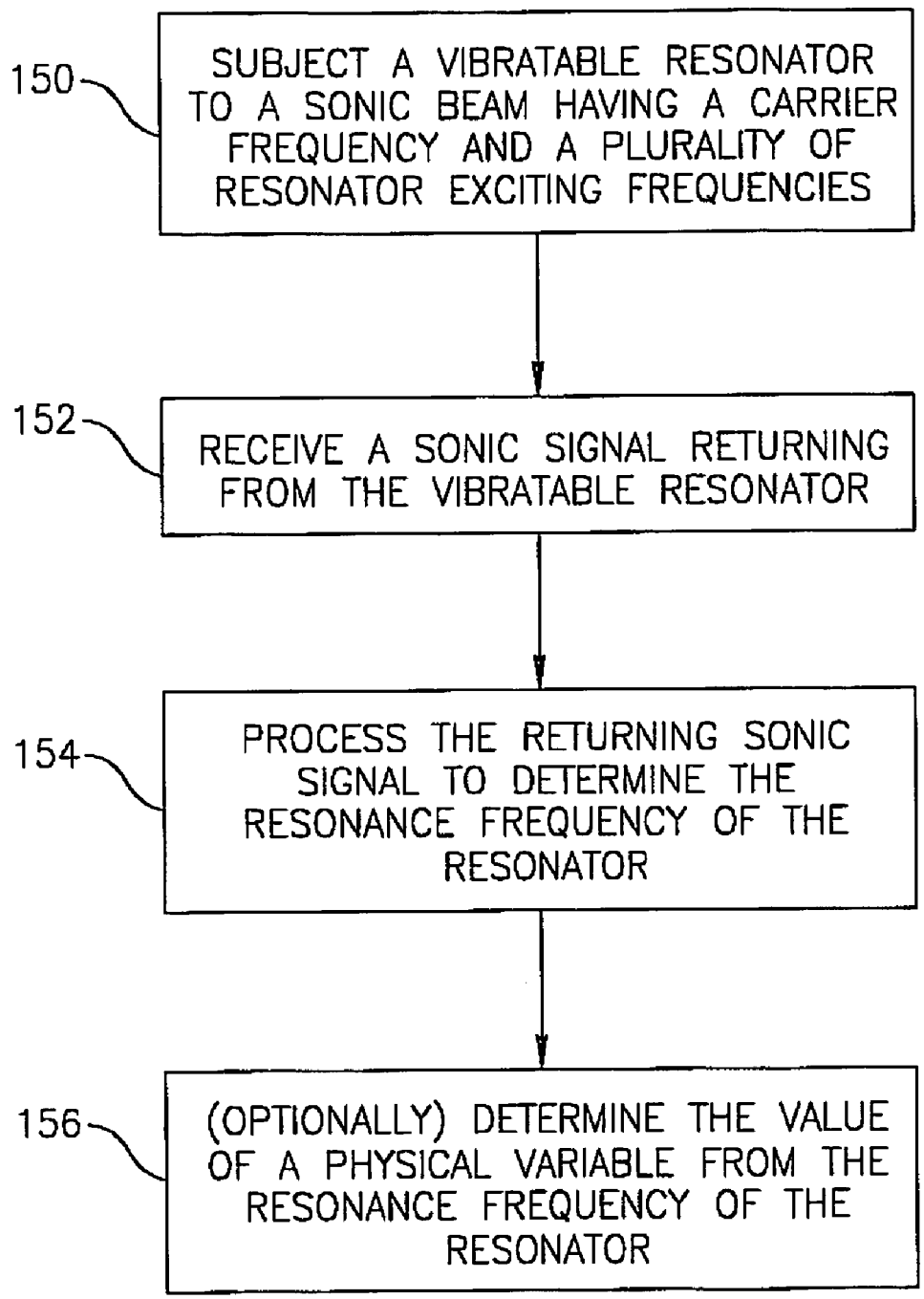
FIG. 13 is a schematic flow diagram illustrating the general steps of a method for determining the resonance frequency of a resonator by using the Doppler shift based measurement, in accordance with an embodiment of the present invention.

Reference is now made to FIG. 13 which is a schematic flow diagram illustrating the general steps of a method for determining the resonance frequency of a resonator by using the Doppler shift based measurement method of the present invention.

In accordance with the method of FIG. 13, a vibratable resonator is subjected to an interrogating sonic beam by directing at the resonator a sonic beam having a carrier frequency and a plurality of N resonator exciting frequencies (step 150). The resonator may be any type of resonator known in the art that has one or more parts configured to be vibrated by the resonator exciting frequencies of the interrogating sonic beam. The carrier frequency may be selected such that it does not excite substantial vibrations of the resonator but is reflected from the vibrating part(s) of the resonator, and may also be reflected by any non-vibrating parts of the resonator as well as by other reflecting objects and/or surfaces and/or interfaces which may be present in the resonator's environment The sonic beam may be a continuous wave (CW) beam, but may also be a chirped beam or a pulsed beam having a series of frequency bursts, as disclosed in detail hereinabove and known in the art. In accordance with an embodiment of the present invention, the plurality of N resonator exciting frequencies may all be transmitted simultaneously with the carrier frequency, as disclosed in detail hereinabove. Alternatively, in accordance with other embodiments of the invention, the carrier frequencies and the resonator exciting frequencies may be transmitted as bursts.

In accordance with one embodiment of the invention, each burst has a finite duration and may include a single resonator exciting frequency and the carrier frequency, as disclosed in detail hereinabove. The bursts may be repeated while changing the resonator exciting frequency, until all of the N resonator exciting frequencies have been transmitted.

In accordance with another embodiment of the invention, each burst has a finite duration and may include a single resonator exciting frequency and the carrier frequency. The bursts may be repeated while changing the resonator exciting frequency, until all the N resonator exciting frequencies have been transmitted.

In accordance with yet another embodiment of the invention, each burst has a finite duration and each burst may simultaneously include the carrier frequency and a subgroup of M resonator exciting frequencies. The bursts may be repeated while changing the resonator exciting frequencies in the burst, until all the N resonator exciting frequencies have been transmitted. The number of the resonator exciting frequencies in a subgroup may be equal to the number of resonating frequencies in all the other subgroups. Alternatively, the number of resonator exciting frequencies in a subgroup may differ from the number of the resonator exciting frequencies in other subgroups.

The sonic signals returning from the resonator (and from other reflecting parts of the environment in which the resonator is disposed) are received by the system, such as, for example, by the systems 32 or 50 of FIGS. 4 and 5, respectively (Step 152).

The system may then process the returning sonic signal to determine the resonance frequency of the resonator using any of the methods disclosed herein (step 154). Preferably, in step 154, the system digitizes the returning signal (with or without using an analog front end as disclosed hereinabove) and uses a DFT of the digitized signal to determine the amplitude of the Doppler shifted sideband peak or peaks for each resonator exciting frequency. For each time point at which the measurement is performed the system may determine the exciting frequency at which the sideband is maximal. If a sufficiently high number of sensor exciting frequencies is used in the measurement, the value of the resonator exciting frequency at which the sideband amplitude is maximal may be taken as the resonator resonance frequency.

Alternatively, if a relatively small number of resonator exciting frequencies are used in the measurement, a curve may be fitted to the data points representing the sideband amplitudes at different resonator exciting frequencies, and the frequency at which the fitted curve has a maximum amplitude is taken as the resonator's resonance frequency. Any suitable curve fitting known in the art may be used for performing the curve fitting.

It is noted that while the DFT method may be used to obtain a frequency domain data from which the sideband amplitude(s) may be determined, any other suitable type of algorithm or method or transform known in the art for obtaining frequency domain data or time domain data for determining the amplitude of the sideband frequency peak may be used in the present invention.

If the resonator is a resonating sensor or a resonating part included in a sensor having a resonance frequency which is a function of a physical variable to be measured, (such as for example the pressure sensor 20 of FIG. 2), the method of FIG. 13 may also have an optional step of determining the value of the physical variable from the determined value of the resonance frequency of the resonator (step 156).

Figure 14:
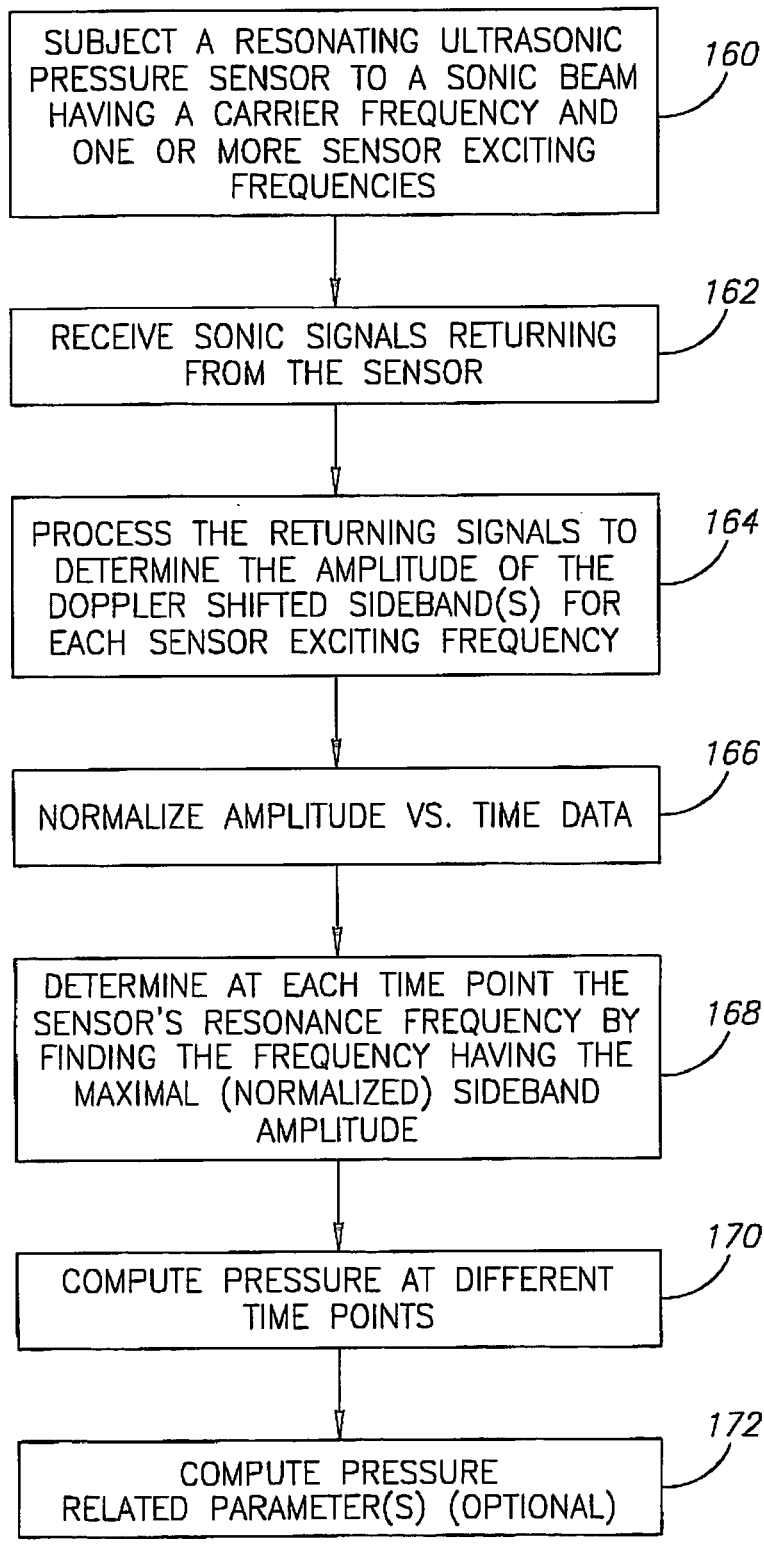
FIG. 14 is a schematic flow diagram illustrating the steps of a method for determining the intraluminal blood pressure within a blood vessel or a vascular graft using an implanted pressure sensitive passive ultrasonic resonating sensor and a system using the Doppler shift based measurement method of the present invention.

Reference is now made to FIG. 14 which is a schematic flow diagram illustrating the steps of a method for determining the intraluminal blood pressure within a blood vessel using an implanted pressure sensitive passive ultrasonic resonating sensor and a system using the Doppler shift based measurement method of the present invention.

A resonating pressure sensor (such as but not limited to, the passive ultrasonic pressure sensor 20 of FIG. 2) may be implanted in the lumen of a blood vessel as disclosed hereinabove.

The method may include subjecting the sensor to a sonic beam having a carrier frequency and one or more sensor exciting frequencies, as disclosed hereinabove (step 160). The interrogating beam may be implemented as a CW beam or as a pulsed beam including a plurality of frequency bursts. The bursts may be contiguous as disclosed in detail hereinabove (with different sensor exciting frequencies in each of the different bursts included within a single measurement period), or may be spaced apart by silent intervals, as disclosed hereinabove.

A single burst may include the carrier frequency and single sensor exciting frequency. Alternatively, a single burst may include the carrier frequency and a group of selected sensor exciting frequencies, as disclosed in detail hereinabove.

The method may also include receiving the signal returning from the sensor (Step 162). The receiving of the returning signal may be done by any suitable transducer (such as, for example, the transducer(s) unit 34 of FIG. 4, the transducer(s) unit 62 of FIG. 5, or the like). The received returning signals may include echoes reflected from the sensor's vibratable membranes (or other vibratable members of the sensor, if the sensor used is different than the sensor 20), echoes reflected from the non-vibratable parts of the sensor and other echoes reflected from reflecting objects (bones, or other different tissues, or the like) or reflecting interfaces in the body.

The method may further include processing the returning signals (or parts thereof) to determine the amplitude of the Doppler Shifted frequency sidebands for each sensor exciting frequency (step 164). The returning signals may be processed by any suitable type of processing unit known in the art and described herein (including, but not limited to the processing controlling unit 38 of FIG. 4 or the processing/controlling unit 68 of FIG. 5). The signals may be processed using any type of processing method known in the art or disclosed hereinabove for determining the amplitude of the Doppler shifted sideband frequencies. The processing of the returning signals may include any of the methods disclosed hereinabove for signal conditioning and/or processing, and/or digitizing and/or filtering, and/or down-converting, as is known in the art and disclosed hereinabove. The system hardware configuration may be any of the analog and/or digital, and/or hybrid analog/digital implementations disclosed and illustrated herein, but may also be implemented using any other hardware and/or software implementation known in the art.

The returning signals or portions of the returning signals occurring after the frequency content of the transmitted signals has stabilized may be sampled as raw data or may be first pre-processed by suitable filtering and down-converting as disclosed hereinabove and digitized. Preferably, the digitized data may be subjected to DFT processing as disclosed hereinabove to obtain frequency domain data and the amplitudes of the sideband frequencies may be determined as disclosed hereinabove for each of the sensor exciting frequencies used in a single measurement period. The sideband amplitude peak may be determined from a single sideband peak or from both sideband peak amplitudes by using an arithmetic mean or a geometrical mean, or the like, as disclosed in detail hereinabove.

Other methods may however be used for determining the amplitudes at the Doppler shifted frequencies. The processing of step 164 may provide data which may include a plurality of values of the amplitudes of the sideband frequencies for each measurement period (if the measurements are repeated in time as they may be for obtaining the blood pulse shape in real time, or in nearly real time).

The determined amplitude values of the sideband frequencies may then be (optionally) normalized (step 166). The normalizing may be performed in order to compensate for small variations in the energy output of different transmitted sensor exciting frequencies in the transmitted interrogating beam or to correct for selective attenuation of certain sensor exciting frequencies due to standing waves.

It is noted that while practically such standing wave problems should be minimal in measurements performed in-vivo with implanted sensors, it may be more substantial in performing measurements in other measurement environments (such as for example, in measuring the pressure within a reactor having reflecting walls with fixed dimensions) which may necessitate the use of normalizing across different frequencies.

Figure 15A:
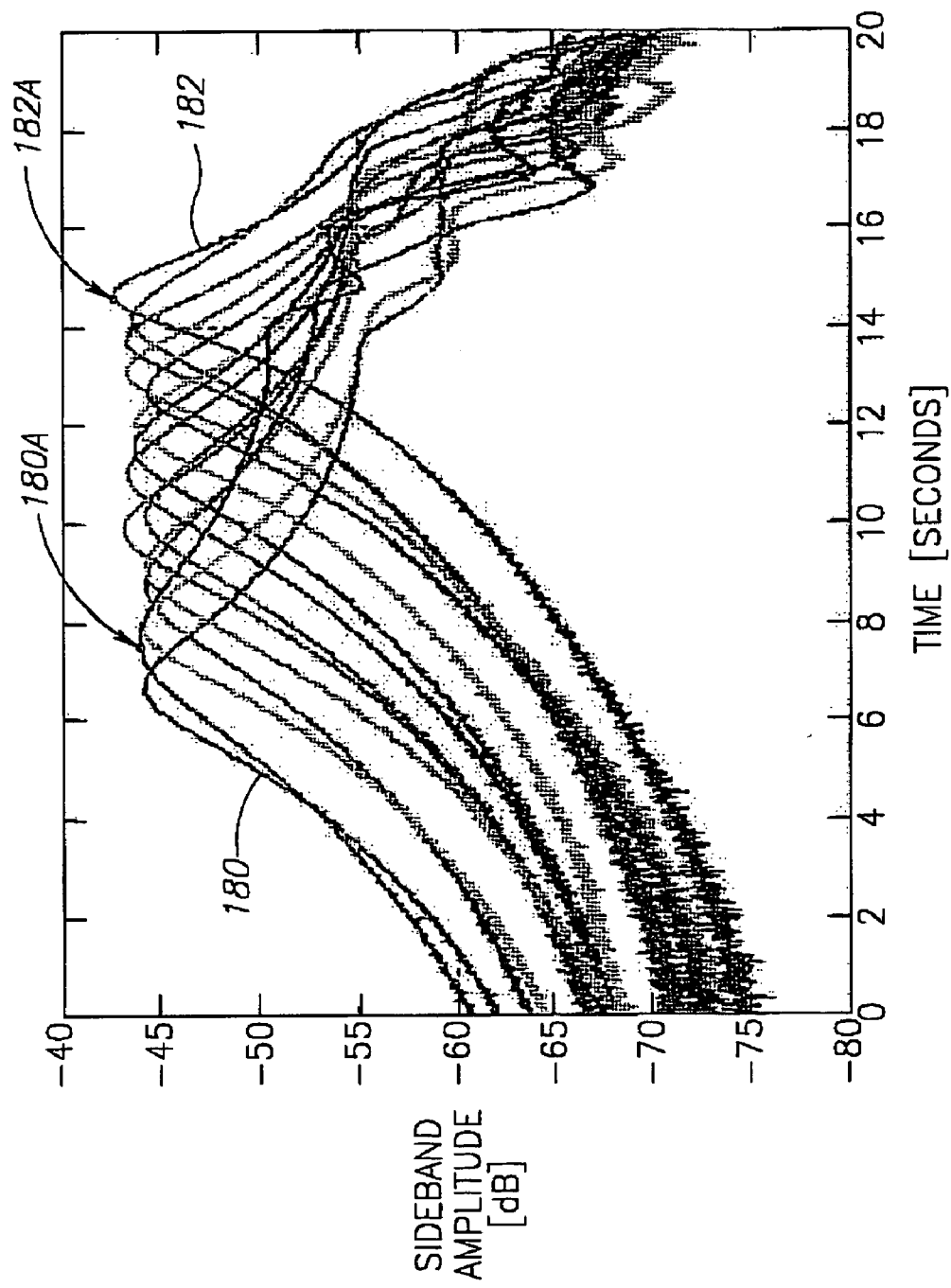
FIG. 15A is a schematic graph illustrating an example of non-normalized experimentally obtained data representing the time dependence of the measured sideband amplitude for a plurality of different sensor exciting frequencies.
Figure 15B:
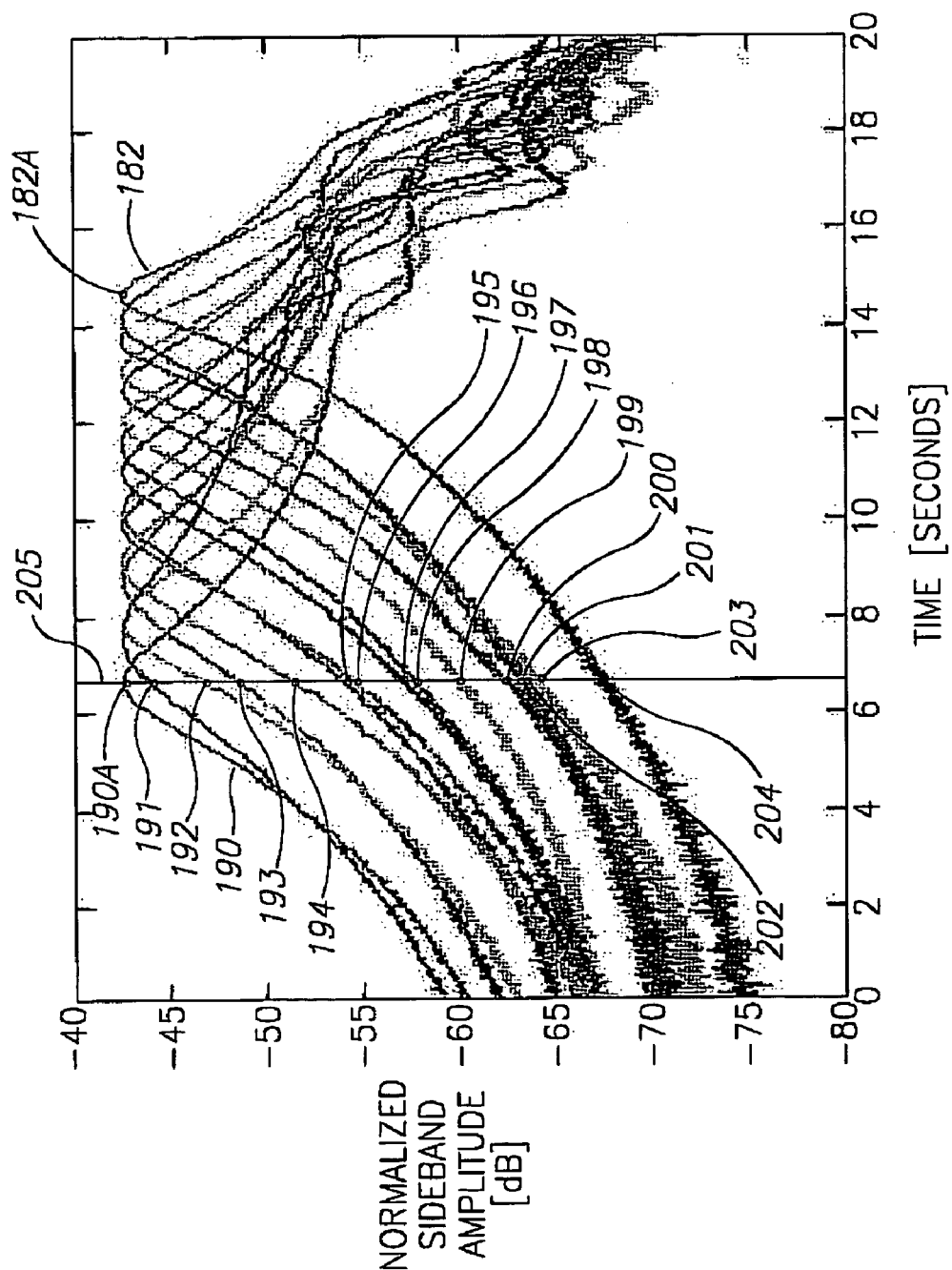
FIG. 15B is a schematic graph illustrating data representing the time dependence of the normalized sideband amplitude for a plurality of different sensor exciting frequencies, obtained by normalizing the data illustrated in FIG. 15A, in accordance with an embodiment of the present invention.

Reference is now briefly made to FIGS. 15A and 15B. FIG. 15A is a schematic graph illustrating an example of non-normalized experimentally obtained data representing the time dependence of the measured sideband amplitude for a plurality of different sensor exciting frequencies.

FIG. 15B is a schematic graph illustrating data representing the time dependence of the normalized sideband amplitude for a plurality of different sensor exciting frequencies, obtained by normalizing the data illustrated in FIG. 15A, in accordance with an embodiment of the present invention.

Turning to FIG. 15A, the experiment was performed using the sensor 20 immersed in water in a pressure chamber, as disclosed hereinabove. A continuous wave transmitted signal was used. The signal included a carrier at 750 KHz and fifteen different sensor exciting frequencies in the range of 50 KHz–64 KHz. The first sensor exciting frequency was 50 KHz and the other fourteen sensor exciting frequencies were equally spaced apart from each other by 1 KHz. Every ten milliseconds, the system sampled four milliseconds of the returning signal. The samples were analyzed (using DFT) to provide frequency domain data as disclosed in detail hereinabove The geometrical mean of the amplitude of both Doppler sidebands was determined as disclosed in detail hereinabove for each of the fifteen sideband amplitudes. The horizontal axis of the graph of FIG. 15A represents time (in seconds) and the vertical axis of the graph represents the mean sideband amplitude. Each of the fifteen curves illustrated in the graph of FIG. 15A represents the mean sideband amplitude data for a single frequency of the fifteen sensor exciting frequencies used.

For example the leftmost curve 180 represents the mean sideband amplitude for the sensor exciting frequency of 64 KHz, and the point 180A of the curve 180 represents the maximal (peak) mean sideband amplitude for the 64 KHz sensor exciting frequency within the 20 seconds duration illustrated in the graph. The other fourteen curves which are incrementally shifted to the right on the time axis with decreasing frequency represent the data for the mean sideband amplitude for the lower sensor exciting frequencies. The rightmost curve 182 represents the mean sideband amplitude for the sensor exciting frequency of 50 KHz. The point 182A of the curve 182 represents the maximal (peak) mean sideband amplitude for the 50 KHz sensor exciting frequency within the 20 seconds duration illustrated in the graph.

As may be seen from the different curves of FIG. 15A, the peak (maximal) values for the different sensor exciting frequencies do not have the same value. For example, the maximum (peak) amplitude of the curve 182 at the point 182A has a value of approximately –42.5 dB, while the maximum (peak) amplitude of the curve 180 at the point 180A has a value of approximately –45.5 dB.

The curves illustrated in FIG. 15A were processed to normalize the curves. The highest peak was the peak of the curve 182 (represented by the point 182A). The difference in dB between this highest amplitude peak and each of the other peaks of each of the curves was computed and for each curve the difference in dB was added to each data point of the curve (besides the curve 182 which was not changed) to bring all the peaks of all the fifteen curves to the same value (in dB).

Turning to FIG. 15B, the fifteen curves of the graph, represent the normalized geometrical mean of the sideband amplitude of the fifteen curves illustrated in FIG. 15A. It is noted that all the peaks of all the normalized curves have identical maximal values of –42.5 dB. It is noted, for example, that the peak amplitude point 190A of the normalized curve 190 is now equal to the peak amplitude point 182A of the curve 180 (The curve 180 has not changed since 0 dB was added to it).

Returning to FIG. 14, the method may now determine at each time point, the sensor's resonance frequency, by finding, for each time point, the sensor exciting frequency having the maximal normalized (or non-normalized if the normalizing step has not been implemented) sideband amplitude (step 168).

For example, returning to the data illustrated in FIG. 15B, the values of the normalized mean sideband amplitude for all the frequencies used in the measurement may now be determined from the normalized curve data. For the exemplary time point schematically represented by the vertical line 205, the amplitudes of the normalized mean sideband frequencies for all of the fifteen sensor exciting frequencies used are given by the points 190A, 191, 192, 193, 194, 195, 196, 197, 198, 199, 200, 201, 202, 203 and 204 at which points the line 205 intersects with each of the fifteen different curves representing the normalized mean sideband amplitude corresponding to the fifteen different sensor exciting frequencies used in the experiment.

The fifteen different values of the normalized mean sideband amplitudes corresponding with the fifteen different sensor exciting frequencies may thus be determined for each time point at which the frequencies amplitude data is computed.

For each time point in the exemplary experiment used to obtain the data shown in FIG. 15A and FIG. 15B, the system has a data set comprising fifteen points, each point has a sensor exciting frequency value and the normalized mean sideband amplitude value corresponding to that sensor exciting frequency. The maximal normalized mean sideband amplitude for each time point may be determined as disclosed hereinabove.

Preferably, a curve (not shown) may be fitted to the fifteen data points and the exciting frequency at which the maximum point of the curve occurs may be determined and as disclosed in detail hereinabove. The computed maximum point frequency may be taken as the sensor's resonance frequency at time point for which the computation was made.

Alternatively, if there is a sufficient number of sensor exciting frequencies used in the measurement, the method may simply use the sensor exciting frequency at which the maximal value of the normalized mean sideband amplitude occurred as the sensor's resonance frequency for that measurement time, as disclosed hereinabove.

Finally, the method may find the pressure value for each time point from the sensor resonance frequency determined for each measurement time point by using the sensor's calibration data (step 170). Furthermore, when the system determines the pressure points for a desired measurement, additional filtering may be used for smoothing and noise removal, and the pressure data may then be displayed to the system's operator.

The resulting computed pressure as a function of time may be displayed on a suitable display device (such as, for example, the display unit 70 of the system 52, or the like). Additionally, the system may optionally compute (if desired) from the acquired (and/or stored) pressure data is desired any other desired parameter of the blood pressure. Such computed parameters may be presented to the operator alphanumerically or graphically or using any other suitable presentation form, as is known in the art.

For example, besides the computing of the blood pulse shape (in real time, or near real time), the system may compute additional pressure related parameters (step 172). Examples of such additional pressure related parameters may include, inter alia, the first derivative of the pressure vs. time curve ($\partial p/\partial t$), the peak blood pressure (per pulse or averaged over a few cycles), the mean blood pressure value (the geometric mean or other type of mean value, as is known in the art), the systolic and/or diastolic pressure (if the sensor is placed in an appropriate part of the cardiovascular system, such as the aorta, or an appropriate cardiac chamber, or other parts for which systolic or diastolic pressures are defined and observable), the pulse pressure (expressed as the difference between the maximum and minimum blood pressure, computed per cycle or averaged over a few cycles), and the like. It is noted that other different pressure related parameters of interest or of clinical or diagnostic relevance may also be computed by the system from the measured pressure data and displayed or otherwise provided as output to a physician or an operator of the system. The computing of such blood pressure related parameters is well known in the art, is not the subject matter of the present invention, and is therefore not disclosed in detail hereinafter All the acquired and/or computed data and/or parameters, or part thereof may also be stored or archived in the system, or may be suitably offloaded from the system for further processing, and/or storage, and/or report generating and/or archiving purposes. The data may also be telemetrically transmitted or sent through any wired or wireless network including but not limited to, the internet, local area networks, virtual private networks, wide area networks, or any other type of computer or communication network, known in the art. Hardcopies of the data may also be generated if required (such as, for example by a suitable printer device included in the user interface 35 of the system 52).

The sensor's calibration data may be in the form of a sensor specific LUT as disclosed in detail hereinabove, or a known sensor calibration function, as disclosed in detail hereinabove.

As disclosed hereinabove, each pressure measurement may consist of one or several sub measurements. The system may transmit several sensor exciting ultrasonic (or sonic) frequencies at the same time or one by one in a serial manner. For each frequency, the software may analyze the amplitude of the Doppler effect, and may search for the sensor exciting frequency at each time point for which the maximum amplitude of the sideband occurs. The blood pressure value may thus be determined for this point of time using the look-up table or other calibration curve or calibration data of the sensor. The measurement process may be repeated fast enough to determine the blood pressure pulse shape.

Assuming that the cycle period of the blood pulse shape is less then 2 Hz (twice a second) we may determine (and, optionally, display) the blood pressure pulsatile shape quite accurately using a pressure measurement rate of approximately 100 Hz (performing a single pressure measurement approximately every 10 milliseconds). However, it is noted that this pressure measurement rate is not obligatory and higher or lower pressure measurement rates may also be used, depending, inter alia, on system and sensor parameters, and on the specific application.

It is, however, noted that this pressure measurement rate is given by way of example only for typical blood pressure measurements, and that different measurement rates may also be used, especially for measurements of pressure in other measurement environment. Generally, the measurement rate may depend, inter alia, on the rate of pressure change in the measurement environment on the desired accuracy, the available ultrasonic beam energy and on other different practical and design considerations which will be obvious to the man skilled in the art, in view of the description of the methods and devices disclosed herein.

Each sensor may have a predefined lookup table (LUT) that defines the relation between the pressure and the resonance frequency. The LUT may be generated by individually calibrating each sensor before implantation. In order to measure the pressure the system measures the resonance frequency and by comparing it to the lookup table the system may determine the pressure for the specific time at which the measurement was made.

The system 50 may be used for pulsatile or fixed pressure applications. For example, in a measurement environment (in-vivo, or in any other non-biological pressure measurement environment) with fixed or slowly varying pressure, it may be possible to use longer integration periods to provide increased accuracy for pressure measurements.

Figure 16:
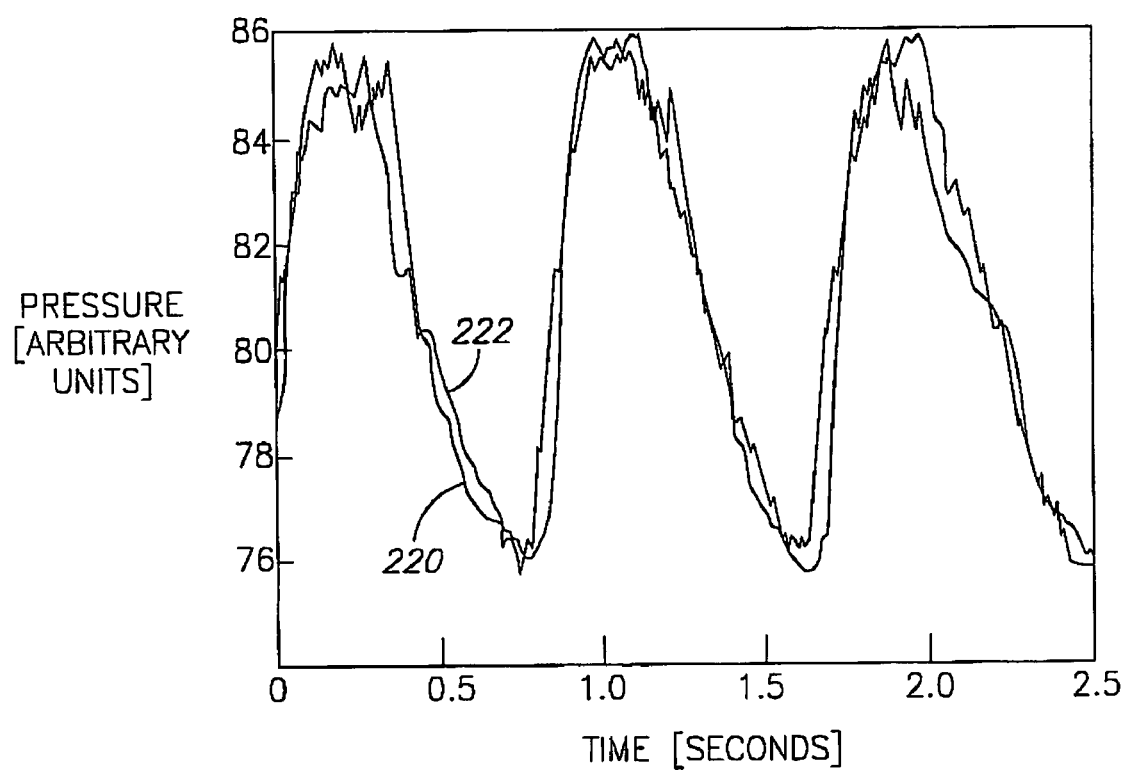
FIG. 16 is a schematic graph illustrating the intraluminal blood pressure in the carotid artery of a pig as determined by simultaneously using an implanted passive ultrasonic sensor with the system 52 of FIG. 5, and an intraluminal pressure measuring catheter.

Reference is now made to FIG. 16 which is a schematic graph illustrating the intraluminal blood pressure in the carotid artery of a pig, determined by simultaneously using an implanted passive ultrasonic sensor with the system 52 of FIG. 5, and an intraluminal pressure measuring catheter. The experiment was performed in an anaesthetized pig. An anchored passive ultrasonic sensor was implanted in the pig's carotid artery. The sensor attached to the anchor was the passive ultrasonic sensor 20 disclosed hereinabove and illustrated in FIGS. 2–3. The sensor's flipping point pressure was at about 900 torr (the sensor was not calibrated prior to performing the implantation). The anchor with the attached sensor was deployed in the pig's carotid artery using the femoral artery access route and a standard dilatation balloon catheter system.

The interrogating beam used in the experiment included a carrier frequency of 2.5 MHz, and all of the sensor exciting frequencies were transmitted simultaneously (using the open loop method disclosed in detail hereinabove) as short, low frequency bursts, each burst having a duration of two milliseconds. The burst repetition frequency was 100 bursts per second (100 Hz). The sensor exciting frequencies were five different discreet frequencies between 83–95 KHz. The returning signals were received and analyzed as disclosed in detail hereinabove to compute pressure data (in arbitrary units, since the sensor used was not pre-calibrated).

After the sensor's implantation, a pressure measurement catheter connected to a Model MX860 mercury IBP pressure transducer (commercially available from Mennen Medical inc., PA, USA.), was introduced into the intraluminal space of the carotid artery of the same pig using standard minimally invasive insertion methods and a femoral artery access route, as is known in the art. The sensor and catheter placement was assisted by standard X-ray imaging and by angiography, as is known in the art. The signal from the MX 860 pressure transducer was fed to an 12 bit A/D board (Model PDA12A, commercially available from Signatec Inc., CA, USA) installed in a 1 GHz Pentium III PC, and processed and displayed on the PC's display unit using software implemented using MATLAB® software. The distal tip of the catheter was placed at the carotid bifurcation, about 3–4 centimeters from the sensor's position. The proximal catheter end was connected to the MX 860 pressure transducer.

The vertical axis of the graph of FIG. 16 represents the blood pressure (in arbitrary units) and the horizontal axis represents time (in seconds). The curve 222 represents the intraluminal blood pressure as measured by the MX 860 pressure transducer (in arbitrary units).

The curve 220 represents the pressure as experimentally determined using the Doppler method of the present invention as disclosed hereinabove using the implanted passive ultrasonic pressure sensor 20.

It is noted that the pressure as measured by the MX 860 pressure transducer is somewhat delayed relative to the actual intraluminal pressure in the carotid bifurcation as determined by the sensor because of the length of the catheter used. Therefore, the pressure curve 222 was manually shifted relative to the curve 220 to compensate for the delay. Furthermore, since the sensor 20 was not calibrated prior to performing the actual measurement shown, the pressure curve 220 was scaled along the vertical pressure axis such that its fill swing peak to peak amplitude visually approximately matched the full swing of the curve 222.

The results illustrated in FIG. 16 indicate that the general shape of the pulsatile blood pressure as determined by the Doppler method (the curve 220) is quite similar to the general shape of the blood pressure (the curve 222) obtained using the intraluminal measurement system using the pressure transducer.

Sensor Identification, Localization, and Centering of the Interrogating Ultrasonic Beam on the Sensor The methods described herein may also solve another problem, which is a direct result of the fact that the transmitted and returned ultrasonic signals are basically at the same frequency and thus the returned signal is "contaminated" by noise and especially by echoes returned from ultrasound reflecting parts or various reflecting interfaces of the human body, as well as by the non-vibratable parts of the sensor itself.

Since most of the energy in the returning signal is at the carrier frequency component and since the signals which contain the desired information at the sensor exciting frequency or frequencies are weak and are contaminated by high noise levels and by echoes at the sensor exciting frequency (or frequencies, if more than one frequency is simultaneously transmitted in the interrogating beam) which may be reflected from structures or reflecting interfaces within the body, it may be difficult to determine if the interrogating beam is suitably directed (or centered) on the implanted sensor(s) by monitoring the intensity of the returning signals at the carrier frequency or at the sensor exciting frequencies.

The inventors of the present invention have noticed that since the sidebands at the relevant Doppler shifted frequencies are present at a substantial energy level only in the signals which are returned from the vibrating parts of the sensor, the presence and the intensity of the Doppler shifted sideband peaks may be used to identify or locate the sensor in the body and to assist the centering of the interrogating ultrasound beam on the sensor(s).

Therefore, in accordance with an embodiment of the present invention, since the sensor reflects the carrier frequency ultrasound signal (with Doppler shift) with much higher amplitude than any tissue in the human body, the identification and localization of the sensor and the centering of the interrogating beam may be performed by searching for a significant Doppler effect in the received signal.

The received returning signal is a superposition of the resonator or vibratable membrane's reflection signal and echoes from other parts of the sensor and from tissues.

The system may analyze the spectrum of the returning signal. If the returning signal has one or more frequency component(s) that is formed due to the Doppler shifting of the carrier frequency and in not just noise and CW echo, the signal should have significant energy at the Doppler sideband frequencies which were modulated by the movement of the resonator or vibratable membrane of the sensor (see, for example the sideband peaks of FIGS. 8 and 10).

When the interrogating beam is centered on the sensor, the amplitude of the Doppler shift sidebands is large enough to be detected. Using an analog front end (such as, for example, the AFE unit 64 of FIG. 7A) more than 30–40 dB signal to noise ratio (SNR) may be achieved at the sideband frequencies. Similarly, if a low noise high dynamic range A/D unit is used to digitize the returning signal and the data is digitally processed, as disclosed in detail hereinabove, the sideband peaks may be detected and their amplitude may be determined.

Thus, if the interrogating beam is scanned across the region in which the sensor is implanted or located, the beam is centered on the sensor when the sideband frequency's amplitude is maximal. If the amplitude of such a Doppler shifted sideband is displayed (such as, for example, on the display unit 70 of the system 50 of FIG. 5) to the user or operator of the system 50, the operator may be able to center the interrogating ultrasound beam on the sensor by scanning the interrogating ultrasound beam across the region in which the sensor is located while monitoring the displayed amplitude of the Doppler shifted sideband frequency and visually determining when the amplitude of the sideband is maximal. The interrogating beam is centered on the sensor at the position and orientation of the transducer(s) unit 62 (or other probe, if used) which results in a maximal amplitude of the Doppler shifted sideband frequency.

It is noted that in accordance with one possible embodiment of the invention, the system may compute an average of the frequency domain data obtained from a few measurements performed within a time period that includes two or more cycles of the blood pressure cycle. Such averaging may be performed to reduce the fluctuations of the amplitude of the sideband frequency or frequencies due to the periodic changes of the sensor's resonance frequency associated with the pressure changes. If this averaging method is used, the user or operator may be provided with a more stable less fluctuating sideband peak(s) that may be more convenient to observe.

It is however, noted that the periodic variations of the sideband(s) amplitude at the blood pulse rate may actually be used by the system as a further indicative characteristic of the signals returning from the vibratable membranes of the sensor and may be actually used to further distinguish the desired signal from noise or spurious echoes at the sideband frequencies. Such use of the rate of sideband amplitude periodic changes is disclosed in detail hereinafter.

When working with pulsatile pressure measurement applications (such as the exemplary measurement of pulsatile blood pressure using an implanted passive ultrasonic pressure sensor), the system may use an additional signal parameter for sensor identification and beam centering. The pulsatile pressure changes the signal amplitude of the Doppler sideband frequency (or frequencies) during the pulse cycle time. These pulsatile pressure induced sideband amplitude changes are present only in the signal reflected from the vibratable membranes of the sensor. Maximizing the amplitude of these pulsatile (periodic) amplitude changes may also be used by the system for sensor identification and for beam centering. Thus, the operator or user of the device may scan the interrogating beam in the region where the implanted sensor is assumed to be positioned and look for the presence of a sideband component (or components) at the expected frequency (or frequencies) having an amplitude which periodically varies in time at a rate similar to the blood pulse rate. In accordance with an embodiment of the invention, the pulsating sideband component may be visually detected on a display device coupled to the system used (such as, for example, on the display unit 70 of the system 50 of FIG. 5) by visually identifying a peak at the expected sideband frequency or frequencies which exhibits periodic amplitude variation at the approximate blood pressure pulsation rate. The interrogating beam may then be centered by carefully changing the beam direction and/or orientation in until the amplitude of the amplitude of the periodically varying sideband is maximal.

Alternatively, since the frequency or frequencies of the sensor exciting frequencies used are known, the system may automatically search for signal components at one or more of the expected sideband frequencies and compute the periodicity of the signal's amplitude variation detected at these frequency components. If the system detects such periodicity at the expected frequency or frequencies, the system may provide the user or operator with a cue or indicative signal, as is known in the art For example, the system may provide a suitable sound signal (audio signal) or visual signal such as a red indicator light, or the like, when a signal is detected that has a periodicity similar to the blood pulse rate and an amplitude above a predefined threshold value. It will be appreciated by those skilled in the art that many permutations and variations of this a detection method may be used. All such variations are considered to be within the scope of the present invention.

Thus, in accordance with one possible embodiment of the present invention, the frequency domain data may be graphically displayed or presented on a suitable display device (such as, but not limited to, the display unit 70 of the system 50 of FIG. 5) to the operator of the system 32 or system 50. The frequency domain graph may be continuously updated as new measurements are performed by the system (for example, if the measurement is repeated every 10 milliseconds, the frequency domain data maybe continuously updated at any rate between 30–100 Hz on the display unit 70, but other updating rates may also be used).

The system's operator may scan the interrogating beam in the region where the sensor(s) may be positioned while observing the changes in the frequency domain graph presented on the display device. When the scanned interrogating beam is directed at the sensor(s), the returning signal will include the Doppler shifted frequencies and sideband peaks will be observed on the frequency domain graphic presentation. Once such sidebands are detected with an amplitude above a certain threshold the operator knows the approximate position of the sensor(s). Optionally, the operator may further verify that the detected sideband signals originate from the sensor by verifying that the amplitude of the detected peak(s) periodically varies in time at a frequency that is similar to the frequency of pulsation of the blood pressure. This variation may be visually observed by the operator since, typically, for human blood pressure the pulse rate may be in the range of about 0.3–1.5 Hz which may be visually detected.

Alternatively, in accordance with another embodiment of the present invention, the rate of amplitude variation at the sideband frequency or frequencies may be automatically detected by the system. If the rate of amplitude variation falls within a predetermined or a preset or a user set range of rates, the system may automatically provide the user with an appropriate signal or cue (such as a suitable audio signal and/or visual signal displayed on the display unit 70 or on any other system user interface device, or by using any other suitable cue or signal known in the art observable by the operator of the system.

The system's operator may then carefully scan the interrogating beam position for fine-tuning the best beam position. The beam's position may be fine tuned or optimized by slowly changing the beam direction and/or orientation until the amplitude of the sideband peak(s) is the maximized. By maximizing the sideband amplitude the operator may ensure a good signal to noise ratio by maximizing the received energy at the sideband frequency or frequencies. Maximizing the amplitude of sideband frequency (or frequencies) may also contribute to improving the SNR and therefore the measurement accuracy and/or the inter-test and/or intra-test accuracy, repeatability and sensitivity. After beam centering, the operator may use the system for determining the blood pressure by determining the resonance frequency of the sensor(s) as disclosed in detail herein and computing the blood pressure from the determined resonance frequency (or frequencies).

Thus, by using information available in the Doppler modulated returning signals, it is possible to detect the sensor's approximate position and to determine when the sensor is suitably centered within the interrogating beam and the beam is properly oriented for obtaining good measurement results.

It will be appreciated by those skilled in the art that while the exemplary methods disclosed hereinabove for sensor identification, detection and for beam centering are based on visual observation by the operator of the sideband peak(s) presence and amplitude, many variations and modifications of the sensor detection and beam positioning methods are possible. For example, in accordance with an embodiment of the present invention, the information about sideband amplitude may be displayed of the display device used using various different display methods instead of, or in addition to, the frequency domain graphic representation. For example, the sideband amplitude may be displayed as a bar having a varying height proportional to the amplitude. Alternatively, or additionally the sideband amplitude or amplitudes may be numerically displayed.

In accordance with yet another embodiment of the invention, other cues such as visual cues or auditory cues, or the like, may be used to notify the operator about the detection of the sensor and/or about proper beam centering and orientation. For example, when the amplitude at the expected sideband frequency or frequencies exceeds a certain level above the averaged noise level, a sound or a visual cue (such as, for example a red LED may light up, or the like) may be activated, or the like, signifying that the sensor(s) has been detected. Similar or other methods may be used as is known in the art to indicate to the system's operator or user when the beam is properly oriented and centered on the sensor(s).

In accordance with another embodiment of the invention, the sensor detection and beam centering and orientation may be partially or fully automated by using an automated or robotic controllable probe scanner (not shown) coupled with suitable software for systematically scanning the ultrasonic probe and for sensor detection and for optimizing the beam orientation and direction and the measurements signal to noise ratio, based on the amplitude of the sideband frequency or frequencies.

Pressure Measurements at Different Altitudes

The absolute blood pressure values depend on the atmospheric pressure at the measurement site. This measurement may be performed at different geographical locations which may be at different altitudes (relative to sea level) and therefore at different absolute atmospheric pressures. While in geographical locations at or near sea level the blood pressure is typically measured relative to 760 torr, other geographical locations at higher altitudes and, therefore, lower external (barometric) pressure levels may measure significantly smaller absolute blood pressure values.

Typically, the external pressure variation range due to different altitudes over which blood pressure measurements may need to be performed may be between 600–900 torr.

Thus, preferably, the measuring system needs to adapt itself to the site's altitude. At each altitude the sensor should be able to be operated at a different pressure range that is a small portion of the entire pressure range covered by the sensor. The system thus may implement algorithms for finding the specific low frequency (resonator exciting frequencies) range optimal for the measurement at any specific altitude.

For example, the system may first use an interrogating beam containing selected frequencies over the full possible sensor exciting frequency spectrum range, and search for those frequencies that cause the sensor to resonate at the specific pressure range (by comparing the sideband amplitudes for these transmitted frequencies). The system may then refine the search by interrogating the sensor using a group of frequencies selected within a frequency range closer to the frequency that was found in the first interrogation to have the maximal sideband amplitude. This search refining procedure may be repeated more than once. The system may thus select a set of sensor exciting frequencies suitable for use at the particular external pressure.

Practically, it may be possible to perform blood pressure measurements over the required external pressure range by using few alternative approaches. In accordance with one possible embodiment of the invention, the implanted sensor may have an extended pressure working range to cover all or most possible external pressure variations due to performing the measurements at different altitudes.

In accordance with another embodiment of the invention, several sensors may be implanted in the patient, and each sensor may have a different working pressure range. The different sensors' working pressure ranges may overlap to adequately cover a desired working pressure range.

The system of the present invention (such as, but not limited to, the system 38 or the system 50) may include a pressure measuring device (such as, but not limited to, the barometer unit 37 of FIG. 4, or any other suitable pressure measuring device known in the art for measuring the external pressure) which may determine the external pressure level and provide the external pressure data to the system. This data may be used by the system (such as but not limited to the system 32 of FIG. 4) to determine which is the appropriate sensor for performing the pressure measurement (if multiples sensors are available). The system may then automatically select, based on the measured external pressure data, the appropriate set of sensor exciting frequencies to be used for interrogating the selected sensor.

If a single wide-range sensor is used by the system, the external pressure data may also be used by the system for determining the appropriate set of sensor exciting frequencies to be used with the wide range sensor.

The measured external pressure determined by the barometer unit 37 of the system (or by any other suitable external pressure determining device used by the system) may also be used for computing the gage pressure. The gage pressure may be computed as the difference between the absolute pressure (relative to vacuum) and the external pressure measured by the external pressure-determining device of the system (such as, but not limited to the barometer unit 37 of FIG. 4). The computed gage pressure may be a more convenient way for presenting the pressure measurement results of the system to a physician or other users of the system.

It is noted that while most of the examples disclosed hereinabove are adapted for determining pressure using passive ultrasonic pressure sensitive resonating sensors, the novel Doppler based methods and systems shown herein may be implemented and adapted for determining the resonance frequency of any type of resonator. Thus, the scope of the present invention includes the use of a sonic beam including a carrier frequency and one or more resonator exciting frequencies for determining the resonance frequency of any resonator. The methods and systems of the present invention may therefore also be used to determine the resonance frequency of a resonator which is not used as a sensor.

While the invention has been described with respect to a limited number of embodiments, it will be appreciated that many variations, modifications and other applications of the invention may be made which are within the scope and spirit of the invention.

Doppler Effect Review

The mathematical and physical models, and method to evaluate the Doppler shift are described herein. The mathematical equations for the FM model are given in APPENDIX A filed herewith.

When a transmitted signal hits a moving object (such as, for example, the vibratable membrane of a resonating sensor as disclosed hereinabove) and reflects back to the origin, the returning signal changes its frequency. This is known as the Doppler effect.

If the object is moving away from the source, the returning cycle needs more time than the origin cycle, so the actual frequency would be lower. If the object is moving in the opposite direction the returning frequency would be higher.

The change in the frequency—$f_{Doppler}$, may be expressed as:

$$f_{Doppler} = f_{mod} \cdot \frac{2v}{c-v} \cdot \cos(\varphi) \qquad (2)$$

Wherein:
$f_{Doppler}$—is the Doppler shift
$f_{mod}$—is the source frequency
c—is the propagation speed of sound in the medium
v—is the object's velocity
φ—is the angle between the signal and the object plain Since c>>v and since for a beam nearly orthogonal to the object's surface φ~0, equation (2) above reduces to equation (3) below:

$$f_{Doppler} = f_{mod} \cdot \frac{2v}{c} \qquad (3)$$

Physical Model

When the Doppler effect method of the present invention is used, a high (carrier) frequency and a lower (resonator exciting) frequency are transmitted at the same time. The lower frequency oscillates the sensor's resonator or vibratable membrane that acts as the moving object. The higher carrier frequency does not substantially affect the membrane movement because it's far away from the resonance frequency. The high carrier frequency is therefore modulated by the lower frequency of the vibratable membrane according to the Doppler phenomenon.

The resonance frequency of the membrane changes according to the blood pressure. For a given sensor exciting frequency having a given amplitude, the changes in the sensor's resonance frequency vary the amplitude of the membrane's oscillations in response to the exciting frequency. Therefore, the amplitude measured at the Doppler shifted frequency also changes in accordance with the pressure variation.

The Mathematical Model $f_{low}$—is the low (resonator exciting) frequency
$f_{mod}$—is the high (carrier) frequency
$f_{Doppler}$—is the Doppler frequency shift
$f_{Doppler\ max}$—is the Maximum Doppler frequency shift
$A_{sensor}$—is the maximum amplitude of the vibratable membrane (of the resonator or sensor). $A_{sensor}$ depends on the difference between the sensor's resonance frequency and the low frequency used for excitation of the vibratable membrane (or other resonating part of the sensor).
x(t)—is the maximum deflection point of the membrane as function of time (see FIGS. 1A–1C).

$$x(t) = A_{sensor(f_{resonance}, f_{low})} \cdot \cos(w_{low} \cdot t) \quad (4)$$

wherein, $w_{low}$—is the angular frequency (in radians per time units) of the low (resonator exciting) frequency.
v(t)—is the membrane velocity as a function of time.

$$c = 1540 \text{ (m/s)}$$

$$v(t) = \frac{\partial x}{\partial t} = -A_{sensor} \cdot w_{low} \cdot \sin(w_{low} \cdot t)$$

$$f_{Doppler} = f_{mod} \cdot \frac{2v}{c} \quad (5)$$

The maximum Doppler frequency shift $f_{Doppler\ max}$ is given as:

$$f_{Doppler\ max} = f_{mod} \cdot \frac{2v_{max}}{c} \quad (6)$$

$$f(t) = f_{mod} + f_{Doppler\ max} \cdot \sin(w_{low} \cdot t) \quad (7)$$

$$w(t) = w_{mod} + w_{Doppler\ max} \cdot \sin(w_{low} \cdot t) \quad (8)$$

$$\phi(t) = w_{mod} \cdot t - \frac{w_{Doppler\ max}}{w_{low}} \cdot \cos(w_{low} \cdot t) \quad (9)$$

$$y(t) = A_y \cdot \cos(\phi) \quad (10)$$

wherein, $f_{Doppler\ max}$ is the maximum Doppler shift frequency
$v_{max}$ is the maximal vibratable membrane velocity
f(t) is the temporal frequency of the returned signal
w(t) is the temporal angular frequency of the returned signal
$w_{mod}$ is the angular carrier frequency
$w_{Doppler\ max}$ is the maximum temporal angular Doppler frequency (in radians per time unit).
φ(t) is the temporal phase of the returned signal
y(t) is the modulated signal; and
Ay is the amplitude of the modulated signal Examplary Calculation An exemplary calculation of the Doppler effects may be made using specific (and non-limiting) exemplary values of the parameters. If we select the following values: $f_{low}$=50 MHz, $f_{mod}$=5 MHz, $A_{sensor}$=1 micrometer, and c=1540(m/s)

Then, $$f_{Doppler\ max} = f_{mod} \cdot \frac{2v_{max}}{c} \quad (11)$$

$$= f_{mod} \cdot \frac{2 \cdot A_{sensor} \cdot w_{low}}{c}$$

$$= \frac{5 \cdot 10^6 \cdot 2 \cdot 10^{-6} \cdot 2 \cdot \pi \cdot 50 \cdot 10^3}{1540}$$

$$= 2.04 \text{ KHz}$$

Thus, the maximum frequency shift due to the Doppler shifting is 2.04 KHz

References of Interest

1. "Communication systems" (4$^{th}$ edition) by Simon Haykin, published by John Williams & Sons, 2001.

AppendixA

Mathematical Model Equations Using FM Model $\beta = \Delta f / f_m$ $y_{(t)} = A \cos(w_0 t + \phi_{(t)}) = A \cos(\theta_{(t)})$ $\phi_{(t)} = \beta \sin(w_m t)$ $\theta_{(t)} = w_0 t + \Phi_{(t)}$ $w_{(t)} = w_0 + \delta \Phi / \delta t = w_0 + \beta w_m \cos(w_m t) = w_0 + 2\pi \Delta f \cos(w_m t)$ $y_{(t)} = A \cos(w_0 t + \beta \sin(w_m t)) =$ $= A[\cos(\beta \sin(w_m t)) * \cos(w_0 t) - \sin(\beta \sin(w_m t)) * \sin(w_0 t)]$ It can be seen in the Simon Haykin reference cited above that for narrow band FM (β<<1)

$y_{(t)} = A[\cos(w_0 t) - \beta \sin(w_m t) * \sin(w_0 t)]$ and $A_{(w_0+w_m)} / A_{(w_0)} = \beta/2$ Where $\beta = 4\pi A f_0 / c$ wherein, $A_{(w_0)}$—is the Amplitude of the carrier wave
$A_{(w_0+w_m)}$—is the amplitude of the side frequency
β is the modulation index
Δf is the frequency deviation
$f_m$ is the modulation frequency
$f_0$ is the carrier frequency
$w_m$ is the modulation angular frequency
$w_0$ is the carrier angular frequency
$w_{(t)}$ is the temporal angular frequency
$y_{(t)}$ is the FM signal as a function of time
A is the amplitude of the FM signal

The invention claimed is:

1. A method for determining the resonance frequency of a vibratable resonator, the method comprising the steps of:
    subjecting said resonator to a sonic beam having one or more resonator exciting frequencies for exciting vibrations of said vibratable resonator and a carrier frequency capable of being frequency modulated by vibrations of said vibratable resonator, said carrier frequency is higher than said one or more resonator exciting frequencies;
    receiving returning signals from said vibratable resonator; and
    processing said returning signals to determine the resonance frequency of said vibratable resonator, wherein said step of processing comprises the steps of processing said returning signals to determine for each exciting frequency of said one or more resonator exciting frequencies the amplitude of at least one Doppler shifted frequency component of said carrier frequency to obtain a set of amplitude and frequency data points, and computing from said set of amplitude and frequency data points the resonance frequency of said vibratable resonator, and wherein said resonator exciting frequencies are frequencies in the vicinity of the resonance frequency of said vibratable resonator.

2. The method according to claim 1 further comprising the step of detecting the presence of said vibratable resonator within said sonic beam based on the amplitude of said at least one Doppler shifted frequency component of said carrier frequency.

3. The method according to claim 2 wherein said step of detecting comprises providing a signal indicating the presence of said resonator in said sonic beam when the amplitude of said at least one Doppler shifted frequency component exceeds a threshold value.

4. The method according to claim 3 wherein said step of detecting is performed automatically.

5. The method according to claim 2 wherein said resonator is a passive ultrasonic pressure sensor implanted within a cardiovascular system having a periodically varying blood pressure therein, and wherein said step of detecting comprises detecting the presence of said resonator in said sonic beam when the amplitude of said at least one Doppler shifted frequency component exceeds a threshold value.

6. The method according to claim 5 wherein said step of detecting further comprises detecting the presence of said resonator in said sonic beam when the amplitude of said at least one Doppler shifted frequency component periodically varies at a rate substantially similar to the rate of periodic varying of said blood pressure.

7. The method according to claim 2 wherein said resonator is a passive ultrasonic pressure sensor implanted within a cardiovascular system having a periodically varying blood pressure therein, and wherein said step of detecting comprises detecting the presence of said resonator in said sonic beam when the amplitude of said at least one Doppler shifted frequency component exceeds a threshold value and varies periodically at a rate substantially similar to the rate of periodic varying of said blood pressure.

8. The method according to claim 2 wherein said step of detecting comprises providing to a user performing said method a signal indicative of the amplitude of said at least one Doppler shifted frequency component.

9. The method according to claim 8 wherein the signal indicative of the amplitude of said at least one Doppler shifted frequency component is selected from, an auditory signal, a visual signal and combinations thereof.

10. The method according to claim 8 wherein the signal indicative of the amplitude of said at least one Doppler shifted frequency component is selected from,
    a visual signal representing the real time variation of a frequency domain representation of said returning signals,
    a visual signal representing the real time variation of the amplitude of said at least one Doppler shifted frequency component,
    a visual signal displayed when the amplitude of said at least one Doppler shifted frequency component exceeds a threshold level,
    an audio signal having a perceptible varying characteristic which is correlated to the variation of the amplitude of said at least one Doppler shifted frequency component, and
    an audio signal initiated when the amplitude of said at least one Doppler shifted frequency component exceeds a threshold level.

11. The method according to claim 1 further comprising the step of centering said sonic beam on said vibratable resonator based on the amplitude of said at least one Doppler shifted frequency component of said carrier frequency.

12. The method according to claim 11 wherein said step of centering comprises redirecting said sonic beam to maximize the amplitude of said at least one Doppler shifted frequency component.

13. The method according to claim 12 wherein said redirecting comprises automatically redirecting said sonic beam to maximize the amplitude of said at least one Doppler shifted frequency component.

14. The method according to claim 1 wherein said step of processing comprises the steps of:
    processing said returning signals to obtain a frequency domain representation of said returning signals comprising a plurality of amplitude peaks at a plurality of frequencies representing Doppler shifted frequencies of said carrier frequency;
    determining the amplitude values of said plurality of amplitude peaks at said Doppler shifted frequencies to obtain a set of amplitude and frequency data points; and
    computing from said set of amplitude and frequency data points the resonance frequency of said vibratable resonator.

15. The method according to claim 14 wherein said step of computing comprises fitting a curve to said set of amplitude and frequency data points, and computing the resonance frequency of said resonator as the frequency of said curve at which the amplitude of said curve has a maximum.

16. The method according to claim 14 wherein said step of computing comprises computing the resonance frequency of said resonator as the frequency of said set of amplitude and frequency data points having the maximal amplitude.

17. The method according to claim 14 wherein for each frequency of said one or more resonator exciting frequencies, the amplitude peak value is obtained from the amplitude of at least one frequency-domain sideband associated with the sensor exciting frequency by a step selected from the steps of,
    computing the amplitude peak as the sideband amplitude of a single sideband selected from the pair of sidebands associated with each sensor exciting frequency, computing the amplitude peak as a mean sideband amplitude by computing the arithmetic mean of the pair of sidebands associated with each sensor exciting frequency, computing the amplitude peak as a mean sideband amplitude by computing the geometrical mean of the pair of sidebands associated with each sensor exciting frequency.

18. The method according to claim 1 wherein said sonic beam is selected from a continuous wave beam, a chirped beam, and a beam having at least one frequency burst.

19. The method according to claim 18 wherein said sonic beam comprises a plurality of sonic frequency bursts and wherein said frequency bursts are selected from a plurality of contiguous frequency bursts and a plurality of frequency bursts separated by silent time periods.

20. The method according to claim 18 wherein said sonic beam comprises a plurality of sonic frequency bursts and wherein said frequency bursts are selected from bursts having the same burst duration and a bursts having different burst durations.

21. The method according to claim 18 wherein said sonic beam comprises a plurality of sonic frequency bursts and wherein all the resonator exciting frequencies of said one or more resonator exciting frequencies are included in each burst of said plurality of sonic bursts.

22. The method according to claim 18 wherein said sonic beam comprises a sequential series of sonic frequency bursts and wherein each burst of said series of sonic frequency bursts comprises a different single resonator exciting frequency of said one or more resonator exciting frequencies, said series of sonic bursts includes all the resonator exciting frequencies of said one or more of resonator exciting frequencies required for performing a single measurement of said resonance frequency.

23. The method according to claim 22 wherein said carrier frequency of said sonic beam is selected from a continuously transmitted carrier frequency and a pulsed carrier frequency.

24. The method according to claim 18 wherein said sonic beam comprises a sequential series of sonic frequency bursts and wherein a single burst of said series of sonic frequency bursts comprises a subgroup of resonator exciting frequency of said one or more resonator exciting frequencies, said series of sonic bursts includes all the resonator exciting frequencies of said one or more resonator exciting frequencies required for performing a single measurement of said resonance frequency.

25. The method according to claim 24 wherein said carrier frequency of said sonic beam is selected from a continuously transmitted carrier frequency and a pulsed carrier frequency.

26. The method according to claim 18 wherein said sonic beam comprises a continuous wave at said carrier frequency and one or more sonic frequency bursts each burst of said one or more frequency bursts includes one or more sensor exciting frequencies.

27. The method according to claim 18 wherein said sonic beam comprises one or more sonic frequency bursts each burst having a burst duration including said carrier_frequency and at least one sensor exciting frequency, and wherein said returning signals are sampled only within part of said burst duration.

28. The method according to claim 18 wherein said sonic beam comprises one or more sonic frequency bursts each burst having a burst duration including said carrier frequency and at least one sensor exciting frequency, and wherein said returning signals are sampled to obtain sampled data, wherein only a part of the sampled data corresponding to a portion of said burst duration is processed in said step of processing.

29. The method according to claim 18 wherein the measuring of a single pressure point comprises transmitting a single sonic frequency burst including said carrier frequency and said one or more resonator exciting frequencies.

30. The method according to claim 1 wherein said sonic beam is selected from a sound beam and an ultrasound beam.

31. The method according to claim 1 wherein said vibratable resonator is a resonating pressure sensor.

32. The method according to claim 1 wherein said vibratable resonator is a resonating pressure sensor disposed in a pressure measurement environment having a varying pressure therein, the resonance frequency of said pressure sensor varies with the pressure in said measurement environment.

33. The method according to claim 32, wherein said resonating pressure sensor is selected from a passive resonating pressure sensor, and a passive ultrasonic resonating pressure sensor.

34. The method according to claim 33, wherein said passive resonating pressure sensor, and said passive ultrasonic resonating pressure sensor are calibratable pressure sensors.

35. The method according to claim 34, wherein said step of processing further includes the step of determining the pressure in said measurement environment from the determined resonance frequency of said resonating pressure sensor.

36. The method according to claim 35, wherein said step of determining the pressure in said measurement environment comprises computing said pressure from said resonance frequency using calibration data of said resonating pressure sensor.

37. The method according to claim 36, wherein said calibration data is selected from,
 a lookup table including resonance frequency values of said sensor and the corresponding pressure values at which said resonance frequency values where empirically determined, and
 a computed calibration function for computing pressure values from determined values of said resonance frequency.

38. The method according to claim 32, further including the step of determining the external barometric pressure in the region in which the measurement is performed.

39. The method according to claim 38, further including the step of selecting from a plurality of sensors disposed in a measurement environment and having various different pressure working ranges, an appropriate sensor for performing a pressure measurement in said pressure measurement environment, based on said external barometric pressure.

40. The method according to claim 38, wherein said resonating pressure sensor is a wide range resonating pressure sensor, and wherein said method further includes the step of determining a set of sensor exciting frequencies to be used in said sonic beam, based on said external barometric pressure.

41. The method according to claim 38, further including the step of automatically selecting, based on said external barometric pressure, a set of sensor exciting frequencies to be used in said sonic beam.

42. The method according to claim 1, wherein said sonic beam comprises a plurality of measurement periods, each measurement period of said plurality of measurement periods comprises one or more frequency bursts, and wherein the plurality of the resonator exciting frequencies included in said one or more frequency bursts is identical in all of said measurement periods.

43. The method according to claim 1 wherein said sonic beam comprises a plurality of sequential measurement periods, each measurement period of said plurality of measurement periods comprises one or more frequency bursts, and wherein the plurality of the resonator exciting frequencies included in said one or more frequency bursts varies for different measurement periods of said plurality of measurement periods.

44. The method according to claim 43 wherein said vibratable resonator is a resonating pressure sensor disposed in a measurement environment having a varying pressure therein, the resonance frequency of said pressure sensor varies with the pressure in said measurement environment, and wherein the frequency values of the resonator exciting frequencies included in the current measurement period are determined based on a predicted value of the resonance frequency of said pressure sensor for the measurement period following the current measurement period.

45. The method according to claim 44 wherein said varying pressure is a periodically varying pressure having a plurality of cycles, and wherein said predicted value of said resonance frequency is determined based on test data obtained in measurements preceding the time of determining of said predicted value.

46. The method according to claim 45 wherein said test data comprises data obtained by measurements of the resonance frequency of said sensor in measurements preceding the time of determining of said predicted value.

47. The method according to claim 46 wherein said test data comprises data obtained by performing a plurality of measurements using a fixed set of sensor exciting frequencies prior to obtaining said predicted value of the resonance frequency of said pressure sensor.

48. The method according to claim 46 wherein said test data comprises data obtained from a plurality of sensor's resonance frequency data cycles determined in a plurality of said cycles.

49. The method according to claim 48 wherein said test data comprises data selected from,
  data representing the range of the sensor's resonance frequency values obtained in measurements taken at similar time points within each cycle of said plurality cycles,
  data representing the mean sensor's resonance frequency obtained for all the measurements taken at similar time points within each cycle of said plurality of cycles, and
  data representing the mean and the standard deviation of the sensor's resonance frequency obtained for all the measurements taken at a similar time within each cycle of said plurality of cycles.

50. The method according to claim 45 wherein said measurement environment is a part of the cardiovascular system of a patient, said periodically varying pressure is the blood pressure within said part of said cardiovascular system, and wherein the time point of the resonance frequency determined by said current measurement is determined from an independently measured synchronizing signal.

51. The method according to claim 50 wherein said independently measured synchronizing signal comprises a biological signal associated with activity of said cardiovascular system or of a part thereof.

52. The method according to claim 50 wherein said independently measured synchronizing signal is associated with cardiac activity of said patient.

53. The method according to claim 50 wherein said independently measured synchronizing signal is selected from an electrocardiogram signal of said patient, and an acoustic signal associated with the mechanical beating of the heart of said patient.

54. The method according to claim 50 wherein the timing within the duration of the current resonance frequency cycle of the resonance frequency value determined by said current measurement is determined relative to a selected part of an electrocardiogram signal simultaneously recorded from said patient.

55. A system for determining the resonance frequency of a vibratable resonator, the system comprising:
  transmitting means configured for directing at said vibratable resonator a sonic beam comprising one or more resonator exciting frequencies and a carrier frequency higher than said one or more exciting frequencies;
  receiving means configured for receiving signals returning from said vibratable resonator; and
  processing means operatively coupled to said transmitting means and to said receiving means, said processing means is configured for processing said signals to obtain data representing the amplitude of said signals at frequencies representing Doppler shifted frequency components of said carrier frequency and for determining the resonance frequency of said vibratable resonator from said data.

56. The system according to claim 55 wherein said processing means is configured for controlling the operation of said transmitting means and of said receiving means.

57. The system according to claim 55 wherein said vibratable resonator is a passive ultrasonic vibratable pressure sensor disposed in a measurement environment and wherein said processing means is configured for determining the pressure in said measurement environment from said resonance frequency.

58. The system according to claim 57 wherein said transmitting means comprises at least one frequency generating unit operatively coupled to at least one transducer unit for generating said sonic beam.

59. The system according to claim 57 wherein said receiving means comprises at least one transducer unit for receiving signals returning from said vibratable resonator.

60. The system according to claim 59 wherein said processing means is selected from at least one processing unit, at least one controlling unit, and at least one processing and controlling unit.

61. The system according to claim 57 wherein said system further comprises pressure determining means for determining the external pressure level in the vicinity of said system.

62. The system according to claim 57 wherein said system further comprises interfacing means selected from means for allowing a user to control said system, means for presenting data to an operator or user of said system, and a combination thereof.

63. A system for determining the resonance frequency of a vibratable resonator, the system comprising:
  a transmitter unit configured for directing at said vibratable resonator a sonic beam comprising one or more resonator exciting frequencies and a carrier frequency higher than said one or more resonator exciting frequencies;
  a receiver unit configured for receiving signals returning from said vibratable resonator; and
  a processing unit operatively coupled to said transmitter unit and to said receiver unit, said processing unit is configured for processing said signals to obtain data representing the amplitude of said signals at frequencies representing Doppler shifted frequency components of said carrier frequency and for determining the resonance frequency of said vibratable resonator from said data.

64. The system according to claim 63 wherein said vibratable resonator is a passive ultrasonic vibratable pressure sensor disposed in a measurement environment and wherein said processing unit is configured for determining the pressure in said measurement environment from said resonance frequency.

65. The system according to claim 63, wherein said processing unit is configured for determining the external pressure in the region in which the measurement is performed.

66. The system according to claim 65, wherein said processing unit is configured for selecting from a plurality of sensors disposed in a measurement environment and having various different pressure working ranges, an appropriate sensor for performing a pressure measurement in said pressure measurement environment, based on said external pressure.

67. The system according to claim 65, wherein said resonating pressure sensor is a wide range resonating pressure sensor, and wherein said processing unit is configured for determining a set of sensor exciting frequencies to be used in said sonic beam, based on said external pressure.

68. The system according to claim 65, wherein said processing unit is configured for automatically selecting, based on said external pressure, a set of sensor exciting frequencies to be used in said sonic beam.

69. The system according to claim 63 wherein said processing unit is configured for controlling the operation of said transmitter unit and said receiver unit.

70. The system according to claim 63 wherein said transmitter unit and said receiver unit are included in a transceiver unit operatively coupled to said processing unit.

71. The system according to claim 63 wherein said transmitter unit comprises,
a frequency generating unit for generating said carrier frequency and said one or more resonator exciting frequencies, and
a transducers unit operatively coupled to said frequency generating unit for transmitting said sonic beam.

72. The system according to claim 71 wherein said frequency generating unit comprises,
a high frequency generating unit for generating said carrier frequency, and
a low frequency generating unit for generating said one or more resonator exciting frequencies.

73. The system according to claim 71 wherein said transducers unit comprises one or more transducer units selected from, piezoelectric transducers, electromechanical transducers, electromagnetic transducers, capacitive transducers, electro-magneto-mechanical transducers and any combinations thereof.

74. The system according to claim 73 wherein said one or more transducer units comprise one or more piezoelectric transducers selected from, single-element piezoelectric transducers, multi-element piezoelectric transducers, nested piezoelectric transducers, coaxial concentric piezoelectric transducers, phased piezoelectric transducer arrays, and any combinations thereof.

75. The system according to claim 73 wherein said one or more transducer units comprise a wideband capacitive transducer for transmitting said carrier frequency and said one or more resonator exciting frequencies.

76. The system according to claim 73 wherein said one or more transducer units comprise a first piezoelectric transducer for transmitting said carrier frequency and a second piezoelectric transducer for transmitting said one or more resonator exciting frequencies.

77. The system according to claim 71 wherein said frequency generating unit is configured for generating any frequency selected from said carrier frequency and said one or more resonator exciting frequencies, in a form selected from a continuous wave frequency, one or more frequency pulses, one or more frequency bursts including a plurality of different frequencies and one or more chirped frequency sweeps.

78. The system according to claim 63 wherein said receiver unit comprises a frequency modulation receiver.

79. The system according to claim 63 wherein said frequency modulation receiver is selected from a baseband receiver unit and an intermediate frequency receiver unit.

80. The system according to claim 63 wherein said receiver unit comprises at least one receiving transducer for receiving said returning signals and for providing an output signal representing said returning signals.

81. The system according to claim 80 wherein said receiver unit further comprises an analog front end unit operatively coupled to said at least one receiving transducer for receiving said output signal from said at least one receiving transducer and for processing said output signal to provide a processed analog output signal, and an analog to digital converter unit operatively coupled to said analog front end unit and to said processing unit for digitizing said processed analog output signal and for providing a digitized signal to said processing unit.

82. The system according to claim 81 wherein said analog front end unit is configured for processing the output signal received from said at least one receiving transducer, wherein said processing is selected from, filtering the received signal to remove noise and undesired frequency components, amplifying the received signal to provide an amplified signal, mixing the signal with a reference signal to provide a mixed analog signal, filtering said mixed analog signal for removing undesired frequency components of said mixed analog signal to provide a down-converted analog signal, amplifying said down-converted analog signal, and combinations thereof.

83. The system according to claim 80 wherein said receiver unit further comprises an analog to digital converting unit operatively coupled to said at least one receiving transducer for digitizing the signal received from said at least one receiving transducer unit to provide a digitized signal.

84. The system according to claim 63 wherein said receiver unit is configured for down-converting the signal received from said at least one receiving transducer to provide a down converted signal.

85. The system according to claim 84 wherein said receiver unit is configured for processing said down converted signal to remove undesired frequency components therefrom to provide a filtered down-converted signal.

86. The system according to claim 85 wherein said receiver unit is configured for amplifying said filtered down-converted signal to provide an amplified filtered down-converted signal.

87. The system according to claim 63 wherein said system further comprises a synchronizing unit operatively coupled to said transmitting unit and said receiver unit, for synchronizing the operation of said transmitting unit and said receiver unit.

88. The system according to claim 87 wherein said synchronizing unit is operatively coupled to said processing unit.

89. The system according to claim 87 wherein said synchronizing unit is configured for receiving an external synchronizing signal.

90. The system according to claim 63 wherein said system is configured to condition said signals for providing said processing unit with a conditioned signal.

91. The system according to claim 90 wherein said system is configured to condition said signals by performing on said signals one or more operations selected from pre-amplification, band pass filtering, multiplication by a reference signal, low pass filtering, notch filtering, amplification, and combinations thereof.

92. The system according to claim 90 wherein said system is configured to condition said signals by performing on said signals the procedures of bandpass filtering, pre-amplification, bandpass filtering, multiplication by a reference signal, low pass filtering, notch filtering, and amplification.

93. The system according to claim 92 wherein said procedures are performed on said signals in the order recited in claim 92.

94. The system according to claim 63 wherein said system is configured to process said signals to obtain digitized data, and perform on said digitized data a digital Fourier transform to obtain frequency domain data representing signal amplitude as a function of frequency.

95. The system according to claim 63 wherein said processing unit comprises at least one unit selected from, a computer, a microcomputer, a microprocessor, a digital processor, a digital signal processor, a microcontroller unit, a controller unit, a personal computer, a workstation, a minicomputer, a networked computer, a mainframe computer, a distributed processor configuration, a computer cluster configuration, and combinations thereof.

96. The system according to claim 63 wherein said system is configured as part of a medical ultrasound imaging system.

97. The system according to claim 63 further comprising a high dynamic range analog to digital converting unit operatively connected to said receiver unit for receiving an analog signal from said receiver unit, said analog to digital converting unit is operatively connected to said processing unit and is configured for digitizing said analog signal to provide a digitized signal to said processing unit.

98. The system according to claim 63 wherein said system further comprises an analog front end unit and an analog to digital converting unit, said analog front end unit is operatively connected to said receiver unit to receive signals therefrom, said analog front end unit is operatively connected to said analog to digital converting unit and is configured for providing a conditioned analog output signal to said analog to digital converting unit, said analog to digital converting unit is operatively connected to said at least one processing unit to provide a digitized signal thereto.

99. The system according to claim 98 wherein said analog front end unit comprises a frequency down-converting unit for down-converting the signals received from said receiver unit.

100. The system according to claim 99 wherein said frequency down-converting unit comprises a mixer unit configured for receiving an analog signal, and a reference signal source operatively connected to said mixer unit for providing a reference signal to said mixer unit, said mixer unit is configured to mix said analog signal with said reference signal.

101. The system according to claim 100 wherein said analog front end unit comprises at least one signal conditioning unit operatively connected to said receiver unit for receiving signals from said receiver unit, said at least one conditioning unit is operatively connected to said mixer unit for providing a conditioned signal to said mixer unit.

102. The system according to claim 101 wherein said at least one signal conditioning unit comprises at least one filter unit for filtering the signals received from said receiver unit and at least one amplifier unit.

103. The system according to claim 102 wherein said at least one filter unit comprises a first band pass filter unit operatively connected to said receiver unit and to said at least one amplifier unit, and a second band pass filter unit operatively connected to said at least one amplifier unit for filtering the output of said at least one amplifier unit, said second band pass filter unit is operatively connected to said mixer unit.

104. The system according to claim 100 wherein said analog front end unit comprises a post mixing signal conditioning unit operatively connected to said mixer unit for receiving signals from said mixer unit, said post mixing signal conditioning unit is operatively connected to said analog to digital converting unit for providing a down-converted signal to said analog to digital converting unit.

105. The system according to claim 104 wherein said post mixing signal conditioning unit comprises a filter unit selected from a low pass filter, a notch filter, and a combination thereof.

106. The system according to claim 105 wherein said post mixing signal conditioning unit also comprises an amplifier operatively coupled to the filter unit of said down-converting unit.

107. The system according to claim 98 wherein said analog front end unit comprises,
a first filter unit operatively connected to said receiver unit for filtering signals received from said receiver unit to provide a first filtered signal,
a first amplifier unit operatively connected to said first filter unit for amplifying said first filtered signal to provide a first amplified signal,
a second filter unit operatively connected to said first amplifier unit for filtering said first amplified signal to provide a second filtered signal,
a high frequency source for providing a high frequency reference signal,
a mixer unit operatively connected to said second filter unit for receiving said second filtered signal therefrom, said mixer unit is operatively connected to said high frequency source for receiving said high frequency reference signal therefrom, said mixer is configured for mixing said second filtered signal with said high frequency reference signal to provide a down converted output signal,
a third filter operatively connected to said mixer unit for filtering said down converted signal for producing a third filtered signal,
a fourth filter unit operatively connected to said third filter unit for filtering said third filtered signal to provide a fourth filtered signal, and
a second amplifier unit operatively connected to said fourth filter unit for amplifying said fourth filtered signal, said second amplifier is operatively connected to said analog to digital converting unit to provide said conditioned analog output thereto.

108. The system according to claim 107 wherein said first filter and said second filter are band pass filters, said third filter is a low pass filter, and said fourth filter is a notch filter.

109. The system according to claim 63 wherein said system further comprises pressure determining means for determining the external pressure level in the vicinity of said system.

110. The system according to claim 63 wherein said system further comprises a barometer unit operatively coupled to said processing unit for determining the barometric pressure level and for providing said processing unit with a signal representative of said barometric pressure level.

111. The system according to claim 63 wherein said system further comprises a user interface.

112. The system according to claim 111 wherein said user interface is selected from at least one user interface for allowing a user to control said system, at least one user interface for presenting information to a user of said system, and a combination thereof.

* * * * *